(12) United States Patent  (10) Patent No.: US 9,163,011 B2
Lueoend et al.  (45) Date of Patent: Oct. 20, 2015

(54) OXAZINE DERIVATIVES AND THEIR USE IN THE TREATMENT OF DISEASE

(75) Inventors: Rainer Martin Lueoend, Therwil (CH); Rainer Machauer, Freiburg (DE); Heinrich Rueeger, Flueh (CH); Siem Jacob Veenstra, Lorrach (DE)

(73) Assignee: NOVARTIS AG, Basel (CH)

( * ) Notice: Subject to any disclaimer, the term of this patent is extended or adjusted under 35 U.S.C. 154(b) by 280 days.

(21) Appl. No.: 13/592,580

(22) Filed: Aug. 23, 2012

(65) Prior Publication Data

US 2013/0172331 A1 Jul. 4, 2013

Related U.S. Application Data

(60) Provisional application No. 61/665,395, filed on Jun. 28, 2012, provisional application No. 61/527,172, filed on Aug. 25, 2011.

(51) Int. Cl.
*A61K 31/535* (2006.01)
*C07D 413/14* (2006.01)
*A61K 31/5355* (2006.01)
*A61K 45/06* (2006.01)

(52) U.S. Cl.
CPC .......... *C07D 413/14* (2013.01); *A61K 31/5355* (2013.01); *A61K 45/06* (2013.01)

(58) Field of Classification Search
CPC .. C07D 256/06; C07D 265/10; C07D 413/14; C07D 413/12; C07D 261/02; A61K 45/06; A61K 31/5355
USPC ................................................ 514/228.8, 96
See application file for complete search history.

(56) References Cited

U.S. PATENT DOCUMENTS

2012/0202803 A1  8/2012  Hilpert
2012/0245157 A1  9/2012  Masui et al.

FOREIGN PATENT DOCUMENTS

| EP | 2 147 914 | 1/2010 |
|---|---|---|
| EP | 2 360 155 | 8/2011 |
| WO | 2007/049532 | 5/2007 |
| WO | 2008/133273 | 11/2008 |
| WO | 2011/009898 | 1/2011 |
| WO | 2011/044181 A1 | 4/2011 |
| WO | 2011/069934 | 6/2011 |
| WO | 2011/070029 | 6/2011 |
| WO | 2011/071135 A1 | 6/2011 |
| WO | 2010/128058 | 11/2011 |
| WO | 2012/095521 | 7/2012 |
| WO | 2012/100179 | 7/2012 |
| WO | 2012/139993 | 10/2012 |
| WO | 2012/147763 | 11/2012 |
| WO | 2012/156284 | 11/2012 |
| WO | 2012/168164 | 12/2012 |
| WO | 2012/168175 | 12/2012 |

*Primary Examiner* — Jason Sims
*Assistant Examiner* — Ibrahim D Bori
(74) *Attorney, Agent, or Firm* — Joshua Roth

(57) ABSTRACT

The invention relates to novel oxazine derivatives of formula (I), and pharmaceutically acceptable salts thereof,

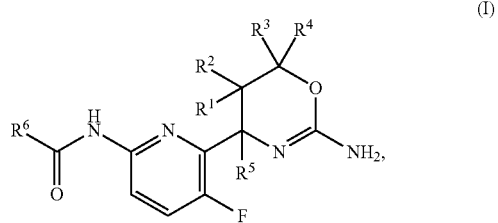

in which all of the variables are as defined in the specification, pharmaceutical compositions thereof, combinations thereof, and their use as medicaments, particularly for the treatment of Alzheimer's Disease or diabetes via inhibition of BACE-1 or BACE-2.

10 Claims, No Drawings

OXAZINE DERIVATIVES AND THEIR USE IN THE TREATMENT OF DISEASE

FIELD OF THE INVENTION

The invention relates to novel oxazine derivatives and pharmaceutically acceptable salts thereof, pharmaceutical compositions thereof, pharmaceutical combinations thereof, and their use as medicaments, particularly for the treatment of neurodegeneration via inhibition of BACE-1 or diabetes via inhibition of BACE-2.

BACKGROUND OF THE INVENTION

Alzheimer's Disease is a devastating neurodegenerative disorder. Its sporadic forms affect an elderly population (sharp increase in incidence at >75 years of age), in addition, there are various familial forms with an onset of the disease in the fourth or fifth decade of life. Pathologically, it is characterized by the presence of extracellular senile plaques, and intracellular neurofibrillar tangles in patient's brains. The core constituent of the senile plaques are small, 4 kDa amyloid peptides. They are generated by the proteolytic processing of a large transmembrane protein, amyloid precursor protein (APP). Cleavage of APP by beta-secretase (BACE-1) releases the soluble APP-beta fragment, while the 99-amino acid long C-terminus remains tethered to the membrane. This C-terminal fragment is subsequently proteolytically processed by gamma-secretase (an membrane multi-enzyme complex) to generate amyloid peptides of various length, predominantly 40 and 42 amino acids long (Hardy J, Selkoe D J (2002) Science; 297 (5580):353-356).

If, under pathologic conditions, the generation of these peptides occurs at an increased rate, or if their removal from the brain is disturbed, increased brain amyloid peptide concentrations leads to the formation of oligomers, fibrils and eventually plaques (Farris W, et al (2007) Am. J. Pathol.; 171 (1):241-251). It has been shown, that deposition of amyloid peptides and plaques in the brain is the first measurable event in the pathogenesis of Alzheimers Disease, and that it is the trigger for loss of synapses, synaptic contacts, and neurons (Grimmer T, et al (2009) Neurobiology of Aging; 30 (12): 1902-1909). Brain atrophy caused by massive neuron loss is followed by impairments in cognition, memory, orientation and the ability to perform the tasks of daily living, i.e. clinically manifest dementia (Okello A, et al (2009) Neurology; 73 (10):754-760).

BACE-1, also known as Asp2 or Memapsin 2, is a transmembrane aspartic protease highly expressed in neurons. It co-localizes with its substrate APP in Golgi and endocytic compartments (Willem M, Lammich S, Haass C (2009) Semin. Cell Dev. Biol; 20 (2):175-182). Knock-out studies in mice have demonstrated the absence of amyloid peptide formation, while the animals are healthy and fertile (Ohno M, et al (2007) Neurobiol. Dis.; 26 (1):134-145). Genetic ablation of BACE-1 in APP-overexpressing mice has demonstrated absence of plaque formation, and the reverse of cognitive deficits (Ohno M, et al (2004) Neuron; 41 (1):27-33). BACE-1 levels are elevated in the brains of sporadic Alzheimer's Disease patients (Hampel H, Shen Y (2009) Scand. J. Clin. Lab. Invest.; 69 (1):8-12).

Taken together, these findings suggest that the inhibition of BACE-1 may be a favourable therapeutic strategy for the treatment of Alzheimer's Disease.

Beta-site amyloid precursor protein cleaving enzyme 2 (BACE-2) is a transmembrane aspartic protease that is highly expressed in pancreatic β cells and other peripheral tissues (Brian D. Bennett, Safura Babu-Khan, Richard Loeloff, Jean-Claude Louis, Eileen Curran; Martin Citron, and Robert Vassar (2000) JJ. Biol. Chem. 275(27) 20647-20651). BACE-2 is closely related to BACE-1 or beta secretase. However, despite structural and sequence similarities the substrate specificity of BACE-1 and BACE-2 appear to be different. While Aβ or β-amyloid peptide is the main substrate of BACE-1, BACE-2 does not generate either form of Aβ (Vassar, R., Bennett, B. D., Babu-Khan, S., Kahn, S., Mendiaz, E. A., Denis, P., Teplow, D. B., Ross, S., Amarante, P., Loeloff, R., Luo, Y., Fisher, S., Fuller, J., Edenson, S., Lile, J., Jarosinski, M. A., Biere, A. L., Curran, E., Burgess, T., Louis, J.-C., Collins, F., Treanor, J., Rogers, G., and Citron, M. (1999) Science 286, 735-741).

Transmembrane protein 27 (TMEM27 or collectrin) plays an important role in β-cell proliferation and insulin secretion (Pinar Akpinar, Satoru Kuwajima, Jan Krützfeldt, and Markus Stoffel (2005) Tmem27: *Cell Metabolism.* 2(6) 385-397) and has been identified as a substrate for BACE-2 (WO 2010/063718). Tmem27 exists as a dimer and the extracellular domain is cleaved and shed from the plasma in a β cell-specific manner. Overexpression of full-length Tmem27, but not the truncated or soluble protein, increases β cell proliferation, suggesting that the full length protein is required for this biological function. Tcf1 (hepatocyte nuclear factor-1α, HNF-1α) controls the transcription of TMEM27. Mice with targeted deletion of Tcf1 exhibit decreased β cell mass, and knockdown of Tmem27 using RNAi results in a reduction of cell proliferation. Transgenic mice with increased expression of Tmem27 in pancreatic β cells exhibit increased β cell mass compared to their wild-type littermates. This data indicates that TMEM27 plays a role in control of β cell mass and that inhibition of BACE-2 which cleaves TMEM27 could be useful for treating loss of β cell mass and function, the underlying cause of diabetes.

Taken together, these findings suggest that the inhibition of BACE-2 may be a favourable therapeutic strategy for the treatment and prevention of metabolic disorders related to decreased β cell mass and/or function, such as type 2 diabetes.

Oxazine derivatives having BACE-1 and/or BACE-2 activity are described in the literature, for example WO 2011/069934 A1. However, there is an ongoing requirement for further structurally diverse BACE inhibitors which may have improved properties in terms of their inhibitory activity, selectivity, solubility, metabolism, pharmacokinetics and/or safety profile. It may also be advantageous to identify compounds which show selective inhibitory activity for BACE-1 over BACE-2 or BACE-2 over BACE-1.

SUMMARY OF THE INVENTION

The present invention therefore relates to novel oxazine derivatives having BACE inhibitory activity, to their preparation, to their medical use and to medicaments comprising them.

More particularly, in a first aspect the invention relates to a compound of the formula (I), or a pharmaceutically acceptable salt thereof:

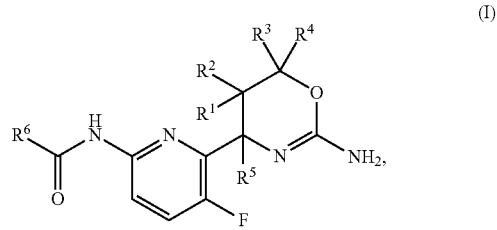

wherein
R¹ and R² are independently hydrogen or halogen;
R³ and R⁴ are independently hydrogen or $C_{1-3}$alkyl; or R³ and R⁴ taken together are cyclopropyl;
or R¹ and R⁴ are hydrogen and R² and R³ taken together are —$CH_2$—O—$CH_2$—;
R⁵ is $C_{1-3}$alkyl, halogen-$C_{1-3}$alkyl or $C_{1-3}$alkoxy-$C_{1-3}$alkyl; and
R⁶ is phenyl or a 5- or 6-membered monocyclic heteroaryl comprising 1, 2, 3 or 4 heteroatoms independently selected from N, O and S, and wherein said phenyl or heteroaryl is optionally substituted by 1, 2, 3 or 4 substituents independently selected from halogen, cyano, amino, hydroxy, $C_{1-4}$alkyl, halogen-$C_{1-4}$alkyl, halogen-$C_{1-4}$alkylthio, halogen-$C_{1-4}$alkoxy, $C_{1-4}$alkoxy, $C_{1-4}$alkoxy-$C_{1-4}$alkyl, $C_{1-4}$alkoxy-$C_{1-4}$alkoxy, $C_{1-4}$alkoxy-$C_{1-4}$alkylthio, $C_{1-4}$alkoxy-$C_{2-4}$alkenyl, $C_{1-4}$alkoxy-$C_{2-4}$alkynyl, hydroxy-$C_{1-4}$alkyl, hydroxy-$C_{2-4}$alkenyl and hydroxy-$C_{2-4}$alkynyl.

More particularly, in a second aspect the invention relates to a compound of the formula (I), or a pharmaceutically acceptable salt thereof:

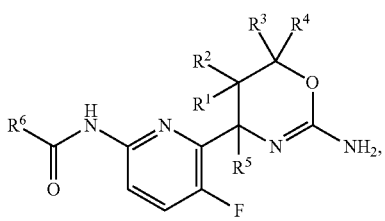

(I)

wherein
R¹ and R² are independently hydrogen or halogen;
R³ and R⁴ are independently hydrogen or $C_{1-3}$alkyl; or R³ and R⁴ taken together are cyclopropyl;
R⁵ is $C_{1-3}$alkyl, halogen-$C_{1-3}$alkyl or $C_{1-3}$alkoxy-$C_{1-3}$alkyl; and
R⁶ is phenyl or a 5- or 6-membered monocyclic heteroaryl comprising 1, 2, 3 or 4 heteroatoms independently selected from N, O and S, and wherein said phenyl or heteroaryl is optionally substituted by 1, 2, 3 or 4 substituents independently selected from halogen, cyano, amino, hydroxy, $C_{1-4}$alkyl, halogen-$C_{1-4}$alkyl, halogen-$C_{1-4}$alkylthio, halogen-$C_{1-4}$alkoxy, $C_{1-4}$alkoxy, $C_{1-4}$alkoxy-$C_{1-4}$alkyl, $C_{1-4}$alkoxy-$C_{1-4}$alkoxy, $C_{1-4}$alkoxy-$C_{1-4}$alkylthio, $C_{1-4}$alkoxy-$C_{2-4}$alkenyl, $C_{1-4}$alkoxy-$C_{2-4}$alkynyl, hydroxy-$C_{1-4}$alkyl, hydroxy-$C_{2-4}$alkenyl and hydroxy-$C_{2-4}$alkynyl.

More particularly, in a third aspect the invention relates to a compound of the formula (I), or a pharmaceutically acceptable salt thereof:

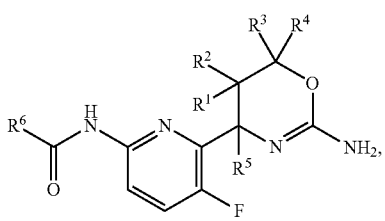

(I)

wherein
R¹ and R² are independently hydrogen or halogen;
R³ and R⁴ are independently hydrogen or $C_{1-3}$alkyl; or R³ and R⁴ taken together are cyclopropyl;
R⁵ is $C_{1-3}$alkyl, halogen-$C_{1-3}$alkyl or $C_{1-3}$alkoxy-$C_{1-3}$alkyl; and
R⁶ is phenyl or a 5- or 6-membered monocyclic heteroaryl comprising 1, 2, 3 or 4 heteroatoms independently selected from N, O and S, and wherein said phenyl or heteroaryl is optionally substituted by 1, 2, 3 or 4 substituents independently selected from halogen, cyano, amino, hydroxy, $C_{1-4}$alkyl, halogen-$C_{1-4}$alkyl, halogen-$C_{1-4}$alkylthio, halogen-$C_{1-4}$alkoxy, $C_{1-4}$alkoxy, $C_{1-4}$alkoxy-$C_{1-4}$alkyl, $C_{1-4}$alkoxy-$C_{1-4}$alkoxy and $C_{1-4}$alkoxy-$C_{1-4}$alkylthio.

DEFINITIONS

As used herein, the term "$C_{1-4}$alkyl" refers to a straight or branched hydrocarbon chain radical consisting solely of carbon and hydrogen atoms, containing no unsaturation, having from one to four carbon atoms, and which is attached to the rest of the molecule by a single bond. Examples of $C_{1-4}$alkyl include methyl, (R)-methyl, ethyl, n-propyl, 1-methylethyl (iso-propyl) n-butyl and 1,1-dimethylethyl (t-butyl). The term "$C_{1-3}$alkyl" refers to alkyl radicals as defined herein having from one to three carbon atoms.

As used herein, the term "$C_{2-4}$alkenyl" refers to a straight or branched hydrocarbon chain radical group consisting solely of carbon and hydrogen atoms, containing at least one double bond, having from two to four carbon atoms, and which is attached to the rest of the molecule by a single bond. Examples of $C_{2-6}$alkenyl include, ethenyl, prop-1-enyl and but-1-enyl.

As used herein, the term "$C_{2-4}$alkynyl" refers to a straight or branched hydrocarbon chain radical group consisting solely of carbon and hydrogen atoms, containing at least one triple bond, having from two to four carbon atoms, and which is attached to the rest of the molecule by a single bond. Examples of $C_{2-4}$alkynyl include ethynyl, prop-1-ynyl and but-1-ynyl.

As used herein, the term "$C_{1-4}$alkoxy" refers to a radical of the formula —O—$R_a$ where $R_a$ is a $C_{1-4}$alkyl radical as defined above. Examples of $C_{1-4}$alkoxy include methoxy, ethoxy, propoxy, isopropoxy, butoxy and isobutoxy. The term "$C_{1-3}$alkoxy" is to be construed accordingly.

As used herein, the term "$C_{1-4}$alkoxy-$C_{1-4}$alkyl" refers to a radical of the formula —$R_a$—O—$R_a$ where each $R_a$ is independently a $C_{1-4}$alkyl radical as defined above. The oxygen atom may be bonded to any carbon atom in either alkyl radical. Examples of $C_{1-4}$alkoxy-$C_{1-4}$alkyl include methoxymethyl, methoxy-ethyl, ethoxy-ethyl, 1-ethoxy-propyl and 2-methoxy-butyl. The term "$C_{1-3}$alkoxy-$C_{1-3}$alkyl" is to be construed accordingly.

As used herein, the term "$C_{1-4}$alkoxy-$C_{1-4}$alkoxy" refers to a radical of the formula —O—$R_a$—O—$R_a$ where each $R_a$ is independently a $C_{1-4}$alkyl radical as defined above. The oxygen atoms may be bonded to any alkyl radical carbon atom. Examples of $C_{1-4}$alkoxy-$C_{1-4}$alkoxy include methoxy-methoxy, methoxy-ethoxy, ethoxy-ethoxy, 1-ethoxy-propyoxy and 2-methoxy-butoxy.

As used herein, the term "$C_{1-4}$alkoxy-$C_{1-4}$alkylthio" refers to a radical of the formula —S—$R_a$—O—$R_a$ where each $R_a$ is independently a $C_{1-4}$alkyl radical as defined above. The oxygen and sulfur atoms may be bonded to any alkyl radical carbon atom. Examples of $C_{1-4}$alkoxy-$C_{1-4}$alkylthio include methoxy-methylthio, methoxy-ethylthio, ethoxy-ethylthio, 1-ethoxy-propylthio and 2-methoxy-butylthio.

As used herein, the term "$C_{1-4}$alkoxy-$C_{2-4}$alkenyl" refers to a radical of the formula —$R_b$—O—$R_a$ where $R_a$ is a $C_{1-4}$alkyl radical as defined above and $R_b$ is a $C_{2-4}$alkenyl radical as defined above. The oxygen atom may be bonded to any carbon atom in the alkyl radical and any carbon atom in the alkenyl radical. Examples of $C_{1-4}$alkoxy-$C_{2-4}$alkenyl include methoxy-ethenyl, ethoxy-ethenyl, 3-methoxy-propenyl, 1-ethoxy-propenyl and 2-methoxy-butenyl.

As used herein, the term "$C_{1-4}$alkoxy-$C_{2-4}$alkynyl" refers to a radical of the formula —$R_b$—O—$R_a$ where $R_a$ is a $C_{1-4}$alkyl radical as defined above and $R_b$ is a $C_{2-4}$alkynyl radical as defined above. The oxygen atom may be bonded to any carbon atom in the alkyl radical and any available carbon atom in the alkynyl radical. Examples of $C_{1-4}$alkoxy-$C_{2-4}$alkynyl include methoxy-ethynyl, ethoxy-ethynyl, 3-methoxy-propynyl, 1-ethoxy-propynyl and 2-methoxy-butynyl.

The term "halogen" refers to bromo, chloro, fluoro or iodo.

As used herein, the term "halogen-$C_{1-4}$alkyl" refers to a $C_{1-4}$alkyl radical, as defined above, substituted by one or more halo radicals, as defined above. Examples of halogen-$C_{1-4}$alkyl include trifluoromethyl, difluoromethyl, fluoromethyl, trichloromethyl, 2,2,2-trifluoroethyl, 1-fluoromethyl-2-fluoroethyl, 3-bromo-2-fluoropropyl and 1-bromomethyl-2-bromoethyl. The term "halogen-$C_{1-3}$alkyl" is to be construed accordingly.

As used herein, the term "halogen-$C_{1-4}$alkylthio" refers to a radical of the formula —S—$R_a$ where $R_a$ is a halogen-$C_{1-4}$alkyl radical as defined above. Examples of halogen-$C_{1-4}$alkylthio include trifluoromethylthio, difluoromethylthio, fluoromethylthio, trichloromethylthio, 2,2,2-trifluoroethylthio, 1-fluoromethyl-2-fluoroethylthio, 3-bromo-2-fluoropropylthio and 1-bromomethyl-2-bromoethylthio.

As used herein, the term "halogen-$C_{1-4}$alkoxy" refers to a $C_{1-4}$alkoxy radical, as defined above, substituted by one or more halo radicals, as defined above. Examples of halogen-$C_{1-4}$alkoxy include trifluoromethoxy, difluoromethoxy, fluoromethoxy, trichloromethoxy, 2,2,2-trifluoroethoxy, 1-fluoromethyl-2-fluoroethoxy, 3-bromo-2-fluoropropoxy and 1-bromomethyl-2-bromoethoxy.

As used herein, the term "heteroaryl" refers to a 5- or 6-membered aromatic monocyclic ring radical which comprises 1, 2, 3 or 4 heteroatoms individually selected from nitrogen, oxygen and sulfur. The heteroaryl radical may be bonded via a carbon atom or heteroatom. Examples of heteroaryl include furyl, pyrrolyl, thienyl, pyrazolyl, imidazolyl, thiazolyl, isothiazolyl, oxazolyl, isoxazolyl, triazolyl, tetrazolyl, pyrazinyl, pyridazinyl, pyrimidyl and pyridyl.

As used herein, the term "hydroxy$C_{1-4}$alkyl" refers to a $C_{1-4}$alkyl radical as defined above, wherein one of the hydrogen atoms of the $C_{1-4}$alkyl radical is replaced by OH. Examples of hydroxy$C_{1-4}$alkyl include hydroxy-methyl, 2-hydroxy-ethyl, 2-hydroxy-propyl, 3-hydroxy-propyl and 2-hydroxy-butyl.

As used herein, the term "hydroxy$C_{2-4}$alkenyl" refers to a $C_{2-4}$alkenyl radical as defined above, wherein one of the hydrogen atoms of the $C_{2-4}$alkenyl radical is replaced by OH. Examples of hydroxy$C_{1-4}$alkenyl include 2-hydroxy-ethenyl, 2-hydroxy-propenyl, 3-hydroxy-propenyl and 2-hydroxy-butenyl.

As used herein, the term "hydroxy$C_{2-4}$alkynyl" refers to a $C_{2-4}$alkynyl radical as defined above, wherein one of the hydrogen atoms of the $C_{2-4}$alkynyl radical is replaced by OH. Examples of hydroxy$C_{1-4}$alkynyl include 2-hydroxy-ethynyl, 3-hydroxy-propynyl and 2-hydroxy-butynyl.

As used herein, the term "a," "an," "the" and similar terms used in the context of the present invention (especially in the context of the claims) are to be construed to cover both the singular and plural unless otherwise indicated herein or clearly contradicted by the context. The use of any and all examples, or exemplary language (e.g. "such as") provided herein is intended merely to better illuminate the invention and does not pose a limitation on the scope of the invention otherwise claimed.

The term "compounds of the present invention" (unless specifically identified otherwise) refers to compounds of formula (I), (Ia), (Ib) or (Ic), compounds of the Examples, pharmaceutically acceptable salts of such compounds, and/or hydrates or solvates of such compounds, as well as, all stereoisomers (including diastereoisomers and enantiomers), tautomers and isotopically labeled compounds (including deuterium). The term "agents of the invention" is intended to have the same meaning as "compounds of the present invention".

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

As used herein, the term "prevention" of any particular disease or disorder refers to the administration of a compound of the invention to a subject before any symptoms of that disease or disorder are apparent.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, a subject is "in need of" a treatment if such subject would benefit biologically, medically or in quality of life from such treatment.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by BACE-1 or (ii) associated with BACE-1 activity, or (iii) characterized by activity (normal or abnormal) of BACE-1; or (2) reducing or inhibiting the activity of BACE-1. In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of BACE-1.

The meaning of the term "a therapeutically effective amount" as illustrated in the above embodiments for BACE-1 also applies by the same means to any other relevant proteins/peptides/enzymes, such as BACE-2, or cathepsin D.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment, "treat", "treating" or "treatment" refers to modulating the disease or disorder, either physically, (e.g., stabilization of a discernible symptom), physiologically, (e.g., stabilization of a physical parameter), or both.

DETAILED DESCRIPTION OF THE INVENTION

The present invention provides compounds and pharmaceutical compositions thereof that may be useful in the treatment or prevention of diseases, conditions and/or disorders modulated by BACE inhibition.

Embodiment 1

A compound of formula (I), or a pharmaceutically acceptable salt thereof, as defined above in the first aspect of the invention.

Embodiment 2

A compound of formula (I), or a pharmaceutically acceptable salt thereof, as defined above in the second aspect of the invention.

Embodiment 3

A compound of formula (I), or a pharmaceutically acceptable salt thereof, as defined above in the third aspect of the invention.

Embodiment 4

A compound according to any one of Embodiments 1 to 3, or a pharmaceutically acceptable salt thereof, wherein $R^1$ and $R^2$ are independently hydrogen or fluoro.

Embodiment 5

A compound according to any one of Embodiments 1 to 4, or a pharmaceutically acceptable salt thereof, wherein $R^1$ and $R^2$ are both fluoro.

Embodiment 6

A compound according to any one of Embodiments 1 to 5, or a pharmaceutically acceptable salt thereof, wherein $R^3$ and $R^4$ are independently hydrogen or methyl.

Embodiment 7

A compound according to any one of Embodiments 1 to 6, or a pharmaceutically acceptable salt thereof, wherein $R^3$ and $R^4$ are both hydrogen.

Embodiment 8

A compound according to any one of Embodiments 1 to 7, or a pharmaceutically acceptable salt thereof, wherein $R^5$ is methyl, fluoromethyl, difluoromethyl, methoxymethyl, methoxyethyl, ethoxymethyl or ethoxyethyl.

Embodiment 9

A compound according to any one of Embodiments 1 to 8, or a pharmaceutically acceptable salt thereof, wherein $R^5$ is methyl.

Embodiment 10

A compound according to any one of Embodiments 1 to 9, or a pharmaceutically acceptable salt thereof, wherein $R^6$ is phenyl or a 5- or 6-membered monocyclic heteroaryl comprising 1, 2, 3 or 4 heteroatoms independently selected from N, O and S, and wherein said phenyl or heteroaryl is optionally substituted by 1, 2, 3 or 4 substituents independently selected from halogen, cyano, amino, hydroxy, $C_{1-4}$alkyl, halogen-$C_{1-4}$alkyl, halogen-$C_{1-4}$alkylthio, halogen-$C_{1-4}$alkoxy, $C_{1-4}$alkoxy, $C_{1-4}$alkoxy-$C_{1-4}$alkyl, $C_{1-4}$alkoxy-$C_{1-4}$alkoxy and $C_{1-4}$alkoxy-$C_{1-4}$alkylthio.

Embodiment 11

A compound according to any one of Embodiments 1 to 9, or a pharmaceutically acceptable salt thereof, wherein $R^6$ is a 6-membered monocyclic heteroaryl comprising 1, 2, 3 or 4 heteroatoms independently selected from N, O and S, and wherein said phenyl or heteroaryl is optionally substituted by 1, 2, 3 or 4 substituents independently selected from halogen, cyano, amino, hydroxy, $C_{1-4}$alkyl, halogen-$C_{1-4}$alkyl, halogen-$C_{1-4}$alkylthio, halogen-$C_{1-4}$alkoxy, $C_{1-4}$alkoxy, $C_{1-4}$alkoxy-$C_{1-4}$alkyl, $C_{1-4}$alkoxy-$C_{1-4}$alkoxy and $C_{1-4}$alkoxy-$C_{1-4}$alkylthio.

Embodiment 12

A compound according to any one of Embodiments 1 to 9, or a pharmaceutically acceptable salt thereof, wherein $R^6$ is a pyridyl or pyrazinyl group which is optionally substituted by 1, 2 or 3 substituents independently selected from halogen, cyano, amino, hydroxy, $C_{1-4}$alkyl, halogen-$C_{1-4}$alkyl, halogen-$C_{1-4}$alkylthio, halogen-$C_{1-4}$alkoxy, $C_{1-4}$alkoxy, $C_{1-4}$alkoxy-$C_{1-4}$alkyl, $C_{1-4}$alkoxy-$C_{1-4}$alkoxy and $C_{1-4}$alkoxy-$C_{1-4}$alkylthio.

Embodiment 13

A compound according to any one of Embodiments 1 to 9, or a pharmaceutically acceptable salt thereof, wherein $R^6$ is a pyridyl or pyrazinyl group which is optionally substituted by 1, 2 or 3 substituents independently selected from halogen, cyano, amino, hydroxy, $C_{1-4}$alkyl, halogen-$C_{1-4}$alkyl, halogen-$C_{1-4}$alkylthio, halogen-$C_{1-4}$alkoxy, $C_{1-4}$alkoxy, $C_{1-4}$alkoxy-$C_{1-4}$alkyl, $C_{1-4}$alkoxy-$C_{1-4}$alkoxy, $C_{1-4}$alkoxy-$C_{1-4}$alkylthio, $C_{1-4}$alkoxy-$C_{2-4}$alkenyl, $C_{1-4}$alkoxy-$C_{2-4}$alkynyl, hydroxy-$C_{1-4}$alkyl, hydroxy-$C_{2-4}$alkenyl and hydroxy-$C_{2-4}$alkynyl.

Embodiment 14

A compound according to any one of Embodiments 1 to 9, or a pharmaceutically acceptable salt thereof, wherein $R^6$ is a pyridin-2-yl group or a pyrazin-2-yl group which is substituted by 2 substituents and wherein one of the substituents is located at the para position and one of the substituents is located at the ortho position of the pyridin-2-yl or pyrazin-2- yl group relative to the amide linker and wherein the substituents are independently selected from halogen, cyano, amino, hydroxy, $C_{1-4}$alkyl, halogen-$C_{1-4}$alkyl, halogen-$C_{1-4}$alkylthio, halogen-$C_{1-4}$alkoxy, $C_{1-4}$alkoxy, $C_{1-4}$alkoxy-$C_{1-4}$alkyl, $C_{1-4}$alkoxy-$C_{1-4}$alkoxy, $C_{1-4}$alkoxy-$C_{1-4}$alkylthio, $C_{1-4}$alkoxy-$C_{2-4}$alkenyl, $C_{1-4}$alkoxy-$C_{2-4}$alkynyl, hydroxy-$C_{1-4}$alkyl, hydroxy-$C_{2-4}$alkenyl and hydroxy-$C_{2-4}$alkynyl.

Embodiment 15

A compound according to any one of Embodiments 1 to 9, or a pharmaceutically acceptable salt thereof, wherein $R^6$ is a pyridin-2-yl group which is substituted by 2 substituents and wherein one of the substituents is located at the para position and one of the substituents is located at the ortho position of the pyridin-2-yl group relative to the amide linker and wherein the substituents are independently selected from halogen, cyano, amino, hydroxy, $C_{1-4}$alkyl, halogen-$C_{1-4}$alkyl, halogen-$C_{1-4}$alkylthio, halogen-$C_{1-4}$alkoxy, $C_{1-4}$alkoxy, $C_{1-4}$alkoxy-$C_{1-4}$alkyl, $C_{1-4}$alkoxy-$C_{1-4}$alkoxy and $C_{1-4}$alkoxy-$C_{1-4}$alkylthio.

Embodiment 16

A compound according to any one of Embodiments 1 to 9, or a pharmaceutically acceptable salt thereof, wherein $R^6$ is a pyridin-2-yl group which is substituted by 2 substituents and wherein one of the substituents is located at the para position and one of the substituents is located at the ortho position of the pyridin-2-yl group relative to the amide linker and wherein the substituents are independently selected from halogen, cyano, amino, hydroxy, methyl, trifluoromethyl, methoxy, trifluoromethoxy, 3-fluoro-propoxy, fluoromethoxy, 3-methoxy-propynyl, 2-methoxy-ethoxy and 3-hydroxy-propynyl.

Embodiment 17

A compound according to any one of Embodiments 1 to 9, or a pharmaceutically acceptable salt thereof, wherein $R^6$ is a pyridin-2-yl group which is substituted by 2 substituents and wherein one of the substituents is located at the para position and one of the substituents is located at the ortho position of the pyridin-2-yl group relative to the amide linker and wherein the substituents are independently selected from halogen, cyano, amino, hydroxy, methyl, trifluoromethyl, methoxy and trifluoromethoxy.

Embodiment 18

A compound according to any one of Embodiments 1 to 9, or a pharmaceutically acceptable salt thereof, wherein $R^6$ is a pyrazin-2-yl group which is substituted by 2 substituents and wherein one of the substituents is located at the para position and one of the substituents is located at the ortho position of the pyrazin-2-yl group relative to the amide linker and wherein the substituents are independently selected from halogen, cyano, amino, hydroxy, methyl, trifluoromethyl, methoxy, trifluoromethoxy, 3-fluoro-propoxy, fluoromethoxy, 3-methoxy-propynyl, 2-methoxy-ethoxy and 3-hydroxy-propynyl.

Embodiment 19

A compound according to any one of Embodiments 1 to 9, or a pharmaceutically acceptable salt thereof, wherein $R^6$ is 5-cyano-3-methyl-pyridin-2-yl.

Embodiment 20

A compound according to any one of Embodiments 1 to 9, or a pharmaceutically acceptable salt thereof, wherein $R^6$ is 3-chloro-5-trifluoromethyl-pyridin-2-yl.

Embodiment 21

A compound according to Embodiment 3 of formula (Ia), or a pharmaceutically acceptable salt thereof,

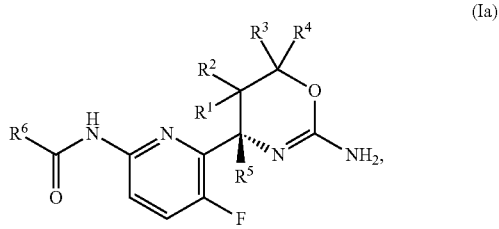

(Ia)

wherein
$R^1$ and $R^2$ are independently hydrogen or halogen;
$R^3$ and $R^4$ are independently hydrogen or $C_{1-3}$alkyl; or $R^3$ and $R^4$ taken together are cyclopropyl;
$R^5$ is $C_{1-3}$alkyl, halogen-$C_{1-3}$alkyl or $C_{1-3}$alkoxy-$C_{1-3}$alkyl; and
$R^6$ is phenyl or a 5- or 6-membered monocyclic heteroaryl comprising 1, 2, 3 or 4 heteroatoms independently selected from N, O and S, and wherein said phenyl or heteroaryl is optionally substituted by 1, 2, 3 or 4 substituents independently selected from halogen, cyano, amino, hydroxy, $C_{1-4}$alkyl, halogen-$C_{1-4}$alkyl, halogen-$C_{1-4}$alkylthio, halogen-$C_{1-4}$alkoxy, $C_{1-4}$alkoxy, $C_{1-4}$alkoxy-$C_{1-4}$alkyl, $C_{1-4}$alkoxy-$C_{1-4}$alkoxy and $C_{1-4}$alkoxy-$C_{1-4}$alkylthio.

Embodiment 22

A compound according to Embodiment 3 of formula (Ib), or a pharmaceutically acceptable salt thereof,

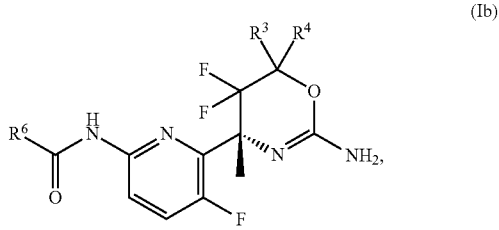

(Ib)

wherein
$R^3$ and $R^4$ are independently hydrogen or methyl; and
$R^6$ is a 6-membered monocyclic heteroaryl comprising 1, 2, 3 or 4 heteroatoms independently selected from N, O and S, and wherein said phenyl or heteroaryl is optionally substituted by 1, 2, 3 or 4 substituents independently selected halogen, cyano, amino, hydroxy, $C_{1-4}$alkyl, halogen-$C_{1-4}$alkyl, halo-

Embodiment 23

A compound according to Embodiment 3 of formula (Ic), or a pharmaceutically acceptable salt thereof,

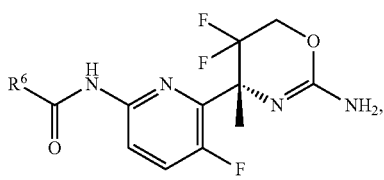

(Ic)

wherein
$R^6$ is a pyridin-2-yl group which is substituted by 2 substituents and wherein one of the substituents is located at the para position and one of the substituents is located at the ortho position of the pyridin-2-yl group relative to the amide linker and wherein the substituents are independently selected from halogen, cyano, amino, hydroxy, methyl, trifluoromethyl, methoxy and trifluoromethoxy.

Embodiment 24

A compound according to Embodiment 3 of formula (Ic), or a pharmaceutically acceptable salt thereof,

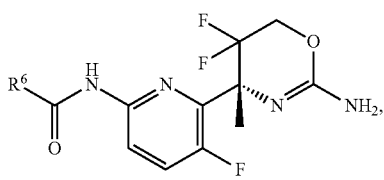

(Ic)

wherein
$R^6$ is a pyrazin-2-yl group which is substituted by 2 substituents and wherein one of the substituents is located at the para position and one of the substituents is located at the ortho position of the pyrazin-2-yl group relative to the amide linker and wherein the substituents are independently selected from halogen, cyano, amino, hydroxy, methyl, trifluoromethyl, methoxy and trifluoromethoxy.

Embodiment 25

A compound according to Embodiment 2, which is selected from:
5-Cyano-3-methyl-pyridine-2-carboxylic acid [6-(2-amino-5,5-difluoro-4-methyl-5,6-dihydro-4H-[1,3]oxazin-4-yl)-5-fluoro-pyridin-2-yl]-amide;
3-Chloro-5-cyano-pyridine-2-carboxylic acid [6-(2-amino-5,5-difluoro-4-methyl-5,6-dihydro-4H-[1,3]oxazin-4-yl)-5-fluoro-pyridin-2-yl]-amide;
3-Chloro-5-cyano-pyridine-2-carboxylic acid [6-(2-amino-5,5-difluoro-4,6,6-trimethyl-5,6-dihydro-4H-[1,3]oxazin-4-yl)-5-fluoro-pyridin-2-yl]-amide;
5-Cyano-3-methyl-pyridine-2-carboxylic acid {6-[2-amino-5,5-difluoro-4-(2-methoxy-ethyl)-5,6-dihydro-4H-[1,3]oxazin-4-yl]-5-fluoro-pyridin-2-yl}-amide;
3-Chloro-5-trifluoromethyl-pyridine-2-carboxylic acid {6-[2-amino-5,5-difluoro-4-(2-methoxy-ethyl)-5,6-dihydro-4H-[1,3]oxazin-4-yl]-5-fluoro-pyridin-2-yl}-amide;
3-Chloro-5-trifluoromethyl-pyridine-2-carboxylic acid [6-(2-amino-5,5-difluoro-4-methyl-5,6-dihydro-4H-[1,3]oxazin-4-yl)-5-fluoro-pyridin-2-yl]-amide;
3-Amino-5-trifluoromethyl-pyrazine-2-carboxylic acid [6-(2-amino-5,5-difluoro-4-methyl-5,6-dihydro-4H-[1,3]oxazin-4-yl)-5-fluoro-pyridin-2-yl]-amide;
3,5-Dichloro-pyridine-2-carboxylic acid [6-(2-amino-5,5-difluoro-4-methyl-5,6-dihydro-4H-[1,3]oxazin-4-yl)-5-fluoro-pyridin-2-yl]-amide;
3-Amino-5-(2,2,2-trifluoro-ethoxy)pyrazine-2-carboxylic acid [6-(2-amino-5,5-difluoro-4-methyl-5,6-dihydro-4H-[1,3]oxazin-4-yl)-5-fluoro-pyridin-2-yl]-amide;
3-Amino-5-(2,2-difluoro-ethoxy)-pyrazine-2-carboxylic acid [6-(2-amino-5,5-difluoro-4-methyl-5,6-dihydro-4H-[1,3]oxazin-4-yl)-5-fluoro-pyridin-2-yl]-amide;
3-Amino-5-(3-fluoro-propoxy)-pyrazine-2-carboxylic acid [6-(2-amino-5,5-difluoro-4-methyl-5,6-dihydro-4H-[1,3]oxazin-4-yl)-5-fluoro-pyridin-2-yl]-amide;
5-Methoxy-3-methyl-pyridine-2-carboxylic acid [6-(2-amino-5,5-difluoro-4-methyl-5,6-dihydro-4H-[1,3]oxazin-4-yl)-5-fluoro-pyridin-2-yl]-amide;
3-Amino-5-(3-methoxy-prop-1-ynyl)-pyridine-2-carboxylic acid [6-(2-amino-5,5-difluoro-4-methyl-5,6-dihydro-4H-[1,3]oxazin-4-yl)-5-fluoro-pyridin-2-yl]amide;
3-Amino-5-fluoromethoxy-pyrazine-2-carboxylic acid [6-(2-amino-5,5-difluoro-4-methyl-5,6-dihydro-4H-[1,3]oxazin-4-yl)-5-fluoro-pyridin-2-yl]-amide;
3-Amino-5-(2-methoxy-ethoxy)-pyrazine-2-carboxylic acid [6-(2-amino-5,5-difluoro-4-methyl-5,6-dihydro-4H-[1,3]oxazin-4-yl)-5-fluoro-pyridin-2-yl]-amide;
3-Amino-5-(3-hydroxy-prop-1-ynyl)-pyridine-2-carboxylic acid [6-(2-amino-5,5-difluoro-4-methyl-5,6-dihydro-4H-[1,3]oxazin-4-yl)-5-fluoro-pyridin-2-yl]-amide;
3-Amino-5-fluoro-pyridine-2-carboxylic acid [6-(2-amino-5,5-difluoro-4-methyl-5,6-dihydro-4H-[1,3]oxazin-4-yl)-5-fluoro-pyridin-2-yl]-amide;
3-Amino-5-chloro-pyridine-2-carboxylic acid [6-(2-amino-5,5-difluoro-4-methyl-5,6-dihydro-4H-[1,3]oxazin-4-yl)-5-fluoro-pyridin-2-yl]-amide;
3-Chloro-pyridine-2-carboxylic acid [6-(2-amino-5,5-difluoro-4-methyl-5,6-dihydro-4H-[1,3]oxazin-4-yl)-5-fluoro-pyridin-2-yl]-amide;
3-Chloro-5-(3-methoxy-prop-1-ynyl)pyridine-2-carboxylic acid [6-(2-amino-5,5-difluoro-4-methyl-5,6-dihydro-4H-[1,3]oxazin-4-yl)-5-fluoro-pyridin-2-yl]-amide;
3-Amino-5-difluoromethyl-pyrazine-2-carboxylic acid [6-(2-amino-5,5-difluoro-4-methyl-5,6-dihydro-4H-[1,3]oxazin-4-yl)-5-fluoro-pyridin-2-yl]-amide;
3-Amino-5-(2-chloro-ethoxy)-pyrazine-2-carboxylic acid [6-(2-amino-5,5-difluoro-4-methyl-5,6-dihydro-4H-[1,3]oxazin-4-yl)-5-fluoro-pyridin-2-yl]-amide;
3-Chloro-5-(2,2-difluoro-ethoxy)-pyridine-2-carboxylic acid [6-(2-amino-5,5-difluoro-4-methyl-5,6-dihydro-4H-[1,3]oxazin-4-yl)-5-fluoro-pyridin-2-yl]-amide;
3-Amino-5-(2-fluoro-ethoxy)-pyrazine-2-carboxylic acid [6-(2-amino-5,5-difluoro-4-methyl-5,6-dihydro-4H-[1,3]oxazin-4-yl)-5-fluoro-pyridin-2-yl]-amide;
3-Chloro-5-fluoromethoxy-pyridine-2-carboxylic acid [6-(2-amino-5,5-difluoro-4-methyl-5,6-dihydro-4H-[1,3]oxazin-4-yl)-5-fluoro-pyridin-2-yl]-amide;
3-Chloro-5-ethoxy-pyridine-2-carboxylic acid [6-(2-amino-5,5-difluoro-4-methyl-5,6-dihydro-4H-[1,3]oxazin-4-yl)-5-fluoro-pyridin-2-yl]-amide;

3-Amino-5-(penta-deutero-ethoxy)-pyrazine-2-carboxylic acid [6-(2-amino-5,5-difluoro-4-methyl-5,6-dihydro-4H-[1,3]oxazin-4-yl)-5-fluoro-pyridin-2-yl]-amide;
3-Amino-5-(2-methoxy-ethyl)-pyrazine-2-carboxylic acid [6-(2-amino-5,5-difluoro-4-methyl-5,6-dihydro-4H-[1,3]oxazin-4-yl)-5-fluoro-pyridin-2-yl]-amide;
4-Chloro-1-difluoromethyl-1H-pyrazole-3-carboxylic acid [6-(2-amino-5,5-difluoro-4-methyl-5,6-dihydro-4H-[1,3]oxazin-4-yl)-5-fluoro-pyridin-2-yl]-amide;
3-Amino-pyrazine-2-carboxylic acid [6-(2-amino-5,5-difluoro-4-methyl-5,6-dihydro-4H-[1,3]oxazin-4-yl)-5-fluoro-pyridin-2-yl]-amide;
3-Chloro-5-(3-hydroxy-prop-1-ynyl)-pyridine-2-carboxylic acid [6-(2-amino-5,5-difluoro-4-methyl-5,6-dihydro-4H-[1,3]oxazin-4-yl)-5-fluoro-pyridin-2-yl]-amide;
3-Amino-5-difluoromethyl-pyridine-2-carboxylic acid [6-(2-amino-5,5-difluoro-4-methyl-5,6-dihydro-4H-[1,3]oxazin-4-yl)-5-fluoro-pyridin-2-yl]-amide;
3-Amino-6-chloro-5-(1,1-difluoro-ethyl)-pyrazine-2-carboxylic acid [6-(2-amino-5,5-difluoro-4-methyl-5,6-dihydro-4H-[1,3]oxazin-4-yl)-5-fluoro-pyridin-2-yl]-amide;
5-Cyano-pyridine-2-carboxylic acid [6-(2-amino-5,5-difluoro-4-methyl-5,6-dihydro-4H-[1,3]oxazin-4-yl)-5-fluoro-pyridin-2-yl]-amide;
3-Chloro-5-(1,1-difluoro-ethyl)-pyridine-2-carboxylic acid [6-(2-amino-5,5-difluoro-4-methyl-5,6-dihydro-4H-[1,3]oxazin-4-yl)-5-fluoro-pyridin-2-yl]-amide; and
3-Amino-5-(1,1-difluoro-ethyl)-pyrazine-2-carboxylic acid [6-(2-amino-5,5-difluoro-4-methyl-5,6-dihydro-4H-[1,3]oxazin-4-yl)-5-fluoro-pyridin-2-yl]-amide;
and pharmaceutically acceptable salts thereof.

Embodiment 26

A compound according to Embodiment 2, which is selected from:
5-Cyano-3-methyl-pyridine-2-carboxylic acid [6-((R)-2-amino-5,5-difluoro-4-methyl-5,6-dihydro-4H-[1,3]oxazin-4-yl]amide;
3-Chloro-5-cyano-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide;
3-Chloro-5-cyano-pyridine-2-carboxylic acid [6-((R)-2-amino-5,5-difluoro-4,6,6-trimethyl-5,6-dihydro-4H-[1,3]oxazin-4-yl)-5-fluoro-pyridin-2-yl]-amide;
5-Cyano-3-methyl-pyridine-2-carboxylic acid {6-[(R)-2-amino-5,5-difluoro-4-(2-methoxy-ethyl)-5,6-dihydro-4H-[1,3]oxazin-4-yl]-5-fluoro-pyridin-2-yl}-amide;
3-Chloro-5-trifluoromethyl-pyridine-2-carboxylic acid {6-[(R)-2-amino-5,5-difluoro-4-(2-methoxy-ethyl)-5,6-dihydro-4H-[1,3]oxazin-4-yl]-5-fluoro-pyridin-2-yl}-amide;
3-Chloro-5-trifluoromethyl-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide;
3-Amino-5-trifluoromethyl-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide;
3,5-Dichloro-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide;
3-Amino-5-(2,2,2-trifluoro-ethoxy)pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide;
3-Amino-5-(2,2-difluoro-ethoxy)-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide;
3-Amino-5-(3-fluoro-propoxy)-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide;
5-Methoxy-3-methyl-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide;
3-Amino-5-(3-methoxy-prop-1-ynyl)-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide;
3-Amino-5-fluoromethoxy-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide;
3-Amino-5-(2-methoxy-ethoxy)-pyrazine-2-carboxylic acid [6-((R)-2-amino-5,5-difluoro-4-methyl-5,6-dihydro-4H-[1,3]oxazin-4-yl)-5-fluoro-pyridin-2-yl]amide;
3-Amino-5-(3-hydroxy-prop-1-ynyl)-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide;
3-Amino-5-fluoro-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide;
3-Amino-5-chloro-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide;
3-Chloro-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide;
3-Chloro-5-(3-methoxy-prop-1-ynyl)pyridine-2-carboxylic acid [6-((R)-2-amino-5,5-difluoro-4-methyl-5,6-dihydro-4H-[1,3]oxazin-4-yl)-5-fluoro-pyridin-2-yl]-amide;
3-Amino-5-difluoromethyl-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide;
3-Amino-5-(2-chloro-ethoxy)-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide;
3-Chloro-5-(2,2-difluoro-ethoxy)-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide;
3-Amino-5-(2-fluoro-ethoxy)-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide;
3-Chloro-5-fluoromethoxy-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide;
3-Chloro-5-ethoxy-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide;
3-Amino-5-(penta-deutero-ethoxy)-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide;
3-Amino-5-(2-methoxy-ethyl)-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide;
4-Chloro-1-difluoromethyl-1H-pyrazole-3-carboxylic acid [6-((R)-2-amino-5,5-difluoro-4-methyl-5,6-dihydro-4H-[1,3]oxazin-4-yl)-5-fluoro-pyridin-2-yl]-amide;
3-Amino-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide;
3-Chloro-5-(3-hydroxy-prop-1-ynyl)-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide;
3-Amino-5-difluoromethyl-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide;

3-Amino-6-chloro-5-(1,1-difluoro-ethyl)-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide;

5-Cyano-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide;

3-Chloro-5-(1,1-difluoro-ethyl)-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide; and 3-Amino-5-(1,1-difluoro-ethyl)-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide;

and pharmaceutically acceptable salts thereof.

On account of one or more than one asymmetrical carbon atom, which may be present in a compound of the formula (I), a corresponding compound of the formula (I) may exist in pure optically active form or in the form of a mixture of optical isomers, e.g. in the form of a racemic mixture. All of such pure optical isomers and all of their mixtures, including the racemic mixtures, are part of the present invention unless the context dictates otherwise (for example in an embodiment of the invention clearly specifying a single enantiomer).

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, unless the context dictates otherwise (for example in an embodiment of the invention clearly specifying a single enantiomer) the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

In one embodiment of the invention, there is provided a compound of the Examples having one chiral center as an isolated stereoisomer in the R configuration.

In one embodiment of the invention, there is provided a compound of the Examples having one chiral center as an isolated stereoisomer in the S configuration.

In one embodiment of the invention, there is provided a compound of the Examples having one chiral center as a racemic mixture.

It is also possible that the intermediates and compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the imidazole moiety where the proton may migrate between the two ring nitrogens. Valence tautomers include interconversions by reorganization of some of the bonding electrons.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

As used herein, the terms "salt" or "salts" refers to an acid addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. The compounds of the present invention may be capable of forming acid salts by virtue of the presence of amino groups or groups similar thereto.

In one embodiment, the invention relates to a compound of the formula (I), (Ia), (Ib) or (Ic) as defined herein, in free form. In another embodiment, the invention relates to a compound of the formula (I), (Ia), (Ib) or (Ic) as defined herein, in salt form. In another embodiment, the invention relates to a compound of the formula (I), (Ia), (Ib) or (Ic) as defined herein, in acid addition salt form. In a further embodiment, the invention relates to a compound of the formula (I), (Ia), (Ib) or (Ic) as defined herein, in pharmaceutically acceptable salt form. In yet a further embodiment, the invention relates to a compound of the formula (I), (Ia), (Ib) or (Ic) as defined herein, in pharmaceutically acceptable acid addition salt form. In yet a further embodiment, the invention relates to a compound of the formula (I), (Ia), (Ib) or (Ic) as defined herein, in hydrochloride salt form. In yet a further embodiment, the invention relates to any one of the compounds of the Examples in free form. In yet a further embodiment, the invention relates to any one of the compounds of the Examples in salt form. In yet a further embodiment, the invention relates to any one of the compounds of the Examples in acid addition salt form. In yet a further embodiment, the invention relates to any one of the compounds of the Examples in pharmaceutically acceptable salt form. In still another embodiment, the invention relates to any one of the compounds of the Examples in pharmaceutically acceptable acid addition salt form. In still another embodiment, the invention relates to any one of the compounds of the Examples in hydrochloride salt form.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

The pharmaceutically acceptable salts of the present invention can be synthesized from an acidic moiety, by conventional chemical methods. Generally, such salts can be prepared by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Furthermore, the compounds of the present invention, including their salts, may also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

The compounds of the present invention, including salts, hydrates and solvates thereof, may inherently or by design form polymorphs.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$, $^{31}P$, $^{32}P$, $^{35}S$, $^{36}Cl$, $^{125}I$ respectively. The invention includes various isotopically labeled compounds as defined herein, for example those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the present invention may be synthesized by synthetic routes that include processes analogous to those well-known in the chemical arts, particularly in light of the description contained herein. The starting materials are generally available from commercial sources such as Sigma-Aldrich or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), or Beilsteins Handbuch der organischen Chemie, 4, Aufl. ed. Springer-Verlag, Berlin, including supplements (also available via the Beilstein online database)).

For illustrative purposes, reaction schemes 1 and 2 depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Scheme 1

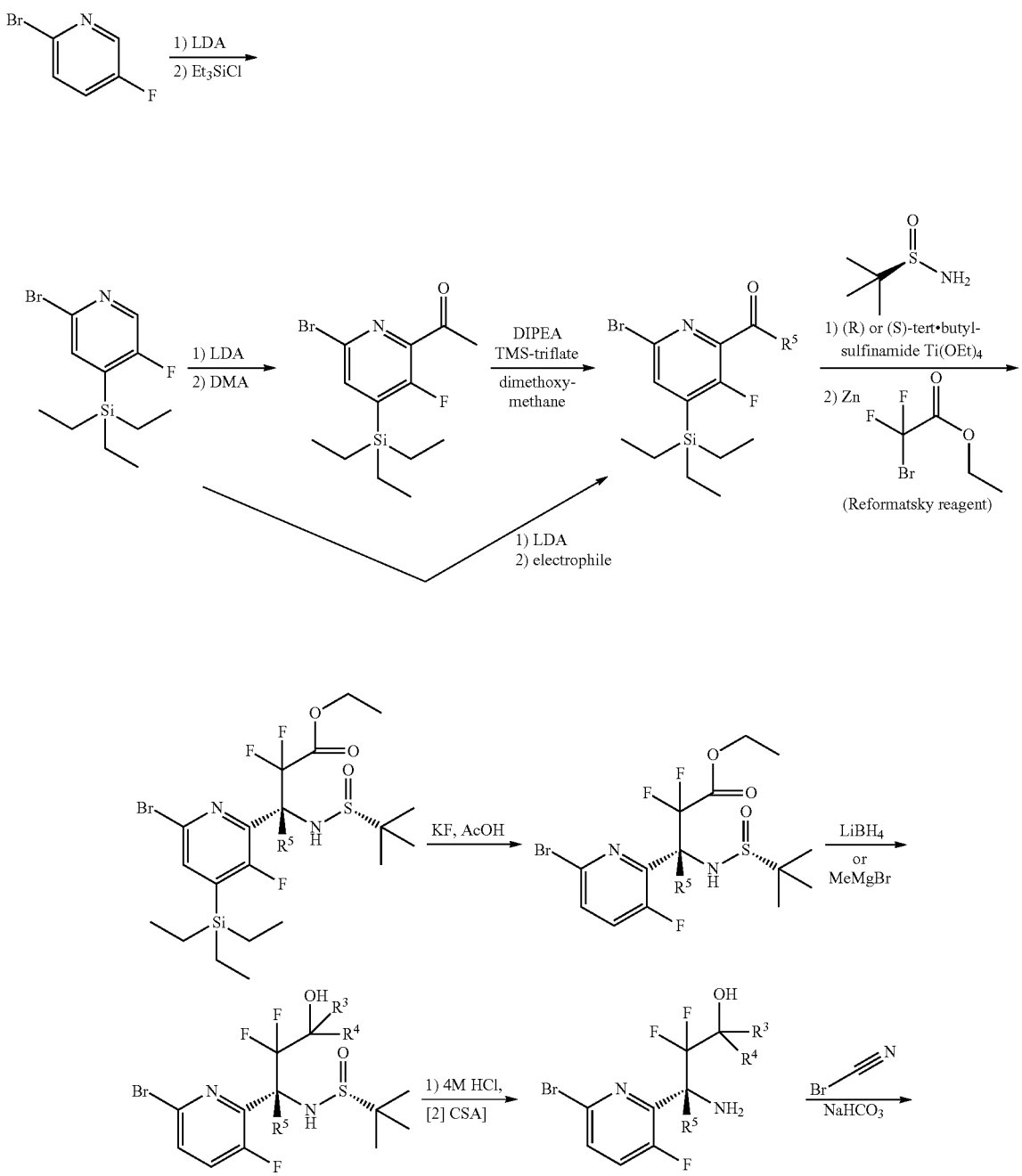

21
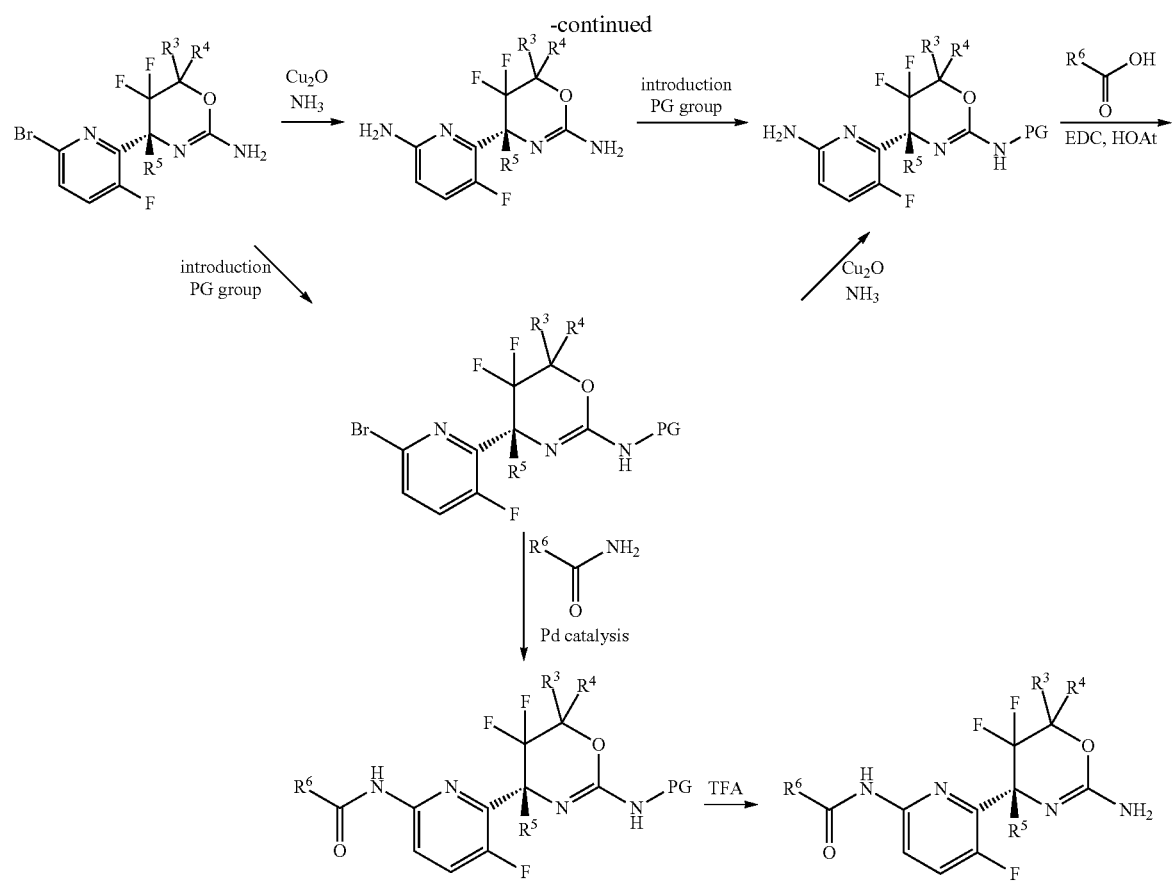
PG = Protection Group
e.g. DMTr or Boc
22
Scheme 2
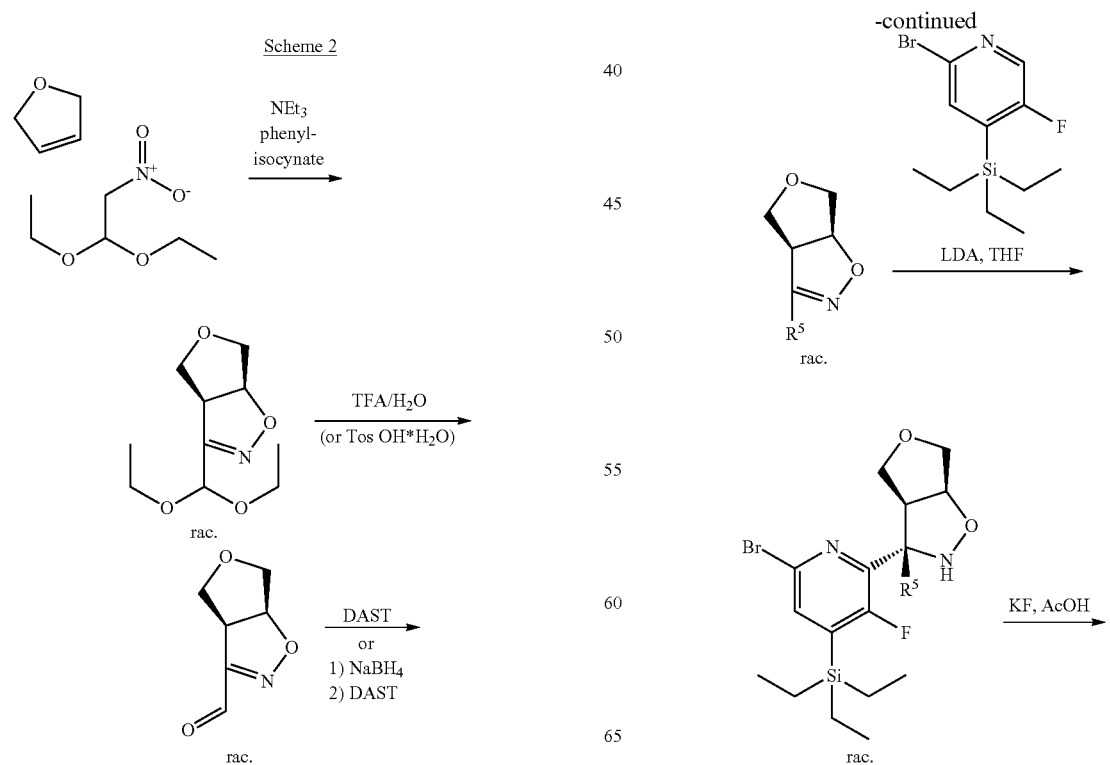

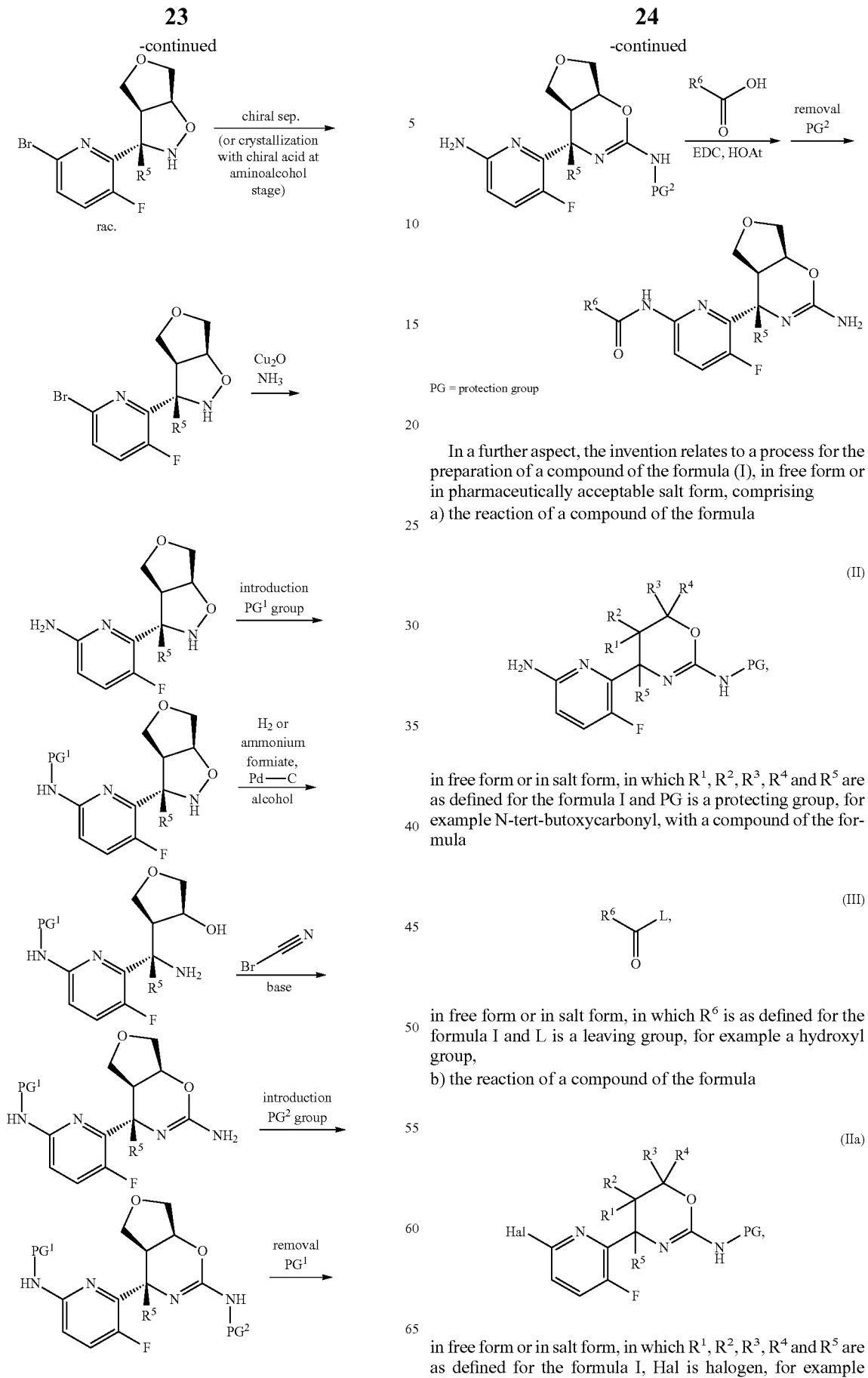

In a further aspect, the invention relates to a process for the preparation of a compound of the formula (I), in free form or in pharmaceutically acceptable salt form, comprising
a) the reaction of a compound of the formula in free form or in salt form, in which $R^1$, $R^2$, $R^3$, $R^4$ and $R^5$ are as defined for the formula I and PG is a protecting group, for example N-tert-butoxycarbonyl, with a compound of the formula in free form or in salt form, in which $R^6$ is as defined for the formula I and L is a leaving group, for example a hydroxyl group,
b) the reaction of a compound of the formula in free form or in salt form, in which $R^1$, $R^2$, $R^3$, $R^4$ and $R^5$ are as defined for the formula I, Hal is halogen, for example bromine, and PG is a protecting group, for example N-tert-butoxycarbonyl, with a compound of the formula

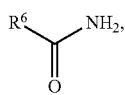
(IIIa)

in free form or in salt form, in which $R^6$ is as defined for the formula I,
c) the optional reduction, oxidation or other functionalisation of the resulting compound,
d) the cleavage of any protecting group(s) optionally present and
e) the recovery of the so obtainable compound of the formula I in free form or in salt form.

The above reactions can be effected according to conventional methods. For example, the reaction described in step (a) may be carried out in the presence of a suitable coupling agent, for example 1-hydroxy-7-azabenzotriazole, a suitable activating agent, for example 1-(3-dimethylaminopropyl)-3-ethylcarbodiimide hydrochloride, and optionally a suitable base, for example diisopropylethylamine, a suitable solvent, for example dimethylformamide, and at a suitable temperature, for example 0 to 50° C., more suitably 0 to 25° C.

The reaction described in step (b) may be carried out:
(i) in the presence of a suitable catalyst, for example tris(dibenzylidene-acetone) di palladium, a suitable ligand, for example Xantphos, a suitable base, for example cesium carbonate, a suitable solvent, for example dioxane, and at a suitable temperature, for example 10 to 100° C., more suitably 30 to 85° C.; or
(ii) in the presence of a suitable catalyst, for example copper iodide, a suitable ligand, for example rac-trans-N,N'-dimethylcyclohexane-1,2-diamine, a suitable base, for example potassium carbonate, a suitable solvent, for example dioxane, and at a suitable temperature, for example reflux temperature.

The starting materials of the formulae II, IIa, III and IIIa are known or may be prepared according to conventional procedures starting from known compounds, may be prepared from known compounds as described in the Examples, or may be prepared using procedures analogous to those described in the Examples.

The further optional reduction, oxidation or other functionalisation of compounds of formula (I) may be carried out according to methods well know to those skilled in the art.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/1, Georg Thieme Verlag, Stuttgart 1974, and in H.-D. Jakubke and H. Jeschkeit, "Aminosäuren, Peptide, Proteine" (Amino acids, Peptides, Proteins), Verlag Chemie, Weinheim, Deerfield Beach, and Basel 1982. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Salts of compounds of the present invention having at least one salt-forming group may be prepared in a manner known to those skilled in the art. For example, acid addition salts of compounds of the present invention are obtained in customary manner, e.g. by treating the compounds with an acid or a suitable anion exchange reagent.

Salts can be converted into the free compounds in accordance with methods known to those skilled in the art. Acid addition salts can be converted, for example, by treatment with a suitable basic agent.

For those compounds containing an asymmetric carbon atom, the compounds exist in individual optically active isomeric forms or as mixtures thereof, e.g. as racemic or diastereomeric mixtures. Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Enantiomers can also be separated by use of a commercially available chiral HPLC column.

The invention further includes any variant of the present processes, in which the reaction components are used in the form of their salts or optically pure material. Compounds of the invention and intermediates can also be converted into each other according to methods generally known to those skilled in the art.

Compounds of the formula (I), in free form or in pharmaceutically acceptable salt form, hereinafter often referred to as "agents of the invention", exhibit valuable pharmacological properties, when tested in vitro, and may, therefore, be useful in medicaments, in therapy or for use as research chemicals, for example as tool compounds.

For example, agents of the invention are inhibitors of BACE-1 and BACE-2 and may be used for the treatment or prevention of a condition, disease or disorder involving processing by such enzymes, particularly the generation of beta-amyloid and the subsequent aggregation into oligomers and fibrils, and loss of β cell mass and/or function.

The inhibiting properties of an agent of the invention towards proteases can be evaluated in the tests as described hereinafter.

Test 1: Inhibition of Human BACE-1

Recombinant BACE-1 (extracellular domain, expressed in baculovirus and purified using standard methods) at 0.1 to 1 nM concentrations is incubated with the test compound at various concentrations for 1 hour at room temperature in 100 mM acetate buffer, pH 4.5, containing 0.1% CHAPS. Activity was measured using a final concentration of 3 μM of the fluorescence-quenched substrate Q-C(HSO$_3$)-Ile-Asp-Leu-Ala-Val-Leu-Asp-HN—CH$_2$—CH$_2$-Mca, where Q=2-nitro-5-amino benzoic acid and Mca=7-methoxy-4-coumarinyl acetic acid. Catalytic turnover was monitored in a Spectramax Gemini fluorescence plate reader (Molecular Devices) in black 96-well microplates using excitation/emission wavelength of 325 nm and 400 nm, respectively. Fluorescence increase was followed for 15 min, in 1 minute's intervals. The fluorescence/time slopes were calculated from duplicate wells and from wells without inhibitor and the $IC_{50}$ values were calculated using a logistic 4-parameter model.

Test 2: Inhibition of Human BACE-2

Recombinant BACE-2 (extracellular domain, expressed in baculovirus and purified using standard methods) at 0.1 to 1 nM concentrations is incubated with the test compound at various concentrations for 1 hour at room temperature in 100 mM acetate buffer, pH 4.5, containing 0.1% CHAPS. Activity was measured using a final concentration of 3 µM of the fluorescence-quenched substrate Q-C(HSO$_3$)-Ile-Asp-Leu-Ala-Val-Leu-Asp-HN—CH$_2$—CH$_2$-Mca, where Q=2-nitro-5-amino benzoic acid and Mca=7-methoxy-4-coumarinyl acetic acid. Catalytic turnover was monitored in a Spectramax Gemini fluorescence plate reader (Molecular Devices) in black 96-well microplates using excitation/emission wavelength of 325 nm and 400 nm, respectively. Fluorescence increase was followed for 15 min, in 1 minute's intervals. The fluorescence/time slopes were calculated from duplicate wells and from wells without inhibitor and the $IC_{50}$ values were calculated using a logistic 4-parameter model.

Test 3: Inhibition of Human Cathepsin D

Recombinant cathepsin D (expressed as procathepsin D in baculovirus, purified using standard methods and activated by incubation in sodium formate buffer pH 3.7) is incubated with the test compound at various concentrations for 1 hour at room temperature in sodium formate or sodium acetate buffer at a suitable pH within the range of pH 3.0 to 5.0. Synthetic peptide substrate Mca-Gly-Lys-Pro-Ile-Leu-Phe-Phe-Arg-Leu-Lys(DNP)-D-Arg-NH$_2$ is added to a final concentration of 1 to 5 µM, and the increase in fluorescence is recorded at excitation of 325 nm and emission at 400 nm in a microplate spectro-fluorimeter for 5 to 30 minutes in 1-minute intervals. $IC_{50}$ values are calculated from the percentage of inhibition of cathepsin D-activity as a function of the test compound concentration.

Test 4: Inhibition of Cellular Release of Amyloid Peptide 1-40

Chinese hamster ovary cells are transfected with the human gene for amyloid precursor protein. The cells are plated at a density of 8000 cells/well into 96-well microtiter plates and cultivated for 24 hours in DMEM cell culture medium containing 10% FCS. The test compound is added to the cells at various concentrations, and the cells are cultivated for 24 hours in the presence of the test compound. The supernatants are collected, and the concentration of amyloid peptide 1-40 is determined using state of the art immunoassay techniques, for example sandwich ELISA, homogenous time-resolved fluorescence (HTRF) immunoassay, or electro-chemiluminescence immunoassay. The potency of the compound is calculated from the percentage of inhibition of amyloid peptide release as a function of the test compound concentration.

The compounds of the Examples showed the $IC_{50}$ values presented in Table 1 below when tested in Tests 1, 2 and 4. NT=Not Tested

TABLE 1

| Example No. | Test 1 BACE-1 $IC_{50}$ [µM] | Test 2 BACE-2 $IC_{50}$ [µM] | Test 4 Amyloid-β1-40 release $IC_{50}$ [µM] |
|---|---|---|---|
| 1 | 0.012 | 0.066 | 0.007 |
| 2 | 0.012 | 0.071 | 0.008 |
| 3 | 0.029 | 0.14 | 0.007 |
| 4 | 0.1 | 0.58 | 0.049 |
| 5 | >10 | >10 | >10 |
| 6 | 0.65 | 6.6 | 0.38 |
| 7 | 0.035 | 0.29 | 0.027 |
| 8 | 0.16 | 1.4 | 0.14 |
| 9 | 0.018 | 0.004 | 0.012 |
| 10 | 0.59 | 3.8 | 0.6 |
| 11 | 0.83 | 2.9 | 0.44 |
| 12 | 1.2 | >10 | 0.31 |
| 13 | 0.27 | 0.093 | 0.082 |
| 14 | NT | NT | 0.54 |
| 15 | 0.11 | 0.73 | 0.030 |
| 16 | 0.12 | 8.9 | NT |
| 17 | 0.24 | 8.2 | 0.062 |
| 18 | 0.33 | 0.12 | 0.088 |
| 19 | 0.06 | 0.048 | 0.045 |
| 20 | 0.36 | 0.095 | 0.088 |
| 21 | 0.083 | 0.84 | 0.081 |
| 22 | 0.19 | 0.58 | 0.06 |
| 23 | 8.7 | >10 | 2.9 |
| 24 | 0.24 | 4.5 | 0.25 |
| 25 | 0.57 | >10 | 0.48 |
| 26 | 0.11 | 0.027 | 0.057 |
| 27 | 0.29 | 0.42 | 0.45 |
| 28 | 1.9 | 10 | 0.84 |
| 29 | 0.15 | 5.6 | 0.07 |
| 30 | 0.019 | 0.007 | 0.013 |
| 31 | 0.54 | 0.49 | 0.18 |
| 32 | 0.06 | 0.93 | 0.019 |
| 33 | 0.14 | 0.26 | 0.066 |
| 34 | >10 | >10 | 6.5 |
| 35 | 0.054 | 0.26 | 0.014 |
| 36 | NT | NT | 0.058 |
| 37 | 0.064 | >10 | 0.31 |

Test 5: In Vivo Inhibitory Activity of Example Compounds

Male Sprague-Dawley rats, 220-280 g weight, (Charles River, France) were dosed by oral gavage with vehicle alone (0.1% Tween80, 0.5% methylcellulose in water) or with compound suspended in vehicle at a dose of 10 micromoles compound per kilogram body weight, 4 hours prior to sacrifice. The 4 hour timepoint was selected in order to compare the activity of compounds that have sufficient pharmacokinetic and biodistribution properties to reduce total brain Abeta within approximately three half-lives of the rat brain Abeta40 peptide.

Immediately prior to sacrifice, anaesthetized rat (spontaneous inhalation, 2-5% Isoflurane and air) were fixed in a stereotaxic apparatus on a raised platform, with anesthesia maintained though a nose cone. The angle of the head was tilted downward, perpendicular to the body, and a hypodermic needle lowered through the skin behind the occipital ridge, into the Cisterna magna. Cerebrospinal fluid (CSF) was withdrawn (~50-100 µL), dispensed into tubes (protein Lo-bind Eppendorf tubes for Abeta40 analysis, normal Eppendorph tubes for compound analysis), frozen on dry ice and stored at −80° C. until analysis. Rats were then immediately decapitated under anesthesia, trunk blood collected for analysis of compound levels and the brain retrieved. One half-forebrain was dissected by removing the cerebellum and olfactory bulbs, frozen in three pieces on a metal plate precooled on frozen $CO_2$ and stored in tubes at −80° C. until analysis for Abeta40. For the other half-brain, olfactory bulbs were discarded and a sagittal slice taken from the medial aspect, weighing ~200-400 mg, placed in glass HPLC tubes and frozen on dry ice until analysis for compound levels.

Soluble Abeta40 levels in the rat brain and CSF were quantified using a Meso Scale Discovery (MSD) 96-well MULTI-ARRAY human/rodent (4G8) Abeta40 Ultrasensitive Assay (#K110FTE-3, Meso Scale Discovery, Gaithersburg, USA). Forebrain sample homogenates were prepared by sonication in 9 volumes (w/v) of ice cold TBA. Fifty μL of 2% TX-100 in TBS-complete was added to 50 μL aliquots of the homogenate to reach a final concentration of 1% TX-100 in a 1:20 dilution. Samples were incubated on ice for 15 min interrupted with 3 short vortexing steps, then centrifuged (100 000×g, 4° C., 15 min), and 50 μL of supernatant collected. This was further diluted 1:5 with 3% Blocker A solution from the MSD kit to a final dilution of 1:100 and applied to the MSD plate. CSF samples containing blood were excluded. All other CSF samples were diluted with 1% Blocker A solution (from manufacturers kit) to reach a 1:20 CSF dilution. Calibration curves were prepared in 1% Blocker A solution spiked with synthetic Abeta1-40 peptide. Samples and calibration standards were applied in duplicate at a volume of 25 μL per well. Abeta40 concentrations of samples were estimated from the standard curve using SOFTmax PRO4.0.

The compounds of Examples 2, 3, 7 and 30 of the present invention and those of Examples 22, 39 and 71 of WO 2011/069934 A1 showed the effects presented in Table 2 below on Abeta lowering in rat brain and CSF when tested in Test 5. (n.s.=not statistically significant (Student's t-test))

TABLE 2

| Example No. | Structure | Abeta lowering in rat forebrain | Abeta lowering in rat CSF |
|---|---|---|---|
| 7 Present Invention | 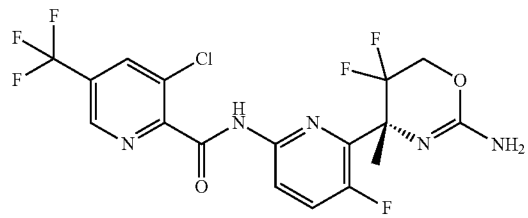 [SMILES: C[C@]1(c2nc(NC(=O)c3ncc(C(F)(F)F)cc3Cl)ccc2F)N=C(N)OCC1(F)F] | −63.6% | −67.9% |
| 39 WO 2011/069934 A1 | 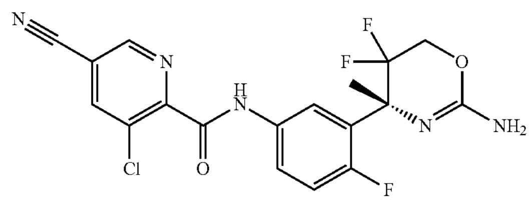 | −1.4% (n.s.) | −8.2% (n.s.) |
| 2 Present Invention | 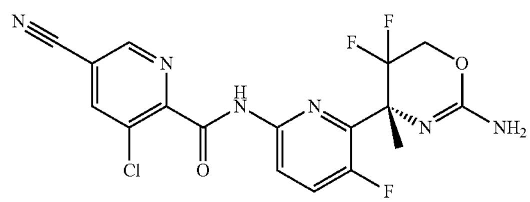 [SMILES: C[C@]1(c2nc(NC(=O)c3ncc(C#N)cc3Cl)ccc2F)N=C(N)OCC1(F)F] | −67.1% | −70.7% |
| 22 WO 2011/069934 A1 | 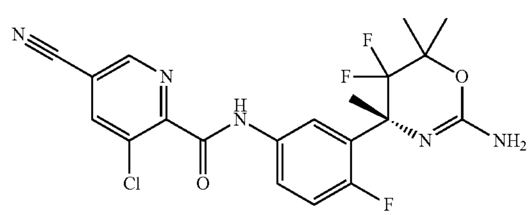 | −7.8% (n.s.) | −17.9% |
| 3 Present Invention | 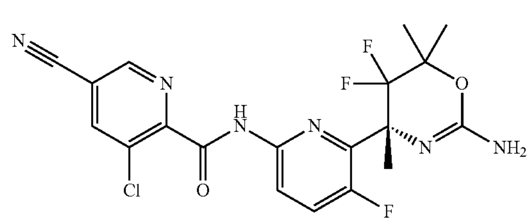 [SMILES: CC1(C)OC(N)=N[C@](C)(c2nc(NC(=O)c3ncc(C#N)cc3Cl)ccc2F)C1(F)F] | −20.0% | −35.3% |

TABLE 2-continued

| Example No. | Structure | Abeta lowering in rat forebrain | Abeta lowering in rat CSF |
|---|---|---|---|
| 71 WO 2011/069934 A1 | [Structure] | 5.6% (n.s.) | −30.4% |
| 30 Present Invention | [Structure] | −46.6% | −55.2% |

Blood, CSF and brain samples were also analyzed for compound levels using liquid chromatography/tandem mass spectrometry methods (LC/MS/MS). Brain samples were mixed with 2 volumes of $KH_2PO_4$ buffer and homogenized using a Covaris® device. Either 30 or 50 µL of blood, CSF or tissue homogenate were spiked with a structurally related internal standard and subsequently mixed with an at least 4-fold excess volume acetonitrile (protein precipitation). The supernatant was either directly, or after dilution with water, injected into the LC/MS/MS system for analysis.

Due to their inhibiting properties towards proteases, and BACE-1 in particular, agents of the invention may be useful, e.g., in the treatment or prevention of a variety of disabilitating psychiatric, psychotic, neurological or vascular states, e.g. of a condition, disease or disorder of the vascular system or of the nervous system, in which beta-amyloid generation or aggregation plays a role. Based on the inhibition of BACE-2 (beta-site APP-cleaving enzyme 2) or cathepsin D, which are close homologues of the pepsin-type aspartyl proteases and beta-secretase, and the correlation of BACE-2 or cathepsin D expression with a more tumorigenic or metastatic potential of tumor cells, the agents of the invention may also be useful as anti-cancer medicaments, e.g. in the suppression of the metastasis process associated with tumor cells. Furthermore, based on the inhibition of BACE-2 and the correlation of BACE-2 activity with TME27 cleavage and β cell mass, the agents of the invention may also be useful for treating or preventing loss of β cell mass and/or function, e.g. in the treatment of diabetes.

The said condition, disease or disorder of the vascular system or of the nervous system is exemplified by, and includes, without limitation, an anxiety disorder, such as panic disorder with or without agoraphobia, agoraphobia without history of panic disorder, an animal or other specific phobia, including a social phobia, social anxiety disorder, anxiety, obsessive-compulsive disorder, a stress disorder, including post-traumatic or acute stress disorder, or a generalized or substance-induced anxiety disorder; a neurosis; seizures; epilepsy, especially partial seizures, simple, complex or partial seizures evolving to secondarily generalized seizures or generalized seizures [absence (typical or atypical), myoclonic, clonic, tonic, tonic-clonic or atonic seizures]; convulsions; migraine; an affective disorder, including a depressive or bipolar disorder, e.g. single-episode or recurrent major depressive disorder, major depression, a dysthymic disorder, dysthymia, depressive disorder NOS, bipolar I or bipolar II manic disorder or cyclothymic disorder; a psychotic disorder, including schizophrenia or depression; neurodegeneration, e.g. neurodegeneration arising from cerebral ischemia; an acute, traumatic or chronic degenerative process of the nervous system, such as Parkinson's disease, Down's syndrome, dementia, e.g. senile dementia, dementia with Lewy bodies or a fronto-temporal dementia, a cognitive disorder, cognitive impairment, e.g. mild cognitive impairment, memory impairment, an amyloid neuropathy, a peripheral neuropathy, Alzheimer's disease, Gerstmann-Straeussler-Scheinker syndrome, Niemann-Pick disease, e.g. Niemann-Pick type C disease, brain inflammation, a brain, spinal cord or nerve injury, e.g. traumatic brain injury (TBI), a nerve trauma or a brain trauma, vascular amyloidosis, cerebral haemorrhage with amyloidosis, Huntington's chorea, amyotrophic lateral sclerosis, multiple sclerosis or fragile X syndrome; scrapie; cerebral amyloid angiopathy; an encephalopathy, e.g. transmissible spongiform encephalopathy; stroke; an attention disorder, e.g. attention deficit hyperactivity disorder; Tourette's syndrome; a speech disorder, including stuttering; a disorder of the circadian rhythm, e.g. in subjects suffering from the effects of jet lag or shift work; pain; nociception; itch; emesis, including acute, delayed or anticipatory emesis, such as emesis induced by chemotherapy or radiation, motion sickness, or post-operative nausea or vomiting; an eating disorder, including anorexia nervosa or bulimia nervosa; premenstrual syndrome; a muscle spasm or spasticity, e.g. in paraplegic patients; a hearing disorder, e.g. tinnitus or age-related hearing impairment; urinary incontinence; glaucoma; inclusion-body myositis; or a substance-related disorder, including substance abuse or dependency, including a substance, such as alcohol, withdrawal disorder. Agents of the invention may also be useful in enhancing cognition, e.g. in a subject suffering from a dementing condition, such as Alzheimer's disease; as premedication prior to anaesthesia or a minor medical intervention, such as endoscopy, including gastric endoscopy; or as ligands, e.g. radioligands or positron emission tomography (PET) ligands.

Due to their inhibiting properties towards BACE-2, compounds of the invention may be useful in the treatment or prevention a disease or disorder mediated by BACE-2. Diseases and disorders associated with BACE-2 include: metabolic syndrome (such as dyslipidemia, obesity, insulin resistance, hypertension, microalbuminemia, hyperuricaemia, and hypercoagulability), insulin resistance, glucose intolerance (also known as impaired glucose tolerance or impaired glucose tolerance, IGT), obesity, hypertension, or diabetic complications (such as retinopathy, nephropathy, diabetic foot, ulcers, macroangiopathies, metabolic acidosis or ketosis, reactive hypoglycaemia, hyperinsulinaemia), glucose metabolic disorder, dyslipidaemias of different origins, atherosclerosis and related diseases, high blood pressure, chronic heart failure, Syndrome X, diabetes, non-insulin-dependent diabetes mellitus, Type 2 diabetes, Type 1 diabetes, body weight disorders, weight loss, body mass index and leptin related diseases. Compounds of the invention may be suitable for preventing beta-cell degeneration such as apoptosis or necrosis of pancreatic beta cells, for improving or restoring the functionality of pancreatic cells, and/or increasing the number and/or size of pancreatic beta cells.

As used herein a patient is suffering from "obesity" if the patient exhibits at least one of:
- a body mass index (BMI), i.e. the patient's mass (in kg) divided by the square of the patient's height (in m), of 30 or more;
- an absolute waist circumference of >102 cm in men or >88 cm in women;
- a waist-to-hip ratio >0.9 in men or >0.85 in women; or
- a percent body fat >25% in men or >30% in women.

As used herein a patient is suffering from "Type 2 diabetes" if they meet the World Health Organisation criteria for Diabetes diagnosis (Definition and diagnosis of diabetes mellitus and intermediate hyperglycaemia, WHO, 2006), i.e. the patient exhibits at least one of:
- a fasting plasma glucose ≥7.0 mmol/l (126 mg/dl); or
- a venous plasma glucose ≥11.1 mmol/l (200 mg/dl) 2 hours after ingestion of 75 g oral glucose load.

As used herein a patient is suffering from "IGT" if they meet the World Health Organisation criteria for IGT diagnosis (Definition and diagnosis of diabetes mellitus and intermediate hyperglycaemia, WHO, 2006), i.e. the patient exhibits both of:
- a fasting plasma glucose ≤7.0 mmol/l (126 mg/dl); and
- a venous plasma glucose and ≤11.1 mmol/l (200 mg/dl) 2 hours after ingestion of 75 g oral glucose load.

As used herein, the term "metabolic syndrome" is a recognized clinical term used to describe a condition comprising combinations of Type II diabetes, impaired glucose tolerance, insulin resistance, hypertension, obesity, increased abdominal girth, hypertriglyceridemia, low HDL, hyperuricaernia, hypercoagulability and/or microalbuminemia. The American Heart Association has published guidelines for the diagnosis of metabolic syndrome, Grundy, S., et. al., (2006) *Cardiol. Rev.* Vol. 13, No. 6, pp. 322-327.

For the above-mentioned indications, the appropriate dosage will vary depending on, e.g., the compound employed as active pharmaceutical ingredient, the host, the mode of administration, the nature and severity of the condition, disease or disorder or the effect desired. However, in general, satisfactory results in animals are indicated to be obtained at a daily dosage of from about 0.1 to about 100, preferably from about 1 to about 50, mg/kg of animal body weight. In larger mammals, for example humans, an indicated daily dosage is in the range of from about 0.5 to about 2000, preferably from about 2 to about 200, mg of an agent of the invention conveniently administered, for example, in divided doses up to four times a day or in sustained release form.

An agent of the invention may be administered by any conventional route, in particular enterally, preferably orally, e.g. in the form of a tablet or capsule, or parenterally, e.g. in the form of an injectable solution or suspension.

In a further aspect, the invention relates to a pharmaceutical composition comprising an agent of the invention as active pharmaceutical ingredient in association with at least one pharmaceutically acceptable carrier or diluent and optionally in association with other auxiliary substances, such as inhibitors of cytochrome P450 enzymes, agents preventing the degradation of active pharmaceutical ingredients by cytochrome P450, agents improving or enhancing the pharmacokinetics of active pharmaceutical ingredients, agents improving or enhancing the bioavailability of active pharmaceutical ingredients, and so on, e.g. grapefruit juice, ketoconazole or, preferably, ritonavir. Such a composition may be manufactured in conventional manner, e.g. by mixing its components. Unit dosage forms contain, e.g., from about 0.1 to about 1000, preferably from about 1 to about 500, mg of an agent of the invention.

In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with
a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia;

and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

In accordance with the foregoing, in a further aspect, the invention relates to an agent of the invention for use as a medicament, for example for the treatment or prevention of a neurological or vascular condition, disease or disorder, in which beta-amyloid generation or aggregation plays a role, or for the suppression of the metastasis process associated with tumor cells, or for the treatment or prevention of loss of β cell mass and/or function. In one embodiment, the invention relates to an agent of the invention for use in the treatment of a disease or disorder mediated by BACE-1, BACE-2 or cathepsin D activity. In another embodiment, the invention relates to an agent of the invention for use in the treatment or prevention of Alzheimer's Disease or mild cognitive impairment. In a further embodiment, the invention relates to an agent of the invention for use in the treatment or prevention of insulin resistance, glucose intolerance, type 2 diabetes, obesity, hypertension, or diabetic complications. In yet another embodiment, the invention relates to a compound of the invention for use in the treatment of impaired glucose tolerance or Type 2 diabetes.

In a further aspect, the invention relates to the use of an agent of the invention as an active pharmaceutical ingredient in a medicament, for example for the treatment or prevention of a neurological or vascular condition, disease or disorder, in which beta-amyloid generation or aggregation plays a role, or for the suppression of the metastasis process associated with tumor cells, or for the treatment or prevention of loss of β cell mass and/or function. In a further embodiment, the invention relates to the use of an agent of the invention as an active pharmaceutical ingredient in a medicament for the treatment or prevention of a disease or disorder mediated by BACE-1, BACE-2 or cathepsin D activity. In one embodiment, the invention relates to the use of an agent of the invention as an active pharmaceutical ingredient in a medicament for the treatment or prevention of Alzheimer's Disease or mild cognitive impairment. In a further embodiment, the invention relates to the use of a compound of the invention as an active pharmaceutical ingredient in a medicament for the treatment or prevention of insulin resistance, glucose intolerance, type 2 diabetes, obesity, hypertension, or diabetic complications. In yet a further embodiment, the invention relates to the use of a compound of the invention as an active pharmaceutical ingredient in a medicament for the treatment or prevention of impaired glucose tolerance or Type 2 diabetes.

In a further aspect, the invention relates to the use of an agent of the invention for the manufacture of a medicament for the treatment or prevention of a neurological or vascular condition, disease or disorder, in which beta-amyloid generation or aggregation plays a role, or for the suppression of the metastasis process associated with tumor cells, or for the treatment or prevention of loss of β cell mass and/or function. In a further embodiment, the invention relates to the use of an agent of the invention for the manufacture of a medicament for the treatment or prevention of a disease or disorder mediated by BACE-1, BACE-2 or cathepsin D activity. In one embodiment, the invention relates to the use of an agent of the invention for the manufacture of a medicament for the treatment or prevention of Alzheimer's Disease or mild cognitive impairment. In a further embodiment, the invention relates to the use of a compound of the invention as an active pharmaceutical ingredient in a medicament for the treatment or prevention of insulin resistance, glucose intolerance, type 2 diabetes, obesity, hypertension, or diabetic complications. In yet a further embodiment, the invention relates to the use of a compound of the invention as an active pharmaceutical ingredient in a medicament for the treatment or prevention of impaired glucose tolerance or Type 2 diabetes.

In a further aspect, the invention relates to a method for the treatment or prevention of a neurological or vascular condition, disease or disorder, in which beta-amyloid generation or aggregation plays a role, or for the suppression of the metastasis process associated with tumor cells, or for the treatment or prevention of loss of β cell mass and/or function, in a subject in need of such treatment, prevention or suppression, which method comprises administering to such subject an effective amount of an agent of the invention. In one embodiment, the invention relates to a method of modulating BACE-1, BACE-2 or cathepsin D activity in a subject, wherein the method comprises administering to the subject a therapeutically effective amount of an agent of the invention. In another embodiment, the invention relates to a method for the treatment or prevention of a disease mediated by BACE-1, BACE-2 or cathepsin D activity, in a subject in need of such treatment or prevention, which method comprises administering to such subject an effective amount of an agent of the invention. In yet another embodiment, the invention relates to a method for the treatment or prevention of Alzheimer's Disease or mild cognitive impairment, in a subject in need of such treatment or prevention, which method comprises administering to such subject an effective amount of an agent of the invention. In a further embodiment, the invention relates to a method for the treatment or prevention of insulin resistance, glucose intolerance, type 2 diabetes, obesity, hypertension, or diabetic complications, in a subject in need of such treatment or prevention, which method comprises administering to such subject a therapeutically effective amount of a compound of the invention. In yet a further embodiment, the invention relates to a method for the treatment or prevention of impaired glucose tolerance or Type 2 diabetes, in a subject in need of such treatment or prevention, which method comprises administering to such subject a therapeutically effective amount of a compound of the invention.

An agent of the invention can be administered as sole active pharmaceutical ingredient or as a combination with at least one other active pharmaceutical ingredient effective, e.g., in the treatment or prevention of a neurological or vascular condition, disease or disorder, in which beta-amyloid generation or aggregation plays a role, or in the suppression of the metastasis process associated with tumor cells, or in the treatment or prevention of loss of β cell mass and/or function. Such a pharmaceutical combination may be in the form of a unit dosage form, which unit dosage form comprises a predetermined quantity of each of the at least two active components in association with at least one pharmaceutically acceptable carrier or diluent. Alternatively, the pharmaceutical combination may be in the form of a package comprising the at least two active components separately, e.g. a pack or dispenser-device adapted for the concomitant or separate administration of the at least two active components, in which these active components are separately arranged. In a further aspect, the invention relates to such pharmaceutical combinations.

In a further aspect, the invention therefore relates to a combination comprising a therapeutically effective amount of an agent of the invention and a second drug substance, for simultaneous or sequential administration.

In one embodiment, the invention provides a product comprising an agent of the invention and at least one other therapeutic agent as a combined preparation for simultaneous, separate or sequential use in therapy. In one embodiment, the therapy is the treatment of a disease or condition mediated by BACE-1, BACE-2 or cathepsin D activity, such as Alzheimer's Disease, mild cognitive impairment, impaired glucose tolerance or type 2 diabetes.

In one embodiment, the invention provides a pharmaceutical composition comprising an agent of the invention and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains an agent of the invention. In one embodiment, the kit comprises means for separately retaining said compositions, such as a container, divided bottle, or divided foil packet. An example of such a kit is a blister pack, as typically used for the packaging of tablets, capsules and the like. The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the agent of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent. Accordingly, the invention provides an agent of the invention for use in the treatment of a disease or condition mediated by BACE-1, BACE-2 or cathepsin D activity, such as Alzheimer's Disease, impaired glucose tolerance or type 2 diabetes, wherein the medicament is prepared for administration with another therapeutic agent. The invention also provides the use of another therapeutic agent for treating a disease or condition mediated by BACE-1, BACE-2 or cathepsin D activity, such as Alzheimer's Disease, impaired glucose tolerance or type 2 diabetes, wherein the medicament is administered with an agent of the invention.

The invention also provides an agent of the invention for use in a method of treating a disease or condition mediated by BACE-1, BACE-2 or cathepsin D activity, such as Alzheimer's Disease, impaired glucose tolerance or type 2 diabetes, wherein the agent of the invention is prepared for administration with another therapeutic agent. The invention also provides another therapeutic agent for use in a method of treating a disease or condition mediated by BACE-1, BACE-2 or cathepsin D activity, such as Alzheimer's Disease, impaired glucose tolerance or type 2 diabetes, wherein the other therapeutic agent is prepared for administration with an agent of the invention. The invention also provides an agent of the invention for use in a method of treating a disease or condition mediated by BACE-1, BACE-2 or cathepsin D activity, such as Alzheimer's Disease, impaired glucose tolerance or type 2 diabetes, wherein the agent of the invention is administered with another therapeutic agent. The invention also provides another therapeutic agent for use in a method of treating a disease or condition mediated by BACE-1, BACE-2 or cathepsin D activity, such as Alzheimer's Disease, impaired glucose tolerance or type 2 diabetes, wherein the other therapeutic agent is administered with an agent of the invention.

The invention also provides the use of an agent of the invention for treating a disease or condition mediated by BACE-1, BACE-2 or cathepsin D activity, such as Alzheimer's Disease, impaired glucose tolerance or type 2 diabetes, wherein the patient has previously (e.g. within 24 hours) been treated with another therapeutic agent. The invention also provides the use of another therapeutic agent for treating a disease or condition mediated by BACE-1, BACE-2 or cathepsin D activity, such as Alzheimer's Disease, impaired glucose tolerance or type 2 diabetes, wherein the patient has previously (e.g. within 24 hours) been treated with an agent of the invention.

In one embodiment, the invention relates to a compound of the invention, or a pharmaceutically acceptable salt thereof, in combination with another therapeutic agent wherein the other therapeutic agent is selected from:
(a) acetylcholinesterase inhibitors, such as donepezil (Aricept™), rivastigmine (Exelon™) and galantamine (Razadyne™);
(b) glutamate antagonists, such as memantine (Namenda™);
(c) antidepressant medications for low mood and irritability, such as citalopram (Celexa™), fluoxetine (Prozac™), paroxeine (Paxil™), sertraline (Zoloft™) and trazodone (Desyrel™);
(d) anxiolytics for anxiety, restlessness, verbally disruptive behavior and resistance, such as lorazepam (Ativan™) and oxazepam (Serax™);
(e) antipsychotic medications for hallucinations, delusions, aggression, agitation, hostility and uncooperativeness, such as aripiprazole (Abilify™), clozapine (Clozaril™), haloperidol (Haldol™), olanzapine (Zyprexa™), quetiapine (Seroquel™), risperidone (Risperdal™) and ziprasidone (Geodon™);
(f) mood stabilizers, such as carbamazepine (Tegretol™) and divalproex (Depakote™);
(g) nicotinic apha-7 agonists;
(h) mGluR5 antagonists;
(i) H3 agonists; and
(j) amyloid therapy vaccines, Thus, in one embodiment, the invention provides a pharmaceutical composition comprising;
i) a compound of the invention, or a pharmaceutically acceptable salt thereof, and
ii) at least one compound selected from
  a) acetylcholinesterase inhibitors,
  b) glutamate antagonists,
  c) antidepressant medications,
  d) anxiolytics,
  e) antipsychotic medications,
  f) mood stabilizers,
  g) nicotinic apha-7 agonists,
  h) mGluR5 antagonists,
  i) H3 agonists,
  j) amyloid therapy vaccines, and
ii) one or more pharmaceutically acceptable carriers.

In another embodiment, the invention relates to a compound of the invention, or a pharmaceutically acceptable salt thereof, in combination with another therapeutic agent wherein the other therapeutic agent is selected from:
a) antidiabetic agents, such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; protein tyrosine phosphatase-1B (PTP-1B) inhibitors such as PTP-112; GSK3 (glycogen synthase kinase-3) inhibitors such as SB-517955, SB-4195052, SB-216763, NN-57-05441 and NN-57-05445; RXR ligands such as GW-0791 and AGN-194204; sodium-dependent glucose cotransporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; and DPPIV (dipeptidyl peptidase IV) inhibitors such as vildagliptin;

b) hypolipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands; cholestyramine; fibrates; nicotinic acid bile acid binding resins such as cholestyramine; fibrates; nicotinic acid and other GPR109 agonists; cholesterol absorption inhibitors such as ezetimibe; CETP inhibitors (cholesterol-ester-transfer-protein inhibitors), and aspirin;

c) anti-obesity agents such as orlistat, sibutramine and Cannabinoid Receptor 1 (CB1) antagonists e.g. rimonabant; and d) anti-hypertensive agents, e.g., loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na—K-ATPase membrane pump such as digoxin; neutralendopeptidase (NEP) inhibitors; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as ditekiren, zankiren, terlakiren, aliskiren, RO 66-1132 and RO-66-1168; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors.

e) agonists of peroxisome proliferator-activator receptors, such as fenofibrate, pioglitazone, rosiglitazone, tesaglitazar, BMS-298585, L-796449, the compounds specifically described in the patent application WO 2004/103995 i.e. compounds of examples 1 to 35, or the compounds specifically described in the patent application WO 03/043985 i.e. compounds of examples 1 to 7 and especially (R)-1-{-4-[5-methyl-2-(4-trifluoromethyl-phenyl)-oxazol-4-ylmethoxy]-benzenesulfonyl}-2,3-dihydro-1H-indole-2-carboxylic or a salt thereof.

Thus, in one embodiment, the invention provides a pharmaceutical composition comprising;
i) a compound of the invention, or a pharmaceutically acceptable salt thereof, and
ii) at least one compound selected from
  a) antidiabetic agents,
  b) hypolipidemic agents,
  c) anti-obesity agents,
  d) anti-hypertensive agents,
  e) agonists of peroxisome proliferator-activator receptors, and ii) one or more pharmaceutically acceptable carriers.

Other specific anti-diabetic compounds are described by Patel Mona in *Expert Opin Investig Drugs*, 2003, 12(4), 623-633, in the FIGS. 1 to 7.

The structure of the therapeutic agents identified by code numbers, generic or trade names may be taken from the actual edition of the standard compendium "The Merck Index" or from databases, e.g., Patents International (e.g. IMS World Publications).

EXAMPLES

NMR Methods

Proton spectra are recorded on a Bruker 400 MHz ultrashield spectrometer unless otherwise noted. Chemical shifts are reported in ppm relative to methanol ($\delta$ 3.31), dimethyl sulfoxide ($\delta$ 2.50), or chloroform ($\delta$ 7.29). A small amount of the dry sample (1-5 mg) is dissolved in an appropriate deuterated solvent (0.7 mL). The shimming is automated and the spectra obtained in accordance with normal procedure.

General Chromatography Conditions

UPLC Method H1 ($Rt_{H1}$):
HPLC-column dimensions: 2.1×50 mm
HPLC-column type: Acquity UPLC HSS T3, 1.8 µm
HPLC-eluent: A) water+0.05 Vol.-% formic acid+3.75 mM ammonium acetate
B) ACN+0.04 Vol.-% formic acid
HPLC-gradient: 2-98% B in 1.4 min, 98% B 0.75 min, flow=1.2 ml/min
HPLC-column temperature: 50° C.
UPLC Method H2 ($Rt_{H2}$):
HPLC-column dimensions: 2.1×50 mm
HPLC-column type: Acquity UPLC HSS T3, 1.8 µm
HPLC-eluent: A) water+0.05 Vol.-% formic acid+3.75 mM ammonium acetate
B) ACN+0.04 Vol.-% formic acid
HPLC-gradient: 5-98 B in 1.4 min, 98% B 0.4 min, flow=1.0 ml/min
HPLC-column temperature: 60° C.
LCMS Method H3 ($Rt_{H3}$):
HPLC-column dimensions: 4.0×20 mm
HPLC-column type: Mercury MS Synergi, 2 µm
HPLC-eluent: A) water+0.1 Vol.-% formic acid, B) ACN
HPLC-gradient: 0.5 min 70% B, 70-100% B in 1 min, 0.9 min 100% B, flow=2.0 ml/min
HPLC-column temperature: 30° C.
LCMS Method H4 ($Rt_{H4}$):
HPLC-column dimensions: 2.1×30 mm
HPLC-column type: Ascentis Express C18, 2.8 µm
HPLC-eluent A) water+0.05 Vol.-% formic acid+3.75 mM ammonium acetate
B) ACN+0.04 Vol.-% formic acid
HPLC-gradient: 2-98 B in 1.4 min, 0.75 min 98% B, flow=1.2 ml/min
HPLC-column temperature: 50° C.
HPLC Method H5 ($Rt_{H5}$):
HPLC-column dimensions: 3.0×30 mm
HPLC-column type: Zorbax SB-C18, 1.8 µm
HPLC-eluent: A) water+0.05 Vol.-% TFA; B) ACN+0.05 Vol.-% TFA
HPLC-gradient: 0-100% B in 3.25 min, 0.75 min 100% B, flow=0.7 ml/min
HPLC-column temperature: 35° C.
UPLC Method H6 ($Rt_{H6}$):
HPLC-column dimensions: 2.1×50 mm
HPLC-column type: Acquity UPLC HSS T3, 1.8 µm
HPLC-eluent: A) water+0.1 Vol.-% TFA; B) ACN+0.1 Vol.-% TFA
HPLC-gradient: 10-95 B in 1.5 min, flow=1.0 ml/min
HPLC Method H7 ($Rt_{H7}$):
HPLC-column dimensions: 3.0×30 mm
HPLC-column type: Zorbax SB-C18, 1.8 µm
HPLC-eluent: A) water+0.05 Vol.-% TFA; B) ACN+0.05 Vol.-% TFA
HPLC-gradient: 30-100% B in 3.25 min, 0.75 min 100% B, flow=0.7 ml/min
HPLC-column temperature: 35° C.
HPLC Method H8 ($Rt_{H8}$):
HPLC-column dimensions: 3.0×30 mm
HPLC-column type: Zorbax SB-C18, 1.8 µm
HPLC-eluent: A) water+0.05 Vol.-% TFA; B) ACN+0.05 Vol.-% TFA
HPLC-gradient: 10-100% B in 3.25 min, 0.75 min 100% B, flow=0.7 ml/min
HPLC-column temperature: 35° C.

Abbreviations

ACN acetonitrile
AcOH acetic acid
aq. aqueous
$Boc_2O$ tert-butyl dicarbonate
BuLi butyl lithium
CSA campher sulfonic acid
DAST diethylaminosulfur trifluoride
dba dibenzylideneacetone
DCM dichloromethane
DEAD diethyl azodicarboxylate
DIAD diisopropyl azodicarboxylate
DIPEA diisopropylethylamine
DMA dimethylacetamide
DMF dimethylformamide
DMSO dimethylsulfoxide
DMTr 4,4'-dimethoxytrityl
DPPF 1,1'-bis-diphenylphosphino-ferrocene
EDC 1-(3-dimethylaminopropyl)-3-ethylcarbodiimide
$Et_3N$ triethylamine
EtOAc ethyl acetate
EtOH ethanol
h hour(s)
hex hexane
HOAt 1-hydroxy-7-aza-benztriazole
HPLC high performance liquid chromatography
LCMS liquid chromatography with mass spectrometry
LDA lithium diisopropylamide
mCPBA 3-chloroperbenzoic acid
MeOH methanol
min minute(s)
MS mass spectrometry
$NEt_3$ triethylamine
NMR nuclear magnetic resonance spectrometry
$R_f$ retention factor (TLC)
RP reverse phase
Rt retention time
rt room temperature
sat. saturated
TBME tert-butyl-methyl-ether
TFA trifluoroacetic acid
THF tetrahydrofuran
TLC thin layer chromatography Xantphos 4,5-bis(diphenylphosphino)-9,9-dimethylxanthene

Example 1

5-Cyano-3-methyl-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide

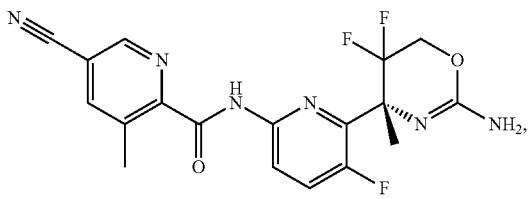 [SMILES: Cc1cc(C#N)cnc1C(=O)Nc1ccc(F)c([C@@]2(C)N=C(N)OCC2(F)F)n1]

a) 2-Bromo-5-fluoro-4-triethylsilanylpyridine

To a solution of diisopropylamine (25.3 g, 250 mmol) in THF (400 ml) was added n-BuLi (100 ml, 2.5 mol/L in hexanes) below −50° C. A solution of 2-bromo-5-fluoropyridine (41.9 g, 238 mmol) in THF (60 ml) was added to the LDA-solution at −78° C. in a dropwise manner below −63° C. After 60 minutes at −78° C. triethylchlorosilane (44 ml, 262 mmol) was added in a fast manner keeping the temperature below −50° C. The cooling bath was removed and the reaction mixture was allowed to reach −20° C. The reaction mixture was poured on a mixture of 1M aq. HCl (250 ml) and aq. NH$_4$Cl (10%). Tert.-butyl methyl ether was added and the layers were separated. The organic phase was washed with brine, dried over magnesium sulfate, filtered and evaporated to give a yellow liquid. Distillation (bp. 99-101° C., 0.5 mmHg). afforded the title compound as a slightly yellow liquid: 66.26 g (96% yield).

$^1$H-NMR (400 MHz, CDCl$_3$): δ 8.17 (s, 1H), 7.42 (d, 1H), 1.01-0.97 (m, 9H), 0.92-0.87 (m, 6H).

b) 1-(6-Bromo-3-fluoro-4-triethylsilanyl-pyridin-2-yl)-ethanone

To a solution of diisopropylamine (25.4 g, 251 mmol) in THF (500 ml) was added n-BuLi (100 ml, 2.5 mol/L in hexanes) below −50° C. A solution of 2-bromo-5-fluoro-4-triethylsilanyl-pyridine (56.04 g, 193 mmol) in THF (60 ml) was added to the LDA-solution at −78° C. in a dropwise manner below −65° C. After 70 minutes at −78° C. DMA (23.51 ml, 251 mmol) was added dropwise in a fast manner to the deep red solution keeping the temperature below −57° C. After 15 minutes the cooling bath was removed and the reaction mixture was allowed to reach −40° C. The cold reaction mixture was poured on a mixture of 2M aq. HCl (250 ml)/water (200 ml)/brine (100 ml). Tert.-butyl methyl ether was added and the layers were separated. The organic phase was washed twice with brine, dried over magnesium sulfate, filtered and evaporated to give a yellow oil. The crude product (64.76 g) was chromatographed over silica gel (hexane/TBME) to give the title compound as a yellow liquid: 58.3 g (91% yield).

TLC (hexane/TBME 99:1): R$_f$=0.25;

$^1$H-NMR (400 MHz, CDCl$_3$): δ 7.55 (d, 1H), 2.67 (3, 3H), 0.98-0.93 (m, 9H), 0.91-0.85 (m, 6H).

c) (R)-2-Methyl-propane-2-sulfinic acid [1-(6-bromo-3-fluoro-4-triethylsilanyl-pyridin-2-yl)-eth-(E)-ylidene]-amide A mixture of titantetraethoxide (4.26 g, 18.69 mmol), (R)-tert.-butylsulfinamide (1.246 g, 10.28 mmol) and 1-(6-bromo-3-fluoro-4-triethylsilanyl-pyridin-2-yl)-ethanone (3.45 g, 9.34 mmol, 90% pure) in THF (25 ml) was refluxed under a nitrogen atmosphere for 6 hours. The cold reaction mixture was poured onto icecold brine (200 ml) with gentle stirring. The precipitate was filtered through a pad of hyflo and washed with ethyl acetate. The filtrate was diluted with ethyl acetate and washed with brine, dried over sodium sulfate, filtered and evaporated. The crude yellow oil (4.55 g) was chromatographed over silica gel (cyclohexane/ethyl acetate 94:6) to give the title compound as a yellow oil. 3.35 g (82% yield).

TLC (cyclohexane/ethyl acetate 5:1): R$_f$=0.50;

HPLC: Rt$_{H1}$=1.56 min; ESIMS: 435, 437 [(M+H)$^+$, 1Br];

$^1$H-NMR (400 MHz, CDCl$_3$): δ 7.48 (d, 1H), 2.28 (s, 3H), 1.34 (s, 9H), 1.01-0.98 (m, 9H), 0.92-0.89 (m, 6H).

d) (R)-3-(6-Bromo-3-fluoro-4-triethylsilanyl-pyridin-2-yl)-2,2-difluoro-3-((R)-2-methyl-propane-2-sulfinylamino)-butyric acid ethyl ester To a suspension of zinc (466 mg, 7.12 mmol) and copper(I) chloride (34 mg, 0.344 mmol) in dry THF (20 ml) were added 3 drops of trimethylchlorosilane under nitrogen to activate the zinc. After 10 minutes ethyl 2-bromo-2,2-difluoroacetate (1.398 g, 6.89 mmol) was added slowly by syringe over a period of 10 minutes at 25° C. (slightly exothermic). The reaction mixture was kept in an ultrasound bath for 45 minutes. This black fine suspension was added dropwise to a solution of (R)-2-methyl-propane-2-sulfinic acid [1-(6-bromo-3-fluoro-4-triethylsilanyl-pyridin-2-yl)-eth-(E)-ylidene]-amide) (1 g, 2.296 mmol) in dry THF (10 ml) at it under inert atmosphere. After 4 h at it the reaction mixture was added to a cold aq. ammonium chloride solution (5%) and was diluted with ethyl acetate. The organic phase was washed with aq. citric acid (5% solution), water, sat. sodium bicarbonate solution and brine, dried over sodium sulfate, filtered and concentrated. The crude brownish oil (1.5 g) was chromatographed over silica gel (cyclohexane/ethyl acetate 83:17) to give the title compound as a light yellow oil. 984 mg (77% yield).

TLC (cyclohexane/ethyl acetate 2:1): R$_f$=0.46;

HPLC: Rt$_{H1}$=1.54 min; ESIMS: 559, 561 [(M+H)$^+$, 1Br];

$^1$H-NMR (400 MHz, CDCl$_3$): δ 7.40 (d, 1H), 5.48 (s, NH), 4.38 (q, 2H), 2.07 (s, 3H), 1.26 (s, 9H), 1.00-0.96 (m, 9H), 0.90-0.86 (m, 6H).

Minor diastereoisomer R$_f$=0.64 (2:1 cyclohexane:ethyl acetate).

e) (R)-3-(6-Bromo-3-fluoro-pyridin-2-yl)-2,2-difluoro-3-((R)-2-methyl-propane-2-sulfinylamino)-butyric acid ethyl ester Freshly ground KF (195 mg, 3.36 mmol) was added to a solution of (R)-3-(6-bromo-3-fluoro-4-triethylsilanyl-pyridin-2-yl)-2,2-difluoro-3-((R)-2-methyl-propane-2-sulfinylamino)-butyric acid ethyl ester (940 mg, 1.68 mmol) and acetic acid (0.192 ml, 3.36 mmol) in THF (7 ml). DMF (7 ml) was added and the suspension was stirred at rt. After 2 h the reaction mixture was diluted with ethyl acetate and washed with sat. sodium bicarbonate solution and brine, dried over sodium sulfate, filtered and evaporated. The crude product (733 mg) was chromatographed over silica gel (cyclohexane/ethyl acetate 7:3) to give the title compound as a slightly yellow oil. 664 mg (88% yield).

TLC (cyclohexane/ethyl acetate 1:1): $R_f$=0.38;
HPLC: $Rt_{H1}$=1.08 min; ESIMS: 445, 447 [(M+H)$^+$, 1Br];
$^1$H-NMR (400 MHz, CDCl$_3$): δ 7.51-7.46 (dd, 1H), 7.35 (t, 1H), 5.38 (br. s, 1H, NH), 4.37 (q, 2H), 2.07 (s, 3H), 1.39 (t, 3H), 1.26 (s, 9H).

f) (R)-2-Methyl-propane-2-sulfinic acid [(R)-1-(6-bromo-3-fluoro-pyridin-2-yl)-2,2-difluoro-3-hydroxy-1-methyl-propyl]amide To a solution of (R)-3-(6-bromo-3-fluoro-pyridin-2-yl)-2,2-difluoro-3-((R)-2-methyl-propane-2-sulfinylamino)-butyric acid ethyl ester (513 mg, 1.15 mmol) in THF (11.5 ml) was added lithiumborohydride (52.8 mg, 2.30 mmol). The slightly exothermic reaction was stirred for 2.5 h at room temperature. Crushed ice was added and the reaction mixture was diluted with ethyl acetate. The organic phase was washed with water and brine, dried over sodium sulfate, filtered and evaporated; 465 mg (quantitative yield) slightly yellow resin which was used without purification in the next step.

TLC (toluene/ethyl acetate 7:3): $R_f$=0.16;
HPLC: $Rt_{H1}$=0.93 min; ESIMS: 403, 405 [(M+H)$^+$, 1Br];
$^1$H-NMR (400 MHz, CDCl$_3$): δ 7.52 (dd, 1H), 7.38 (dd, 1H), 5.84 (s broad, 1H), 4.32 (dd, 1H), 4.02 (m, 1H), 3.81 (m, 1H), 2.05 (s, 3H), 1.31 (s, 9H).

g) (R)-3-Amino-3-(6-bromo-3-fluoro-pyridin-2-yl)-2,2-difluoro-butan-1-ol

To a solution of (R)-2-methyl-propane-2-sulfinic acid [(R)-1-(6-bromo-3-fluoro-pyridin-2-yl)-2,2-difluoro-3-hydroxy-1-methyl-propyl]amide (1.33 g, 3.30 mmol) in dioxane (26.6 ml) was added HCl/dioxane 4N (3.3 ml, 13.19 mmol). The reaction mixture was stirred for 21 hours at room temperature. The solvent was evaporated and to the residue was added ethyl acetate and crushed ice. The organic phase was extracted with water and was made alkaline with solid potassium carbonate. The aqueous phase was extracted with ethyl acetate, dried over sodium sulfate, filtered and evaporated. 930 mg colourless solid (94% yield).

TLC (toluene/ethyl acetate 7:3): $R_f$=0.25;
HPLC: $Rt_{H1}$=0.44 min; ESIMS: 299, 301 [(M+H)$^+$, 1Br];
$^1$H-NMR (400 MHz, DMSO-D$_6$): δ 7.73 (m, 2H, Ar), 7.29 (broad, 1H), 6.69 (broad s, 1H), 5.30 (t, 1H), 3.79 (m, 2H), 1.57 (d, 3H).

h) (R)-4-(6-Bromo-3-fluoro-pyridin-2-yl)-5,5-difluoro-4-methyl-5,6-dihydro-4H-[1,3]oxazine-2-ylamine A solution of (R)-3-amino-3-(6-bromo-3-fluoro-pyridin-2-yl)-2,2-difluoro-butan-1-ol (150 mg, 0.49 mmol) and bromocyan (106 mg, 1 mmol) in ethanol (5 ml) was heated for 19 h at 85° C. in a capped microwave vial. The solvent was evaporated and the residue was dissolved in ethyl acetate. The organic phase was washed with aq. ammonia, water and brine, dried over sodium sulfate, filtered and evaporated. The crude product (136 mg) was chromatographed over silica (toluene/ethyl acetate 1:1) to afford recovered starting material (27 mg) and the title compound: 64 mg (40% yield).

TLC (toluene/ethyl acetate 1:1): $R_f$=0.17;
HPLC: $Rt_{H1}$=0.56 min; ESIMS: 324, 326 [(M+H)$^+$, 1Br];
$^1$H-NMR (400 MHz, DMSO-D$_6$): δ 7.69 (m, 2H), 5.82 (broad s, 2H), 4.36 (m, 1H), 4.17 (m, 1H), 1.63 (s, 3H).

i) [(R)-4-(6-Bromo-3-fluoro-pyridin-2-yl)-5,5-difluoro-4-methyl-5,6-dihydro-4H-[1,3]oxazine-2-yl]-carbamic acid tert-butyl ester A solution of (R)-4-(6-bromo-3-fluoro-pyridin-2-yl)-5,5-difluoro-4-methyl-5,6-dihydro-4H-[1,3]oxazine-2-ylamine (60 mg, 0.185 mmol), Boc-anhydride (42.3 mg, 0.194 mmol) and Hünig's base (64.7 µl, 0.37 mmol) in dichloromethane (1.9 ml) was stirred at it for 3 days. The reaction mixture was diluted with ethyl acetate, washed with as Bicarbonate solution, water and brine, dried over sodium sulfate, filtered and evaporated. 76 mg (85% yield).

TLC (toluene/ethyl acetate 7:3): $R_f$=0.38;
HPLC: $Rt_{H1}$=1.08 min; ESIMS: 424, 426 [(M+H)$^+$, 1Br];
$^1$H-NMR (400 MHz, CDCl$_3$): δ 7.58-7.30 (m, 2H, Ar), 4.40-4.30 (m, 2H), 1.90 (broad s, 3H), 1.52 (s, 9H).

j) ((R)-4-{6-[(5-Cyano-3-methyl-pyridine-2-carbonyl)-amino]-3-fluoro-pyridin-2-yl}-5,5-difluoro-4-methyl-5,6-dihydro-4H-[1,3]oxazin-2-yl)-carbamic acid tert-butyl ester A degassed mixture of [(R)-4-(6-bromo-3-fluoro-pyridin-2-yl)-5,5-difluoro-4-methyl-5,6-dihydro-4H-[1,3]oxazine-2-yl]-carbamic acid tert-butyl ester (70 mg, 0.145 mmol), 5-cyano-3-methyl-pyridine-2-carboxylic acid amide (25.7 mg, 0.160 mmol), Xantphos (30.2 mg, 0.052 mmol), caesium carbonate (67.6 mg, 0.203 mmol) and Pd$_2$(dba)$_3$ (16.45 mg, 0.017 mmol) was heated under argon in dioxane (2.9 ml) at 60° C. for 5 hours. The reaction mixture (grey-brown suspension) was diluted with ethyl acetate and aq. bicarbonate solution and was then filtered. The filtrate was washed with water and brine, dried over sodium sulfate, filtered and evaporated. 166 mg brown solid. The crude product was chromatographed over silica gel (toluene/ethyl acetate 7:3) to give the title compound as a white solid. 28 mg (38% yield).

TLC (toluene/ethyl acetate 7:3): $R_f$=0.25;
HPLC: $Rt_{H1}$=1.18 min; ESIMS: 505 [(M+H)$^+$];
$^1$H-NMR (400 MHz, CDCl$_3$): δ 10.7 (broad s, 1H), 10.49 (broad s, 1H), 8.77 (d, 1H), 8.49 (broad d, 1H), 7.99 (d, 1H), 7.6 (broad t, 1H), 4.49-4.30 (m, 2H), 2.88 (s, 3H), 1.92 (broad s, 3H), 1.55 (s, 9H).

k) 5-Cyano-3-methyl-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide A solution of ((R)-4-{6-[(5-cyano-3-methyl-pyridine-2-carbonyl)-amino]-3-fluoro-pyridin-2-yl}-5,5-difluoro-4-methyl-5,6-dihydro-4H-[1,3]oxazin-2-yl)-carbamic acid tert-butyl ester (26 mg, 0.052 mmol) and TFA (200 µl, 2.6 mmol) in dichloromethane (1.3 ml) was stirred at it for 5 hours. The reaction mixture was evaporated and the residue diluted with aq. ammonia and ethyl acetate, washed with water and brine, dried over sodium sulfate, filtered and evaporated. 24 mg yellowish solid. Trituration with cyclohexane afforded the title compound as a slightly yellow solid. 17 mg (80% yield).

HPLC: $Rt_{H1}$=0.72 min; ESIMS: 405 [(M+H)$^+$];
$^1$H-NMR (400 MHz, DMSO-D$_6$): δ 10.71 (broad s, 1H, NH), 9.01 (broad s, 1H), 8.43 (broad s, 1H), 8.19 (broad d, 1H), 7.76 (t, 1H), 5.77 (broad s, 2H, NH$_2$), 4.32 (m, 2H), 2.61 (s, 3H), 1.67 (broad s, 3H).

Example 2

The compound listed in Table 1 was prepared by a procedure analogous to that used in Example 1.

TABLE 2

| Example | Compound | $^1$H-NMR ($\delta$; CDCl$_3$) | MS [m/z; (M + 1)$^+$] |
|---|---|---|---|
| 2 | 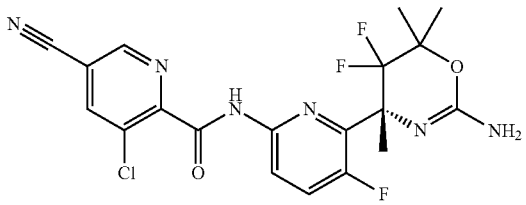<br>3-Chloro-5-cyano-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide | 10.15 (br. s, 1H), 8.85 (d, 1H), 8.39 (dd, 1H), 8.21 (d, 1H), 7.53 (dd, 1H), 4.22-4.14 (m, 2H), 1.84 (t, 3H) | LCMS: Rt$_{H1}$ = 0.67 min. [M + 1] = 425.0, 427.0 |

$^1$H-NMR (400 MHz, DMSO-d$_6$) $\delta$=7.83-7.70 (m, 2H), 6.10 (s, 1H), 5.48 (s, 1H), 1.93 (s, 3H), 1.23 (s, 3H), 1.18 (s, 9H), 1.07 (s, 3H).

Example 3

3-Chloro-5-cyano-pyridine-2-carboxylic acid [6-((R)-2-amino-5,5-difluoro-4,6,6-trimethyl-5,6-dihydro-4H-[1,3]oxazin-4-yl)-5-fluoro-pyridin-2-yl]-amide a) (R)-2-Methyl-propane-2-sulfinic acid [(R)-1-(6-bromo-3-fluoro-pyridin-2-yl)-2,2-difluoro-3-hydroxy-1,3-dimethyl-butyl]-amide To methylmagnesium chloride 3M in THF (38.3 ml, 115 mmol) was added a solution of (R)-3-(6-bromo-3-fluoro-pyridin-2-yl)-2,2-difluoro-3-((R)-2-methyl-propane-2-sulfinylamino)-butyric acid ethyl ester (5.12 g, 11.5 mmol, example 1e)) in THF (102 ml) at rt. After 2 hr stirring the reaction was quenched with addition of an aqueous ammonium chloride solution. The mixture was diluted with ethyl acetate and washed with water and brine, dried over sodium sulfate, filtered and evaporated. The crude product (4.78 g) was chromatographed over silica gel (cyclohexane/ethyl acetate 6:4) to give the title compound as a colourless solid. 2.97 g (59.9% yield).

TLC (cyclohexane/ethyl acetate 6:4, silica gel, UV 254): R$_f$=0.32;

LC-MS: Rt$_{H1}$=1.09 min; (100% pure; ESI+-MS: m/z 431 [(M+H)$^+$]);

b) (R)-4-(6-Bromo-3-fluoro-pyridin-2-yl)-5,5-difluoro-4,6,6-trimethyl-5,6-dihydro-4H-[1,3]oxazin-2-ylamine A solution of (R)-2-methyl-propane-2-sulfinic acid [(R)-1-(6-bromo-3-fluoro-pyridin-2-yl)-2,2-difluoro-3-hydroxy-1,3-dimethyl-butyl]-amide (2.95 g, 6.84 mmol) and cyanogen bromide (2.24 g, 20.52 mmol) in dry ethanol (68 ml) was sealed with a glass stopper and heated at 85° C. for 9 hr. The reaction solution was evaporated in vacuo and the crude product was taken up with ethyl acetate and 2M aq. ammonia. The organic phase was washed with water and brine, dried over sodium sulfate, filtered and evaporated. The crude product (2.74 g) was chromatographed over silica gel (toluene/ethyl acetate 6:4) to give the title compound as a colourless solid. 1.19 g (48.9% yield).

LC-MS: Rt$_{H1}$=67 min; (99% pure; ESI+-MS: m/z 352 [(M+H)$^+$], 354);

$^1$H-NMR (400 MHz, DMSO-d$_6$) $\delta$=7.72-7.59 (m, 2H), 5.83 (br. s, 2H), 1.67 (d, J=4.0 Hz, 3H), 1.48 (s, 3H), 1.27 (d, J=2.0 Hz, 3H).

c) [Bis-(4-methoxy-phenyl)-phenyl-methyl]-((R)-4-(6-bromo-3-fluoro-pyridin-2-yl)-5,5-difluoro-4,6,6-trimethyl-5,6-dihydro-4H-[1,3]oxazin-2-yl)-amine To a solution of (R)-4-(6-bromo-3-fluoro-pyridin-2-yl)-5,5-difluoro-4,6,6-trimethyl-5,6-dihydro-4H-[1,3]oxazin-2-ylamine (106 mg, 0.301 mmol) and triethylamine (60.9 mg, 0.602 mmol) in dichloromethane (3 ml) was added solid 4,4'-dimethoxytrityl chloride (112 mg, 0.331 mmol) under argon atmosphere. The green solution was stirred at rt for 2 hrs and was then evaporated in vacuo. The crude product was taken up with ethyl acetate and washed with aqueous sodium bicarbonate solution, water and brine. The organic phase was dried over sodium sulfate, filtered and evaporated. Filtration over silica gel (4.4 g, toluene/ethyl acetate 6:4) afforded the title compound as a blue-gray foam (202 mg, 96%).

TLC (toluene/ethyl acetate 6:4, silica gel, UV 254): R$_f$=0.60;

LC-MS: Rt$_{H1}$=1.22 min; (94% pure; ESI+-MS: m/z 654 [(M+H)$^+$]; 656);

$^1$H-NMR (400 MHz, DMSO-d$_6$) $\delta$=7.72-7.61 (m, 2H), 7.32-7.13 (m, 9H), 6.84-6.77 (m, 4H), 6.71 (br. s, 1H), 3.71 (s, 6H), 1.16 (br. s, 3H), 1.12 (br. s, 3H), 1.07 (br. s, 3H).

d) 3-Chloro-5-cyano-pyridine-2-carboxylic acid [6-((R)-2-{[bis-(4-methoxy-phenyl)-phenyl-methyl]-amino}-5,5-difluoro-4,6,6-trimethyl-5,6-dihydro-4H-[1,3]oxazin-4-yl)-5-fluoro-pyridin-2-yl]-amide A degassed mixture of [bis-(4-methoxy-phenyl)-phenyl-methyl]-[(R)-4-(6-bromo-3-fluoro-pyridin-2-yl)-5,5-difluoro-4,6,6-trimethyl-5,6-dihydro-4H-[1,3]oxazin-2-yl]-amine (196 mg, 0.299 mmol), 5-cyano-3-methyl-pyridine-2-carboxylic acid amide (59.8 mg, 0.329 mmol), Xantphos (62.4 mg, 0.108 mmol), caesium carbonate (139 mg, 0.419 mmol) and $Pd_2(dba)_3$ (33.9 mg, 0.036 mmol) was heated under argon in dioxane (6 ml) at 60° C. for 20 hours. The reaction mixture was diluted with ethyl acetate and aq. bicarbonate solution and was then filtered through hyflo. The filtrate was washed with water and brine, dried over sodium sulfate, filtered and evaporated to give 226 mg yellowish foam. The crude product was chromatographed over silica gel (toluene/ethyl acetate 8:2) to give the title compound as a light yellow foam. 92 mg (38.6% yield).

LC-MS: $Rt_{H1}$=1.20 min (95% pure; ESI+-MS: 755, [(M+H)$^+$]; 756, 757, 758);

$^1$H-NMR (400 MHz, CDCl3): δ 10.24 (br. s, 1 NH), 8.74 (br. d, 1H), 8.36 (dd, 1H), 8.21 (d, J=1.8 Hz, 1H), 7.50 (dd, 1H), 7.42-6.79 (m, 13H+1NH), 3.79 (s, 6H), 1.60 (br. s, 3H), 0.89 (br. s, 3H), 0.78 (br. s, 3H).

e) 3-Chloro-5-cyano-pyridine-2-carboxylic acid [6-((R)-2-amino-5,5-difluoro-4,6,6-trimethyl-5,6-dihydro-4H-[1,3]oxazin-4-yl)-5-fluoro-pyridin-2-yl]-amide A solution of 3-chloro-5-cyano-pyridine-2-carboxylic acid [6-((R)-2-{[bis-(4-methoxy-phenyl)-phenyl-methyl]-amino}-5,5-difluoro-4,6,6-trimethyl-5,6-dihydro-4H-[1,3]oxazin-4-yl)-5-fluoro-pyridin-2-yl]-amide (85 mg, 0.113 mmol), TFA (572 µl, 7.43 mmol) and triethylsilane (54 µl, 0.338 mmol) in dichloromethane (1.1 ml) was stirred at rt for 24 hours. The reaction mixture was evaporated and the residue diluted with ethyl acetate, washed with water and brine, dried over sodium sulfate, filtered and evaporated to give 119 mg brown-yellowish resin. The product was chromatographed over silica gel (RediSep 12 g, conditioned with ethyl acetate/methanol 95:5 and eluted with ethyl acetate) to give the title compound as a light yellow solid. 38 mg (74.6% yield).

TLC (ethyl acetate/methanol 95:5, silica gel, UV 254): $R_f$=0.29;

LC-MS: $Rt_{H1}$=0.76 min (100% pure; ESI+-MS: 453, [(M+H)$^+$], 455);

$^1$H-NMR (400 MHz, CDCl3): δ 12.66 (very br. s, 1 NH), 12.03 (br. s, 1 NH), 10.29 (br. s, 1 NH), 8.87 (d, J=1.8 Hz, 1H), 8.49 (dd, 1H), 8.18 (d, J=1.8 Hz, 1H), 7.62 (dd, 1H), 5.74 (br. s, 1 NH), 2.01 (d, J=2.3 Hz, 3H), 1.74 (s, 3H), 1.44 (d, J=2.3 Hz, 3H).

Example 4

5-Cyano-3-methyl-pyridine-2-carboxylic acid {6-[(R)-2-amino-5,5-difluoro-4-(2-methoxy-ethyl)-5,6-dihydro-4H-[1,3]oxazin-4-yl]-5-fluoro-pyridin-2-yl}-amide

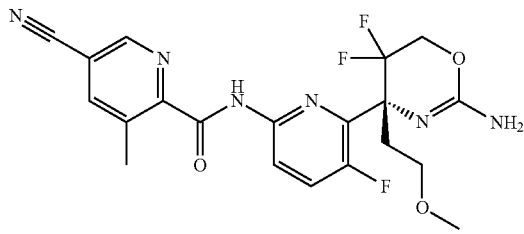 [SMILES: COCC[C@]1(c2nc(NC(=O)c3ncc(C#N)cc3C)ccc2F)N=C(N)OCC1(F)F]

a) 1-(6-Bromo-3-fluoro-4-triethylsilanyl-pyridin-2-yl)-3-methoxy-propan-1-one

To a solution of 1-(6-bromo-3-fluoro-4-triethylsilanyl-pyridin-2-yl)-ethanone (11.6 g, 33.9 mmol, example 1, step b) in dichloromethane (50 ml) was added Hünigs-base (6.21 ml, 35.6 mmol) at 0° C. followed by TMS-triflate (6.43 ml, 35.52 mmol, 1.05 eq.) under nitrogen. The reaction mixture was stirred at 0° C. for 40 minutes. Dimethoxymethane (2.71 g, 35.6 mmol) and 2,6-di-tert-butylpyridine (0.648 g, 3.39 mmol) was added drop wise at 0° C. TMS-triflate (0.61 ml, 3.39 mmol) was then added to the reaction mixture. After 30 min the cooling bath was removed and stirring was continued at rt over night (18 h). The reaction mixture was poured onto cold brine, diluted with ethyl acetate and the organic phase was washed thoroughly with 10% $NaHSO_4$ solution, sat. sodium bicarbonate solution (saturated with NaCl) and brine, dried over sodium sulfate, filtered and evaporated. The crude product (13.52 g) was chromatographed over silica gel (320 g, cyclohexane/ethyl acetate 95:5) to give the title compound as a yellow liquid: 9.18 g (72% yield).

TLC (cyclohexane/ethyl acetate 5:1): $R_f$=0.61;

LC-MS: $Rt_{H1}$=1.43 min (100% pure; ESI+-MS: 376, [(M+H)$^+$], 378);

$^1$H-NMR (400 MHz, CDCl$_3$): δ 7.58 (d, J=2.9 Hz, 1H), 3.83 (t, J=6.2 Hz, 2H), 3.41 (t, J=6.2 Hz, 2H), 3.39 (s, 3H), 1.06-0.82 (m, 15H).

b) (S)-2-Methyl-propane-2-sulfinic acid [1-(6-bromo-3-fluoro-4-triethylsilanyl-pyridin-2-yl)-3-methoxy-prop-(E)-ylidene]-amide A mixture of titantetraethoxide (11.03 g, 48.4 mmol), (S)-tert.-butylsulfinamide (3.52 g, 29 mmol) and 1-(6-Bromo-3-fluoro-4-triethylsilanyl-pyridin-2-yl)-3-methoxy-propan-1-one (9.1 g, 24.18 mmol) in THF (100 ml) was stirred at 60° C. under a nitrogen atmosphere for 34 hours. The cold reaction mixture was diluted with ethyl acetate and poured onto ice-cold brine (200 ml) with gentle stirring. The precipitate was filtered through a pad of hyflo and washed with ethyl acetate. The filtrate was diluted with ethyl acetate and washed with brine, dried over sodium sulfate, filtered and evaporated. The crude yellowish-brown oil (10.67 g) was chromatographed over silica gel (Redisep column 120 g, cyclohexane/ethyl acetate 95:5) to give the title compound as a yellow-orange oil. 7.51 g (63.5% yield).

TLC (cyclohexane/ethyl acetate 10:1): $R_f$=0.23;

LC-MS: $Rt_{H1}$=1.53 min (98%, ESI+-MS: m/z 479 [(M+H)$^+$, 1Br], 481).

c) (R)-3-(6-Bromo-3-fluoro-4-triethylsilanyl-pyridin-2-yl)-2,2-difluoro-5-methoxy-3-((S)-2-methyl-propane-2-sulfinylamino)-pentanoic acid ethyl ester To a suspension of zinc (3.07 g, 47 mmol) and copper(I) chloride (233 mg, 2.349 mmol) in dry THF (90 ml) were added 4 drops of trimethylchlorosilane under nitrogen to activate the zinc. After 10 minutes ethyl 2-bromo-2,2-difluoroacetate (9.54 g, 47 mmol) was added slowly by syringe over a period of 20 minutes between 25° and 30° C. adjusted with an external cooling bath (exothermic). The reaction mixture was kept in an ultrasound bath for 30 minutes. This black fine suspension was added drop wise to a solution of (S)-2-methyl-propane-2-sulfinic acid [1-(6-bromo-3-fluoro-4-triethylsilanyl-pyridin-2-yl)-3-methoxy-prop-(E)-ylidene]-amide (7.51 g, 15.66 mmol) in dry THF (75 ml) at 0° C. under inert atmosphere. After 15 min the reaction mixture was kept at 50° C. for 2 h and was then added to a cold aq. ammonium chloride solution (5%). Ethyl acetate was added and the organic phase was washed with aq. citric acid (5% solution), water, sat. sodium bicarbonate solution and brine, dried over sodium sulfate, filtered and concentrated. The crude yellowish oil (9.77 g, roughly a 4:1 mixture of diastereoisomers) was chromatographed over silica gel (Redisep column 120 g, cyclohexane/ethyl acetate 85:15) to give the title compound as a yellow oil. 6.11 g yellow oil. (64.6% yield).

TLC (cyclohexane/ethyl acetate 2:1): $R_f$=0.47;
LC-MS: $Rt_{H1}$=1.54 min (100%, ESI+–MS: m/z 604 [(M+H)$^+$, 1Br], 606);
$^1$H-NMR (400 MHz, CDCl$_3$): δ 7.45 (d, J=2.5 Hz, 1H), 6.63 (br. s, 1H), 4.22-4.04 (m, 2H), 3.77-3.68 (m, 1H), 3.31-3.20 (m, 1H), 3.15 (s, 3H), 3.11-3.00 (m, 1H), 2.97-2.84 (m, 1H), 1.35 (s, 9H), 1.15 (t, J=7.2 Hz, 3H), 1.04-0.95 (m, 9H), 0.94-0.83 (m, 6H).

The minor diastereoisomer $R_f$=0.35 (2:1 cyclohexane: ethyl acetate was not isolated.

d) (R)-3-(6-Bromo-3-fluoro-pyridin-2-yl)-2,2-difluoro-5-methoxy-3-((S)-2-methyl-propane-2-sulfinylamino)-pentanoic acid ethyl ester Freshly ground KF (1.174, 20.21 mmol) was added to a solution of (R)-3-(6-bromo-3-fluoro-4-triethylsilanyl-pyridin-2-yl)-2,2-difluoro-5-methoxy-3-((S)-2-methyl-propane-2-sulfinylamino)-pentanoic acid ethyl ester (6.10 g, 10.11 mmol) and acetic acid (1.157 ml, 20.21 mmol) in THF (39.8 ml). DMF (39.8 ml) was added and the suspension was stirred at rt. After 6 h the reaction mixture was diluted with ethyl acetate and washed with sat. sodium bicarbonate solution and brine, dried over sodium sulfate, filtered and evaporated. The crude product (4.85 g, 98% yield) was used without purification in the next step.

TLC (cyclohexane/ethyl acetate 1:1): $R_f$=0.33;
LC-MS: $Rt_{H1}$=1.11 min (100%, ESI+–MS: m/z 489 [(M+H)$^+$, 1Br], 491);
$^1$H-NMR (400 MHz, CDCl$_3$): δ 7.56-7.48 (m, 1H), 7.41-7.30 (m, 1H), 6.54 (br. s, 1H), 4.25-4.05 (m, 2H), 3.77-3.64 (m, 1H), 3.34-3.22 (m, 1H), 3.15 (s, 3H), 3.08-2.97 (m, 1H), 2.94-2.86 (m, 1H), 1.34 (s, 9H), 1.18 (t, J=7.3 Hz, 3H).

e) (S)-2-Methyl-propane-2-sulfinic acid [(R)-1-(6-bromo-3-fluoro-pyridin-2-yl)-2,2-difluoro-3-hydroxy-1-(2-methoxy-ethyl)-propyl]-amide To a solution of (R)-3-(6-bromo-3-fluoro-pyridin-2-yl)-2,2-difluoro-5-methoxy-3-((S)-2-methyl-propane-2-sulfinylamino)-pentanoic acid ethyl ester (2.4 g, 4.90 mmol) in THF (38 ml) was added lithiumborohydride (214 mg, 9.81 mmol) in 2 portions. The slightly exothermic reaction was stirred for 6 hours at room temperature. Crushed ice was added carefully and the reaction mixture was diluted with ethyl acetate. The organic phase was washed with water and brine, dried over sodium sulfate, filtered and evaporated. The crude yellowish resin (2.05 g) was chromatographed over silica gel (Redisep column 40 g, cyclohexane/ethyl acetate 4:6) to give the title compound as a colourless resin. 1.50 g (68.4% yield).

TLC (cyclohexane/ethyl acetate 1:1): $R_f$=0.13;
LC-MS: $Rt_{H1}$=0.84 min (100%, ESI+–MS: m/z 447 [(M+H)$^+$, 1Br], 449);
$^1$H-NMR (400 MHz, CDCl$_3$): δ 7.55-7.45 (m, 1H), 7.37-7.29 (m, 1H), 6.34-6.25 (br. s, 1H), 3.95-3.63 (m, 2+1H), 3.40-3.27 (m, 1H), 3.18 (s, 3H), 3.05-2.94 (m, 1H), 2.84-2.73 (m, 1H), 2.19-2.11 (m, 1H, OH), 1.35 (s, 9H).

f) (R)-3-Amino-3-(6-bromo-3-fluoro-pyridin-2-yl)-2,2-difluoro-5-methoxy-pentan-1-ol To a solution of (S)-2-methyl-propane-2-sulfinic acid [(R)-1-(6-bromo-3-fluoro-pyridin-2-yl)-2,2-difluoro-3-hydroxy-1-(2-methoxy-ethyl)-propyl]amide (1.50 g, 3.33 mmol) in methanol (8.4 ml) was added 2M HCl in diethyl ether (6.56 ml, 13.11 mmol). The reaction mixture was stirred for 1.5 h at room temperature. 7 M ammonia in methanol (2.7 ml) was added to the reaction mixture and the resulting colourless suspension was evaporated in vacuo. The remaining solid was triturated with warm dichloromethane, cooled to rt, filtered and rinsed with dichloromethane. The filtrate was evaporated affording the title compound which was used without purification in the next step. 1.42 g colourless, viscous oil. 100% yield.

TLC (cyclohexane/ethyl acetate 4:6): $R_f$=0.41;
LC-MS: $Rt_{H1}$=0.52 min (100%, ESI+–MS: m/z 343 [(M+H)$^+$, 1Br], 345);
$^1$H-NMR (400 MHz, CDCl$_3$): δ 7.52 (dd, J=3.1, 8.4 Hz, 1H), 7.34 (dd, J=8.4, 9.9 Hz, 1H), 4.23-4.06 (m, 1H), 3.81 (s, 1H+OH), 3.66-3.56 (m, 1H), 3.30-3.21 (m, 1H), 3.17 (s, 3H), 2.77-2.66 (m, 1H), 2.57-2.43 (m, 1H).

g) N—[(R)-4-(6-Bromo-3-fluoro-pyridin-2-yl)-5,5-difluoro-4-(2-methoxy-ethyl)-5,6-dihydro-4H-[1,3]oxazin-2-yl]-4-nitro-benzamide To a solution of (R)-3-amino-3-(6-bromo-3-fluoro-pyridin-2-yl)-2,2-difluoro-5-methoxy-pentan-1-ol (1.15 g, 3.35 mmol) in THF (27.9 ml) was added nitrobenzoyl-isothiocyanate (767 mg, 3.69 mmol). After stirring at rt for 4 hr DCC (760 mg, 3.69 mmol) and triethylamine (34.1 mg, 0.337 mmol) was added. Stirring was continued at rt for 19 hr and finally, the reaction mixture was kept at 70° C. for 5 h. The yellow-orange solution was cooled and evaporated in vacuo. The crude product (2.7 g) was chromatographed over silica gel (Redisep column 120 g, cyclohexane/ethyl acetate 7:3) to give the title compound as a light yellow foam. 650 mg (35.6% yield).

TLC (cyclohexane/ethyl acetate 7:3): $R_f$=0.17;
LC-MS: $Rt_{H1}$=1.15 min (95%, ESI+–MS: m/z 517 [(M+H)$^+$, 1Br], 519);
$^1$H-NMR (400 MHz, CDCl$_3$): δ 12.07 (br. s, 1H), 8.49 (d, J=9.0 Hz, 2H), 8.29 (d, J=8.9 Hz, 2H), 7.68-7.58 (m, 1H), 7.49-7.40 (m, 1H), 4.59-4.42 (m, 1H), 4.35-4.19 (m, 1H), 3.87-3.72 (m, 1H), 3.54-3.39 (m, 1H), 3.35 (s, 3H), 3.02-2.88 (m, 1H), 2.71-2.57 (m, 1H).

h) (R)-4-(6-Bromo-3-fluoro-pyridin-2-yl)-5,5-difluoro-4-(2-methoxy-ethyl)-5,6-dihydro-4H-[1,3]oxazin-2-ylamine A suspension of N—[(R)-4-(6-bromo-3-fluoro-pyridin-2-yl)-5,5-difluoro-4-(2-methoxy-ethyl)-5,6-dihydro-4H[1,3]oxazin-2-yl]-4-nitro-benzamide (640 mg, 1.237 mmol) and potassium carbonate (513 mg, 3.71 mmol) in methanol (18.7 ml) was stirred for 22 h at rt. The resulting yellow solution was evaporated, diluted with ethyl acetate and washed with water and brine, dried over sodium sulfate, filtered and evaporated. 400 mg yellow solid (88% yield). The crude product was used in the next step without purification.

TLC (cyclohexane/ethyl acetate 1:1): $R_f$=0.14;
LC-MS: $Rt_{H1}$=0.59 min (100%, ESI+–MS: m/z 368 [(M+H)$^+$, 1Br], 370);
$^1$H-NMR (400 MHz, CDCl$_3$): δ 7.53-7.43 (m, 1H), 7.28 (s, 1H), 4.35-4.18 (m, 1H), 4.14-4.01 (m, 1H), 3.71-3.62 (m, 1H), 3.53-3.40 (m, 1H), 3.30 (s, 3H), 3.26-3.10 (m, 1H), 3.05-2.93 (m, 1H), 2.32-2.14 (br. s, 1H, NH), 1.77-1.47 (br. s, 2H, NH plus res. water).

i) [Bis-(4-methoxy-phenyl)-phenyl-methyl]-[(R)-4-(6-bromo-3-fluoro-pyridin-2-yl)-5,5-difluoro-4-(2-methoxy-ethyl)-5,6-dihydro-4H-[1,3]oxazin-2-yl]-amine To a solution of (R)-4-(6-bromo-3-fluoro-pyridin-2-yl)-5,5-difluoro-4-(2-methoxy-ethyl)-5,6-dihydro-4H-[1,3]oxazin-2-ylamine (200 mg, 0.543 mmol) and triethylamine (110 mg, 1.087 mmol) in dichloromethane (5.4 ml) was added solid 4,4'-dimethoxytrityl chloride (202 mg, 0.598 mmol) under argon atmosphere. The green solution was stirred at rt for 16 hrs and was then evaporated in vacuo. The crude product was taken up with ethyl acetate and washed with aqueous citric acid, aqueous sodium bicarbonate solution, water and brine. The organic phase was dried over sodium sulfate, filtered and evaporated. The crude product (380 mg) was chromatographed over silica gel (Redisep column 12 g, cyclohexane/ethyl acetate 8:2) to give the title compound as a colourless foam. 339 mg (93% yield).

TLC (cyclohexane/ethyl acetate 8:2): $R_f$=0.29;
LC-MS: $Rt_{H1}$=1.23 min (100%, ESI+−MS: m/z 670 [(M+H)$^+$, 1Br], 672);
$^1$H-NMR (400 MHz, CDCl$_3$): δ 7.49-7.16 (m, 11H), 6.87-6.78 (m, 4H), 5.41-5.28 (m, 1H), 3.87-3.59 (m, 9H), 3.07 (m, 4H), 2.99-2.85 (m, 1H), 2.74-2.60 (m, 1H).

j) 5-Cyano-3-methyl-pyridine-2-carboxylic acid {6-[(R)-2-{[bis-(4-methoxy-phenyl)-phenyl-methyl]-amino}-5,5-difluoro-4-(2-methoxy-ethyl)-5,6-dihydro-4H-[1,3]oxazin-4-yl]-5-fluoro-pyridin-2-yl}-amide A degassed mixture of [bis-(4-methoxy-phenyl)-phenyl-methyl]-[(R)-4-(6-bromo-3-fluoro-pyridin-2-yl)-5,5-difluoro-4-(2-methoxy-ethyl)-5,6-dihydro-4H-[1,3]oxazin-2-yl]-amine (330 mg, 0.492 mmol), 5-cyano-3-methyl-pyridine-2-carboxylic acid amide (95 mg, 0.591 mmol), rac-trans-N,N'-dimethylcyclohexane-1,2-diamine (21.65 mg, 0.148 mmol), potassium carbonate (150 mg, 1.083 mmol) and copper iodide (28.1 mg, 0.148 mmol) was refluxed under argon in dioxane (12.3 ml) for 20 hrs. The reaction mixture was evaporated, taken up in ethyl acetate and washed with aqueous sodium bicarbonate solution, water and brine, dried over sodium sulfate, filtered and evaporated to give 406 mg red-brown foam. The crude product was chromatographed over silica gel (Redisep column 12 g, toluene/ethyl acetate 8:2) to give the title compound as a pinky foam. 152 mg (37.4% yield).

TLC (toluene/ethyl acetate 8:2): $R_f$=0.37;
LC-MS: $Rt_{H1}$=1.22 min (91% pure; ESI+−MS: 751).

k) 5-Cyano-3-methyl-pyridine-2-carboxylic acid {6-[(R)-2-amino-5,5-difluoro-4-(2-methoxy-ethyl)-5,6-dihydro-4H-[1,3]oxazin-4-yl]-5-fluoro-pyridin-2-yl}-amide A solution of 5-cyano-3-methyl-pyridine-2-carboxylic acid {6-[(R)-2-{[bis-(4-methoxy-phenyl)-phenyl-methyl]amino}-5,5-difluoro-4-(2-methoxy-ethyl)-5,6-dihydro-4H-[1,3]oxazin-4-yl]-5-fluoro-pyridin-2-yl}-amide (146 mg, 0.194 mmol), TFA (0.989 ml, 12.83 mmol) and triethylsilane (0.093 ml, 0.583 mmol) in dichloromethane (1.9 ml) was stirred at it for 18 hours. The reaction mixture was evaporated and the residue diluted with ethyl acetate, washed with sat. aqueous sodium bicarbonate solution, water and brine, dried over sodium sulfate, filtered and evaporated. 142 mg colourless resin. The product was chromatographed over a preparative silica gel plate (2 mm, 20×20 cm, Merck, dichloromethane/methanol 95:5) to give the title compound as a colourless foam. 74 mg (85% yield).

TLC (dichloromethane/methanol 95:5, silica gel, UV 254): $R_f$=0.28;
LC-MS: $Rt_{H1}$=0.76 min (100% pure; ESI+−MS: 449 [(M+H)$^+$]);
$^1$H-NMR (400 MHz, DMSO-d$_6$): δ=10.70 (br. s, 1H, NH), 9.00 (br. s, 1H), 8.45 (br. s, 1H), 8.30-8.13 (m, 1H), 7.84-7.66 (m, 1H), 5.88 (br. s, 3H), 4.45-4.25 (m, 1H), 4.19-4.00 (m, 1H), 3.62-3.44 (m, 1H), 3.27-3.18 (m, 1H), 3.16 (s, 3H), 2.96-2.83 (m, 1H), 2.61 (s, 3H), 2.00-1.88 (m, 1H).

Examples 5-6

The compounds listed in Table 3 were prepared by a procedure analogous to that used in Example 4. However, for Example 5 (R)-tert.-butylsulfinamide was used to form the sulfoximine in step 4b.

TABLE 3

| Example | Compound | $^1$H-NMR (solvent; δ) | MS [m/z; (M + 1)$^+$] |
|---|---|---|---|
| 5 | 5-Cyano-3-methyl-pyridine-2-carboxylic acid {6-[(S)-2-amino-5,5-difluoro-4-(2-methyl-ethyl)-5,6-dihydro-4H-[1,3]oxazin-4-yl]-5-fluoro-pyridin-2-yl}-amide | (400 MHz, CDCl$_3$): δ 10.69 (br. s, 1H), 8.92-8.82 (m, 1H), 8.55-8.43 (m, 1H), 7.96-7.87 (m, 1H), 7.68-7.58 (m, 1H), 4.61-4.45 (m, 1H), 4.31-4.17 (m, 1H), 3.65-3.56 (m, 2H), 3.32 (s, 3H), 3.01-2.88 (m, 1H), 2.81 (s, 3H), 2.58-2.43 (m, 1H) | LCMS: $Rt_{H3}$ = 0.75 [M + 1] = 449 |

TABLE 3-continued

| Example | Compound | $^1$H-NMR (solvent; δ) | MS [m/z; (M + 1)$^+$] |
|---|---|---|---|
| 6 | 3-Chloro-5-trifluoromethyl-pyridine-2-carboxylic acid {6-[(R)-2-amino-5,5-difluoro-4-(2-methoxy-ethyl)-5,6-dihydro-4H-[1,3]oxazin-4-yl]-5-fluoro-pyridin-2-yl}-amide | (400 MHz, CDCl$_3$): δ 10.47 (br. s, 1H), 8.82 (s, 1H), 8.41 (dd, 1H), 8.06 (s, 1H), 7.49 (t, 1H), 4.25-4.33 (d, 1H), 3.97-4.20 (m, 1H), 3.42-3.56 (m, 2H), 3.19 (s, 3H), 2.78-2.92 (m, 1H), 2.15-2.31 (m, 1H) | LCMS: Rt$_{H2}$ = 0.81 [M + 1] = 514.0 |

Example 7

3-Chloro-5-trifluoromethyl-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide

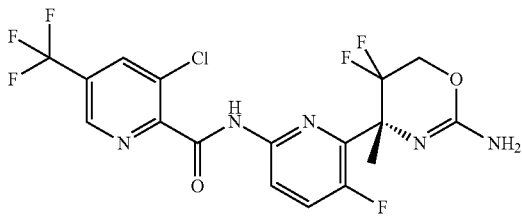 [SMILES: C[C@]1(c2nc(NC(=O)c3ncc(C(F)(F)F)cc3Cl)ccc2F)N=C(N)OCC1(F)F]

a) [Bis-(4-methoxy-phenyl)-phenyl-methyl]-[(R)-4-(6-bromo-3-fluoro-pyridin-2-yl)-5,5-difluoro-4-methyl-5,6-dihydro-4H-[1,3]oxazin-2-yl]-amine (R)-4-(6-bromo-3-fluoro-pyridin-2-yl)-5,5-difluoro-4-methyl-5,6-dihydro-4H-[1,3]oxazine-2-ylamine (5 g, 15.43 mmol, Example 1 intermediate h) was dissolved in DCM (154 ml) under argon, triethylamine (4.30 mL, 30.9 mmol) and 4,4'-dimethoxytrityl chloride (5.75 g, 16.97 mmol) were added and the reaction mixture was stirred at rt for 18 hours. The solvent was removed in vacuo and the residue was taken up in ethyl acetate. The organic layer was washed with aq 10% citric acid, water, aqueous saturated sodium bicarbonate solution and brine, dried over sodium sulfate, filtered and concentrated. The crude product was chromatographed over silica gel (Redisep column 120 g, cyclohexane/ethyl) to give the title compound: 8.16 g (69.2% yield).

TLC (cyclohexane/ethyl acetate 3:1, silica gel, UV 254): R$_f$=0.45;

LC-MS: Rt$_{H2}$=1.37 min; (ESI+-MS: m/z 626 [(M+H)$^+$, 1Br]; 628);

$^1$H-NMR (400 MHz, DMSO-d$_6$): δ 7.71 (dd, 1H), 7.64 (dd, 1H), 7.32-7.08 (m, 9H), 6.86 (s, 1H), 6.81-6.77 (m, 4H), 4.07-4.05 (m, 1H), 4.02-3.98 (m, 1H), 3.71 (s, 6H), 1.05 (br. s., 3H).

b) [(R)-4-(6-Amino-3-fluoro-pyridin-2-yl)-5,5-difluoro-4-methyl-5,6-dihydro-4H-[1,3]oxazin-2-yl]-[bis-(4-methoxy-phenyl)-phenyl-methyl]-amine To a solution of [bis-(4-methoxy-phenyl)-phenyl-methyl]-[(R)-4-(6-bromo-3-fluoro-pyridin-2-yl)-5,5-difluoro-4-methyl-5,6-dihydro-4H-[1,3]oxazin-2-yl]-amine (23.4 g, 28.8 mmol) in ammonia (173 ml, 1.21 mol, 7M in methanol) in a microwave vial was added ethylene glycol (240 ml) and methanol (240 ml). Copper oxide Cu$_2$O (1.21 g, 8.46 mmol) was added and the vial was sealed. The reaction mixture was stirred at 80° C. for 43 hours. The cold reaction mixture was diluted with ethyl acetate and washed with water, aqueous ammonia and brine. The organic layer was dried over sodium sulfate, filtered and evaporated. The crude product was chromatographed over silica gel (400 g, dichloromethane/methanol 98:2+0.2% ammonia) to give the title compound: 4.29 g (25% yield).

TLC (dichloromethane/methanol 95:5+0.5% ammonia, silica gel, UV 254): R$_f$=0.29;

LC-MS: Rt$_{H2}$=1.03 min; (ESI+-MS: m/z 563 [(M+H)$^+$]);

$^1$H-NMR (400 MHz, DMSO-d$_6$): δ 7.25-7.32 (m, 2H) 7.10-7.24 (m, 8H) 6.77 (d, 4H) 6.59 (s, 1H) 6.41 (dd, 1H) 5.77 (d, 2H) 4.09-4.22 (m, 1H) 3.91-4.01 (m, 1H) 3.70 (s, 6H) 0.97 (br. s., 3H).

c) 3-Chloro-5-trifluoromethyl-pyridine-2-carboxylic acid [6-((R)-5,5-difluoro-2-{[(4-methoxy-phenyl)-(3-methoxy-phenyl)-phenyl-methyl]-amino}-4-methyl-5,6-dihydro-4H-[1,3]oxazin-4-yl)-5-fluoro-pyridin-2-yl]-amide

[(R)-4-(6-amino-3-fluoro-pyridin-2-yl)-5,5-difluoro-4-methyl-5,6-dihydro-4H-[1,3]oxazin-2-yl]-[bis-(4-methoxy-phenyl)-phenyl-methyl]-amine (250 mg, 0.444 mmol), 3-chloro-5-(trifluoromethyl)-picolinic acid (120 mg, 0.533 mmol) and HOAt (109 mg, 0.800 mmol) were dissolved in DMF (4.44 ml) under argon. EDCxHCl (128 mg, 0.667 mmol) was added and the reaction mixture was stirred at it for 18 hours. The reaction mixture was diluted with ethyl acetate, washed with water and brine, dried over sodium sulfate, filtered and concentrated. The crude product was chromatographed over silica gel (Redisep column 12 g, cyclohexane/ethyl acetate) to give the title compound: 100 mg (29.2% yield).

LC-MS: Rt$_{H2}$=1.43 min; (96% purity; ESI+-MS: m/z 770 [(M+H)$^+$, 1Cl]; 772);

¹H-NMR (400 MHz, DMSO-d$_6$): δ 11.22 (s, 1H), 9.08 (s, 1H), 8.72 (s, 1H), 8.16 (dd, 1H), 7.71 (dd, 1H), 7.30-7.24 (m, 2H), 7.23-7.10 (m, 7H), 6.81-6.74 (m, 5H), 4.33-4.23 (m, 1H), 4.08-4.00 (m, 1H), 3.70 (s, 6H), 1.06 (br. s, 3H).

d) 3-Chloro-5-trifluoromethyl-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide 3-Chloro-5-trifluoromethyl-pyridine-2-carboxylic acid [6-((R)-5,5-difluoro-2-{[(4-methoxy-phenyl)-(3-methoxy-phenyl)-phenyl-methyl]-amino}-4-methyl-5,6-dihydro-4H-[1,3]oxazin-4-yl)-5-fluoro-pyridin-2-yl]-amide (80 mg, 0.104 mmol) was dissolved in dichloromethane (0.1039 ml), TFA (80.0 µl, 1.04 mmol) was added and the reaction mixture was stirred at rt for 18 hours. The reaction mixture was poured onto a mixture of ice ethyl acetate and NH$_4$OH (w=25%). The organic layer was washed with water, brine, dried over sodium sulfate, filtered and concentrated. The crude product was chromatographed over silica gel (column 4 g, dichloromethane/methanol 95:5+0.5% ammonia) to give the title compound: 32 mg (65.9% yield).

LC-MS: Rt$_{H1}$=0.79 min; (100% purity; ESI+-MS: m/z 468 [(M+H)$^+$, 1Cl]; 470);
¹H-NMR (400 MHz, CDCl$_3$): δ 10.21 (br. s, 1H), 8.86 (d, 1H), 8.40 (dd, 1H), 8.17 (d, 1H), 7.53 (dd, 1H), 4.21-4.13 (m, 4H), 1.83 (t, 3H).

Example 7a

Alternative synthesis of 3-chloro-5-trifluoromethyl-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide a) (R)-4-(6-Bromo-3-fluoro-pyridin-2-yl)-5,5-difluoro-4-methyl-5,6-dihydro-4H-[1,3]oxazin-2-ylamine The (+)-campher sulfonic acid salt of (R)-3-amino-3-(6-bromo-3-fluoro-pyridin-2-yl)-2,2-difluoro-butan-1-ol (12.75 g, 23.99 mmol) was partitioned between TBME and aq. Na$_2$CO$_3$ (w=10%), the layers were separated, the aq. layer was extracted with TBME, the organic layer was extracted with sat. aq. NaCl. The combined organic layers were dried with Na$_2$CO$_3$, the solvent evaporated to yield the free base as white crystals.

To a solution of (R)-3-amino-3-(6-bromo-3-fluoro-pyridin-2-yl)-2,2-difluoro-butan-1-ol (9.49 g, 31.7 mmol) in EtOH (256 ml) was added NaHCO$_3$ (1.066 g, 12.69 mmol) and cyanogen bromide (10.08 g, 95 mmol) and the mixture was warmed to 85° C. over night. After cooling to rt the solvent was evaporated and the residue taken up in 1N HCl and TBME, the layers were separated and the organic layer was washed with 1N HCl. The aq. layers were combined, basified by addition of solid Na$_2$CO$_3$ and extracted with TBME (2×). The combined TBME extracts were washed with sat. aq. NaCl, dried with K$_2$CO$_3$ to provide the desired product as yellow resin. This material was used for the next step without further purification.

HPLC: Rt$_{H5}$=2.716 min; ESIMS [M+H]$^+$=324.0/326.0;
¹H-NMR (600 MHz, DMSO-d$_6$): δ 7.76-7.59 (m, 2H), 5.85 (s, 2H), 4.43-4.30 (m, 1H), 4.24-4.10 (m, 1H), 1.63 (br. s, 3H).

b) (R)-4-(6-Amino-3-fluoro-pyridin-2-yl)-5,5-difluoro-4-methyl-5,6-dihydro-4H-[1,3]oxazin-2-ylamine To a solution of (R)-4-(6-bromo-3-fluoro-pyridin-2-yl)-5,5-difluoro-4-methyl-5,6-dihydro-4H-[1,3]oxazin-2-ylamine (8.73 g, 23.17 mmol) in ethylene glycol (139 ml) and aq. NH$_3$ (w=25%, 108 ml) in an autoclave was added copper(I) oxide (497 mg, 3.47 mmol) and the mixture was warmed to 60° C. over night. After cooling to rt the mixture was extracted with EtOAc, the organic layer was washed with aq. NH$_3$ (w=12%, 2×), the combined organic layers were washed with sat. aq. NaCl, dried with Na$_2$SO$_4$ and evaporated. The residue was dissolved in TBME and extracted with 1N HCl (2×). The combined aq. layers were basified by addition of solid Na$_2$CO$_3$ some NaCl was added and the aq. solution extracted with DCM (4×). The combined DCM extracts were dried with K$_2$CO$_3$ and evaporated to provide the title compound as greyish resin. The crude material was used for the next step without further purification.

HPLC: Rt$_{H5}$=2.584 min; ESIMS [M+H]$^+$=261.0;
¹H-NMR (600 MHz, DMSO-d$_6$): δ 7.23 (dd, 1H), 6.40 (dd, 1H), 5.77 (s, 2H), 5.63 (s, 2H), 4.29-4.15 (m, 2H), 1.56 (s, 3H).

c) [(R)-4-(6-Amino-3-fluoro-pyridin-2-yl)-5,5-difluoro-4-methyl-5,6-dihydro-4H-[1,3]oxazin-2-yl]-carbamic acid tert-butyl ester To a solution of (R)-4-(6-amino-3-fluoro-pyridin-2-yl)-5,5-difluoro-4-methyl-5,6-dihydro-4H-[1,3]oxazin-2-ylamine (4.53 g, 17.41 mmol) in DCM (46 ml) was added DIPEA (4.26 ml, 24.37 mmol) and Boc$_2$O (4.56 g, 20.89 mmol) and the mixture was warmed to 40° C. over night. The solvent was evaporated (at 34° C.) and the residue was purified by chromatography on silica gel (cyclohexane/[EtOAc/MeOH 95:5] 4:1 to 1:1) to provide the title compound as colorless foam.

HPLC: Rt$_{H5}$=3.001 min; ESIMS [M+H]$^+$=361.2;
¹H-NMR (600 MHz, CDCl$_3$): δ 7.26 (t, 1H), 6.51 (d, 1H), 4.51 (br. s, 2H), 4.40-4.29 (m, 2H), 1.91 (s, 3H), 1.52 (s, 9H).

d) ((R)-4-{6-[(3-Chloro-5-trifluoromethyl-pyridine-2-carbonyl)-amino]-3-fluoro-pyridin-2-yl}-5,5-difluoro-4-methyl-5,6-dihydro-4H-[1,3]oxazin-2-yl)-carbamic acid tert-butyl ester To a solution of [(R)-4-(6-amino-3-fluoro-pyridin-2-yl)-5,5-difluoro-4-methyl-5,6-dihydro-4H-[1,3]oxazin-2-yl]-carbamic acid tert-butyl ester (134 mg, 0.372 mmol) in DMF (1.3 ml) was added 3-chloro-5-trifluoromethyl-pyridine-2-carboxylic acid (101 mg, 0.446 mmol) and HOAt (91 mg, 0.669 mmol). The mixture was cooled to 0° C., EDC*HCl (107 mg, 0.558 mmol) was added and the mixture stirred for 1 h while allowing to warm to rt. To the reaction mixture was added TBME and water, the layers were separated and the aq. layer extracted with TBME. The combined organic layers were washed with sat. aq. NaHCO$_3$, sat. aq. NaCl, dried with MgSO$_4$ and evaporated. The residue was purified by chromatography on silica gel (cyclohexane/EtOAc 6:1 to 5:1) to provide the title compound as colorless solid.

HPLC: Rt$_{H7}$=2.920 min; ESIMS [M+H]$^+$=568.0/570.0;
¹H-NMR (600 MHz, DMSO-d$_6$): δ 11.25 (s, 1H), 9.65 (s, 1H), 9.08 (br. s, 1H), 8.72 (br. s, 1H), 8.23 (d, 1H), 7.83 (t, 1H), 4.57-4.41 (m, 2H), 1.72 (s, 3H), 1.40 (s, 9H).

e) 3-Chloro-5-trifluoromethyl-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide To a solution of ((R)-4-{6-[(3-chloro-5-trifluoromethyl-pyridine-2-carbonyl)-amino]-3-fluoro-pyridin-2-yl}-5,5-difluoro-4-methyl-5,6-dihydro-4H-[1,3]oxazin-2-yl)-carbamic acid tert-butyl ester (180 mg, 0.317 mmol) in DCM (1.5 ml) was added TFA (0.5 ml) and the mixture was stirred at it for 1 h. The reaction mixture was poured on 10% aq. $Na_2CO_3$, more DCM was added and the layers were separated. The aq. phase was extracted with DCM (3×), the combined DCM phases were dried with $K_2CO_3$ and evaporated to provide the title compound as colorless solid.

HPLC: $Rt_{H8}$=3.001 min; ESIMS [M+H]$^+$=468.0/470.0; $^1$H-NMR (600 MHz, CDCl$_3$): δ 10.22 (br. s, 1H), 8.87 (s, 1H), 8.41 (dd, 1H), 8.18 (s, 1H), 7.53 (t, 1H), 4.33-4.13 (m, 4H), 1.85 (s, 3H).

Examples 8 to 21

The compounds listed in Table 4 were prepared by a procedure analogous to that used in Example 7.

TABLE 4

| Example | Compound | $^1$H-NMR (solvent; δ) | MS [m/z; (M + 1)$^+$] |
|---|---|---|---|
| 8 | 3-Amino-5-trifluoromethyl-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide | (400 MHz, DMSO-d$_6$): δ 10.28 (s, 1H), 8.38 (s, 1H), 8.15 (dd, 1H), 8.10 (br. s, 2H), 7.80 (dd, 1H), 5.79 (s, 2H), 4.40-4.18 (m, 2H), 1.67 (s, 3H) | LCMS: $Rt_{H2}$ = 0.78 [M + 1] = 450.1 |
| 9 | 3,5-Dichloro-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide | (400 MHz, DMSO-d$_6$): δ 10.97 (br. s, 1H), 8.73 (s, 1H), 8.45 (s, 1H), 8.17 (dd, 1H), 7.75 (dd, 1H), 5.75 (br. s, 2H), 4.36-4.28 (m, 2H), 1.66 (s, 3H) | LCMS: $Rt_{H2}$ = 0.75; [M + 1] = 434.0/436.0 |
| 10 | 3-Amino-5-(2,2,2-trifluoro-ethoxy)pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide | (400 MHz, DMSO-d$_6$): δ 9.93 (s, 1H), 8.16 (dd, 1H), 7.89 (br. s, 2H), 7.78-7.73 (m, 1H), 7.73 (s, 1H), 5.78 (s, 2H), 5.05 (q, 2H), 4.36-4.27 (m, 1H), 4.25-4.16 (m, 1H), 1.66 (s, 3H) | LCMS: $Rt_{H2}$ = 0.43; [M + 1] = 480.5 |

TABLE 4-continued

| Example | Compound | ¹H-NMR (solvent; δ) | MS [m/z; (M + 1)⁺] |
|---|---|---|---|
| 11 | 3-Amino-5-(2,2-difluoro-ethoxy)-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide | (400 MHz, DMSO-d₆): δ 9.96 (br. s., 1H), 8.19 (dd, 1H), 8.03-7.75 (m, 3H), 7.67 (s, 1H), 6.46 (tt, 1H), 4.63 (td, 2H), 4.42-4.31 (m, 2H), 1.71 (br. s, 3H) | LCMS: $Rt_{H2}$ = 0.78; [M + 1] = 462.1 |
| 12 | 3-Amino-5-(3-fluoro-propoxy)-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide | (400 MHz, DMSO-d₆): δ 10.14 (br. s, 1H), 8.28 (d, 1H), 7.96 (t, 1H), 7.79 (br. s, 2H), 7.56 (s, 1H), 4.96 (br. s, 1H), 4.80 (br. s, 1H), 4.68 (t, 1H), 4.56 (t, 1H), 4.43 (t, 2H), 2.16 (dquin, 2H), 1.91 (br. s, 3H) | LCMS: $Rt_{H2}$ = 0.80; [M + 1] = 458.1 |
| 13 | 5-Methoxy-3-methyl-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide | (400 MHz, CDCl₃): δ 10.49 (s, 1H), 8.36 (dd, 1H), 8.17 (d, 1H), 7.45 (dd, 1H), 7.08 (dd, 1H), 4.40 (br. s, 2H), 4.28-4.08 (m, 2H), 3.92 (s, 3H), 2.79 (s, 3H), 1.85 (t, 3H) | LCMS: $Rt_{H2}$ = 0.77; [M + 1] = 411.1 |
| 14 | 3-Amino-5-(3-methoxy-prop-1-ynyl)-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide | (400 MHz, DMSO-d₆): δ 10.26 (s, 1H), 8.19 (dd, 1H), 7.95 (d, 1H), 7.75 (dd, 1H), 7.36 (d, 1H), 7.09 (br. s, 2H), 5.79 (s, 2H), 4.39 (s, 2H), 4.37-4.26 (m, 1H), 4.26-4.12 (m, 1H), 3.32 (s, 3H), 1.67 (s, 3H) | LCMS: $Rt_{H2}$ = 0.78; [M + 1] = 450.1 |
| 15 | 3-Amino-5-fluoromethoxy-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide | (400 MHz, DMSO-d₆): δ 9.96 (s, 1H), 8.17 (dd, 1H), 7.89 (br. s, 2H), 7.76 (dd, 1H), 7.71 (s, 1H), 6.11 (d, 2H), 5.78 (s, 2H), 4.37-4.27 (m, 1H), 4.26-4.15 (m, 1H), 1.66 (s, 3H) | LCMS: $Rt_{H2}$ = 0.72; [M + 1] = 430.1 |

TABLE 4-continued

| Example | Compound | ¹H-NMR (solvent; δ) | MS [m/z; (M + 1)⁺] |
|---|---|---|---|
| 16 | 3-Amino-5-(2-methoxy-ethoxy)-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide | (400 MHz, DMSO-d₆): δ 9.90 (s, 1H), 8.17 (d, 1H), 7.98-7.68 (m, 3H), 7.60 (s, 1H), 5.79 (s, 2H), 4.44 (br. s, 2H), 4.36-4.27 (m, 1H), 4.25-4.16 (m, 1H), 3.69 (br. s, 2H), 3.32 (s, 3H), 1.66 (br. s, 3H) | LCMS: Rt$_{H2}$ = 0.74; [M + 1] = 456.2 |
| 17 | 3-Amino-5-(3-hydroxy-prop-1-ynyl)-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide | (400 MHz, DMSO-d₆): δ 10.26 (s, 1H), 8.19 (dd, 1H), 7.91 (d, 1H), 7.75 (dd, 1H), 7.32 (d, 1H), 7.09 (br. s, 2H), 5.79 (br. s, 2, H), 5.46 (t, 1H), 4.44-4.26 (m, 3H), 4.26-4.13 (m, 1H), 1.67 (s, 3H) | LCMS: Rt$_{H2}$ = 0.68; [M + 1] = 435.2 |
| 18 | 3-Amino-5-fluoro-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide | (400 MHz, DMSO-d₆): δ 10.15 (s, 1H), 8.18 (dd, 1H), 7.91 (dd, 1H), 7.75 (dd, 1H), 7.25 (br. s, 2H), 7.11 (dd, 1H), 5.78 (s, 2H), 4.32 (td, 1H), 4.20 (td, 1H), 1.66 (s, 3H) | LCMS: Rt$_{H2}$ = 0.71; [M + 1] = 399.2 |
| 19 | 3-Amino-5-chloro-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide | (400 MHz, DMSO-d₆): δ 10.18 (s, 1H), 8.18 (dd, 1H), 7.92 (d, 1H), 7.76 (dd, 1H), 7.39 (d, 1H), 7.19 (br. s, 2H), 5.79 (br. s, 2H), 4.39-4.09 (m, 2H), 1.67 (s, 3H) | LCMS: Rt$_{H2}$ = 0.77; [M + 1] = 415.1 |
| 20 | 3-Chloro-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide | (400 MHz, CDCl3): δ 10.44 (br. s, 1H), 8.61 (d, 1H), 8.46 (d, 1H), 7.90 (d, 1H), 7.53 (t, 1H), 7.50-7.44 (m, 1H), 4.92 (br. s, 2H), 4.39-4.17 (m, 2H), 1.91 (br. s, 3H) | LCMS: Rt$_{H2}$ = 0.67; [M + 1] = 400.1 |

TABLE 4-continued

| Example | Compound | ¹H-NMR (solvent; δ) | MS [m/z; (M + 1)⁺] |
|---|---|---|---|
| 21 | 3-Chloro-5-(3-methoxy-prop-1-ynyl)pyridine-2-carboxylic acid [6-((R)-2-amino-5,5-difluoro-4-methyl-5,6-dihydro-4H-[1,3]oxazin-4-yl)-5-fluoro-pyridin-2-yl]-amide | (400 MHz, CDCl3): δ 10.45 (br. s, 1H), 8.62 (d, 1H), 8.47 (dd, 1H), 7.91 (d, 1H), 7.56 (dd, 1H), 4.47-4.24 (m, 4H), 3.48 (s, 3H), 1.95 (br. s, 3H) | LCMS: Rt$_{H2}$ = 0.80; [M + 1] = 468.1 |

Examples 22 to 36

The compounds presented below in Table 5 were also prepared by a procedure analogous to that used in Example 7. Examples 26 and 27 were separated after the deprotection step by prep. TLC (DCM/MeOH 95:5).

TABLE 5

| Example | Compound Structure | ¹H-NMR (solvent; δ) | MS [m/z; (M + 1)⁺] |
|---|---|---|---|
| 22 | 3-Amino-5-difluoromethyl-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide | (400 MHz, DMSO-d₆): δ 10.44 (br. s, 1H), 8.28-8.13 (m, 2H), 8.02-7.84 (m, 3H), 6.98 (t, 1H, CHF2), 4.66-4.57 (m, 2H), 1.82 (s, 3H) | LCMS: Rt$_{H2}$ = 0.69; [M + 1] = 432.2 |
| 23 | 3-Amino-5-(2-chloro-ethoxy)-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide | (400 MHz, DMSO-d₆): δ 9.91 (s, 1H), 8.17 (dd, 1H), 7.87 (br. s, 2H), 7.74 (d, 1H), 7.76 (d, 1H), 7.62 (s, 1H), 5.83 (br. s, 1H), 4.66-4.53 (m, 2H), 4.40-4.14 (m, 2H), 4.06-3.97 (m, 2H), 1.66 (s, 3H) | LCMS: Rt$_{H2}$ = 0.79; [M + 1] = 460.1/462.1 |
| 24 | 3-Chloro-5-(2,2-difluoro-ethoxy)-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide | (400 MHz, DMSO-d₆): δ 10.68 (s, 1H), 8.46 (br s, 1H), 8.18 (d, 1H), 7.89 (s, 1H), 7.74 (t, 1H), 7.08 (d, 1H), 6.85 (d, 1H), 6.47 (t, 1H, CHF2), 4.69-4.51 (m, 2H), 4.43-4.17 (m, 2H), 1.66 (s, 3H) | LCMS: Rt$_{H2}$ = 0.79; [M + 1] = 480.1/482.1 |

TABLE 5-continued

| Example | Compound Structure | ¹H-NMR (solvent; δ) | MS [m/z; (M + 1)⁺] |
|---|---|---|---|
| 25 | 3-Amino-5-(2-fluoro-ethoxy)-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide | (400 MHz, DMSO-d₆): δ 10.00 (s, 1H), 8.21 (d, 1H), 7.90 (br. S, 2H), 7.82 (t, 1H), 7.63 (s, 1H), 4.91-4.82 (m, 1H), 4.78-4.69 (m, 1H), 4.65-4.57 (m, 1H), 4.56-4.49 (m, 1H), 4.41 (br. s, 2H), 1.75 (s, 3H) | LCMS: Rt$_{H2}$ = 0.76; [M + 1] = 444.2 |
| 26 | 3-Chloro-5-fluoromethoxy-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide | (400 MHz, DMSO-d₆): δ 10.80 (s, 1H), 8.53 (s, 1H), 8.18 (d, 1H), 7.97 (s, 1H), 7.75 (t, 1H), 6.13 (s, 1H), 6.00 (s, 1H), 5.78 (br. s, 2H), 4.46-4.17 (m, 2H), 1.66 (s, 3H) | LCMS: Rt$_{H2}$ = 0.74; [M + 1] = 448.1/450.2 |
| 27 | 3-Chloro-5-ethoxy-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide | (400 MHz, DMSO-d₆): δ 10.60 (s, 1H), 8.38 (s, 1H), 8.18 (d, 1H), 7.83-7.67 (m, 2H), 5.82 (br. s, 1H), 4.41-4.15 (m, 4H), 1.66 (s, 3H), 1.38 (t, 3H) | LCMS: Rt$_{H2}$ = 0.81; [M + 1] = 444.1/446.3 |
| 28 | 3-Amino-5-(penta-deutero-ethoxy)-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide | (600 MHz, DMSO-d₆): δ 9.90 (s, 1H), 8.17 (d, 1H), 7.90 (br. s, 2H), 7.75 (t, 1H), 7.56 (s, 1H), 5.82 (br. s, 2H), 4.32 (q, 1H), 4.20 (q, 1H), 1.66 (s, 3H) | LCMS: Rt$_{H2}$ = 0.79; [M + 1] = 431.3 |
| 29 | 3-Amino-5-(2-methoxy-ethyl)-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide | (600 MHz, DMSO-d₆): δ 10.16 (s, 1H), 8.18 (d, 1H), 7.90 (s, 1H), 7.77 (t, 1H), 7.62 (br. s, 2H), 5.85 (br. s, 1H), 4.34 (q, 1H), 4.22 (q, 1H), 3.71 (t, 2H), 3.25 (s, 3H), 2.92 (t, 2H), 1.67 (s, 3H) | LCMS: Rt$_{H2}$ = 0.69; [M + 1] = 440.3 |

TABLE 5-continued

| Example | Compound Structure | $^1$H-NMR (solvent; δ) | MS [m/z; (M + 1)$^+$] |
|---|---|---|---|
| 30 | 4-Chloro-1-difluoromethyl-1H-pyrazole-3-carboxylic acid [6-((R)-2-amino-5,5-difluoro-4-methyl-5,6-dihydro-4H-[1,3]oxazin-4-yl)-5-fluoro-pyridin-2-yl]-amide | (400 MHz, DMSO-d$_6$): δ 10.27 (s, 1H), 8.81 (s, 1H), 8.14-8.01 (m, 1H), 7.94 (s, 1H), 7.84-7.68 (m, 2H), 4.33 (t, 2H), 1.66 (s, 3H) | LCMS: Rt$_{H2}$ = 0.74; [M + 1] = 439.1/441.1 |
| 31 | 3-Amino-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide | (400 MHz, DMSO-d$_6$): δ 10.22 (s, 1H), 8.37 (d, 1H), 8.18 (dd, 1H), 7.97 (d, 1H), 7.78 (dd, 1H), 7.65 (br. s, 2H), 5.85 (br. s, 2H), 4.42-4.15 (m, 2H), 1.68 (s, 3H) | LCMS: Rt$_{H2}$ = 0.60; [M + 1] = 382.2 |
| 32 | 3-Chloro-5-(3-hydroxy-prop-1-ynyl)-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide | (400 MHz, DMSO-d$_6$): δ 10.99 (s, 1H), 8.68 (s, 1H), 8.23 (s, 1H), 8.17 (d, 1H), 7.75 (t, 1H), 5.76 (br. s, 2H), 5.52 (t, 1H), 4.39 (d, 2H), 4.32 (br. s, 2H), 1.66 (s, 3H) | LCMS: Rt$_{H2}$ = 0.68; [M + 1] = 454.2/456.1 |
| 33 | 3-Amino-5-difluoromethyl-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide | (400 MHz, DMSO-d$_6$): δ 10.34 (s, 1H), 8.20 (dd, 1H), 8.07 (s, 1H), 7.77 (dd, 1H), 7.48 (s, 1H), 7.24 (br. s, 2H), 7.14 (t, 1H, CHF2), 5.80 (s, 2H), 4.39-4.14 (m, 2H), 1.67 (s, 3H) | LCMS: Rt$_{H2}$ = 0.74; [M + 1] = 431.2 |
| 34 | 3-Amino-6-chloro-5-(1,1-difluoro-ethyl)-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide | (400 MHz, DMSO-d$_6$): δ 9.99 (s, 1H), 8.13 (dd, 1H), 7.97 (br. s, 2H), 7.80 (dd, 1H), 5.83 (br. s, 2H), 4.43-4.17 (m, 2H), 2.05 (t, 3H), 1.68 (s, 3H) | LCMS: Rt$_{H2}$ = 0.81; [M + 1] = 480.2/482.2 |

TABLE 5-continued

| Example | Compound Structure | ¹H-NMR (solvent; δ) | MS [m/z; (M + 1)⁺] |
|---|---|---|---|
| 35 | 5-Cyano-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide | (600 MHz, DMSO-$d_6$): δ 10.41 (s, 1H), 9.26 (s, 1H), 8.64 (dd, 1H), 8.35 (d, 1H), 8.23 (d, 1H), 7.82 (t, 1H), 5.83 (br. s, 2H), 4.40-4.20 (m, 2H), 1.68 (s, 3H) | LCMS: $Rt_{H2}$ = 0.66; [M + 1] = 391.2 |
| 36 | 3-Chloro-5-(1,1-difluoro-ethyl)-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide | (600 MHz, CDCl₃): δ 10.30 (br. s, 1H), 8.74 (s, 1H), 8.49-8.36 (m, 1H), 8.03 (s, 1H), 7.52 (t, 1H), 4.33 (br. s, 1H), 4.25-4.13 (m, 2H), 2.04 (t, 3H), 1.85 (s, 3H) | LCMS: $Rt_{H8}$ = 2.981; [M + 1] = 464.0/466.0 |

Example 37

3-Amino-5-(1,1-difluoro-ethyl)-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide

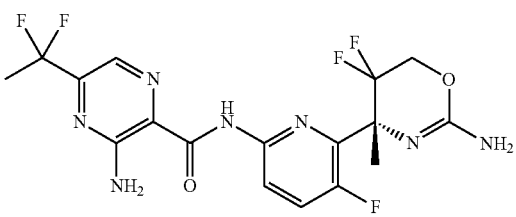 [SMILES: CC(F)(F)c1cnc(C(=O)Nc2ccc(F)c([C@@]3(C)N=C(N)OCC3(F)F)n2)c(N)n1]

To a solution of 3-amino-6-chloro-5-(1,1-difluoro-ethyl)-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide [Example 34] (54 mg, 0.113 mmol) in MeOH/THF (1:1, 10 ml) was added Pd/C 10% (BASF 4505 D/R E, 12 mg) and the mixture was set under an hydrogen atmosphere. After 2.5 h more Pd/C 10% (BASF 4505 D/R E, 11 mg) was added and the hydrogenation continued for another 2.5 h. The reaction mixture was filtered through a pad of Celite, washed with MeOH and the solvent evaporated. The residue was purified by chromatography on silica gel (DCM to DCM/MeOH 9:1) to provide the title compound as yellow foam.

HPLC: $Rt_{H2}$=0.76 min; ESIMS [M+H]⁺=446.2; ¹H-NMR (400 MHz, DMSO-$d_6$): δ 10.25 (s, 1H), 8.22 (s, 1H), 8.17 (dd, 1H), 7.92 (s, 2H), 7.79 (dd, 1H), 5.82 (br. s, 1H), 4.44-4.14 (m, 2H), 2.00 (t, 3H), 1.68 (s, 3H).

Preparation of Intermediates

Alternative synthesis of (R)-3-amino-3-(6-bromo-3-fluoro-pyridin-2-yl)-2,2-difluoro-butan-1-ol (Example 1 intermediate g)

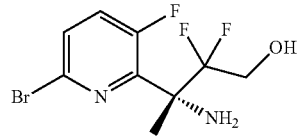 [SMILES: C[C@@](N)(c1nc(Br)ccc1F)C(F)(F)CO]

a) 1-(6-Bromo-3-fluoro-4-triethylsilanyl-pyridin-2-yl)-ethanone

To a solution of diisopropylamine (11.33 g, 112 mmol) in THF (200 ml) was added n-BuLi (44.8 ml, 2.5 mol/L in hexanes) below −50° C. A solution of 2-bromo-5-fluoro-4-triethylsilanyl-pyridine (25 g, 86 mmol) in THF (25 ml) was added to the LDA-solution at −78° C. in a drop wise manner below −65° C. After 70 minutes at −78° C. DMA (10.49 ml, 112 mmol) was added drop wise in a fast manner to the deep red solution keeping the temperature below −57° C. After 30 minutes the cooling bath was removed and the reaction mixture was allowed to reach −40° C. The cold reaction mixture was poured on a mixture of 2M aq. HCl (160 ml)/water (200 ml)/brine (100 ml). Tert.-butyl methyl ether was added and the layers were separated. The organic phase was washed twice with brine, dried over magnesium sulfate, filtered and evaporated to give a yellow oil. The crude product (28.67 g) was used in the next step without purification.

TLC (cyclohexane/ethyl acetate 10:1): $R_f$=0.61;
LC-MS: $Rt_{H1}$=1.46 min; (98% purity; ESI+−MS: m/z 332 [(M+H)$^+$, 1Br]; 334);
$^1$H-NMR (400 MHz, CDCl$_3$): 7.59 (d, J=2.8 Hz, 1H), 2.70 (s, 3H), 1.06-0.83 (m, 15H).

b) (R)-3-(6-Bromo-3-fluoro-4-triethylsilanyl-pyridin-2-yl)-2,2-difluoro-3-((R)-2-methyl-propane-2-sulfinylamino)-butyric acid ethyl ester a) A mixture of titantetraethoxide (25.07 g, 110 mmol), (R)-tert.-butylsulfinamide (13.32 g, 110 mmol) and 1-(6-bromo-3-fluoro-4-triethylsilanyl-pyridin-2-yl)-ethanone (28.67 g, 85 mmol, 98% pure) in THF (250 ml) was heated under a nitrogen atmosphere for 24 hours at 60° C. The cold reaction mixture was then concentrated to remove ethanol. Dry toluene (2×150 ml) was added and removed in vacuo to minimize the content of ethanol. Finally dry THF (250 ml) was added.

b) The Reformatsky reagent was prepared in a separate flask: To a suspension of zinc (17.15 g, 262 mmol) and copper (I) chloride (1.256 g, 12.68 mmol) in dry THF (20 ml) were added 3 drops of trimethylchlorosilane under nitrogen to activate the zinc. After 10 minutes ethyl 2-bromo-2,2-difluoroacetate (51.5 g, 254 mmol) was added slowly by syringe between 25 and 35° C. (Slightly exothermic with induction period) The reaction mixture was kept in an ultrasound bath for 45 minutes.

The sulfoximine solution was cooled to 0° C. and the Reformatsky reagent b) was quickly added to the sulfoximine solution a). The cooling bath was removed and stirring was continued at 50° C. for 4 h.

The cold reaction mixture was poured onto ice cold aqueous 5% sulfuric acid solution (300 ml) with gentle stirring. The suspension was diluted with water (150 ml) and TBME (500 to 1000 ml) and was stirred at it for 30 min (pH about 3-4). The organic phase was washed thoroughly with plenty of water with backextraction of the aqueous phase. The organic phase was finally washed with brine, dried over magnesium sulfate, filtered and concentrated. The crude product (52.4 g brown-red oil, 65.3% yield) was used in the next step without purification.

TLC (cyclohexane/ethyl acetate 2:1): $R_f$=0.46;
LC-MS: $Rt_{H1}$=1.53 min; (47% purity; ESI+−MS: m/z 559 [(M+H)$^+$, 1Br]; 561); main isomer;
LC-MS: $Rt_{H1}$=1.55 min; (11.9% purity; ESI+−MS: m/z 559 [(M+H)$^+$, 1Br]; 561); minor isomer.

c) (R)-3-(6-Bromo-3-fluoro-pyridin-2-yl)-2,2-difluoro-3-((R)-2-methyl-propane-2-sulfinylamino)-butyric acid ethyl ester Freshly ground KF (9.78 g, 168 mmol) was added to a solution of (R)-3-(6-bromo-3-fluoro-4-triethylsilanyl-pyridin-2-yl)-2,2-difluoro-3-((R)-2-methyl-propane-2-sulfinylamino)-butyric acid ethyl ester (52.34 g, 56.1 mmol, 60% pure) and acetic acid (9.64 ml, 168 mmol) in THF (200 ml). DMF (200 ml) was added and the suspension was stirred at rt. After 3 hours the reaction mixture was diluted with TBME and washed thoroughly with water, sat. sodium bicarbonate solution, water and brine, dried over magnesium sulfate, filtered and evaporated. The crude product (35.9 g yellowish-brown oil, 86% yield, 60% purity) was used in the next step without purification.

TLC (cyclohexane/ethyl acetate 2:1): $R_f$=0.30;
LC-MS: $Rt_{H1}$=1.10 min; (53% purity; ESI+−MS: m/z 445 [(M+H)$^+$, 1Br]; 447); main isomer;
LC-MS: $Rt_{H1}$=1.15 min; (7% purity; ESI+−MS: m/z 445 [(M+H)$^+$, 1Br]; 447); minor isomer.

d) (R)-2-Methyl-propane-2-sulfinic acid [(R)-1-(6-bromo-3-fluoro-pyridin-2-yl)-2,2-difluoro-3-hydroxy-1-methyl-propyl]amide To a solution of (R)-3-(6-bromo-3-fluoro-pyridin-2-yl)-2,2-difluoro-3-((R)-2-methyl-propane-2-sulfinylamino)-butyric acid ethyl ester (35.9 g, 48.4 mmol) in THF (225 ml) was portion wise added lithiumborohydride (2.63 g, 121 mmol) with external cooling. The exothermic reaction was stirred at rt for 60 min. Crushed ice and water was added carefully and the reaction mixture was diluted with TBME and neutralised with 2N HCl solution. The organic phase was washed with water and brine, dried over magnesium sulfate in the presence of charcoal, filtered and evaporated. The crude product (29.74 g brown-yellow sticky oil-resin) was used in the next step without purification.

TLC (cyclohexane/ethyl acetate 1:1): $R_f$=0.30;
LC-MS: $Rt_{H1}$=0.94 min; (83% purity; ESI+−MS: m/z 403 [(M+H)$^+$, 1Br]; 405); main isomer;
LC-MS: $Rt_{H1}$=1.15 min; (14% purity; ESI+−MS: m/z 403 [(M+H)$^+$, 1Br]; 405); minor isomer.

e) (R)-3-Amino-3-(6-bromo-3-fluoro-pyridin-2-yl)-2,2-difluoro-butan-1-ol camphersulfonic acid salt To a cold solution of (R)-2-methyl-propane-2-sulfinic acid [(R)-1-(6-bromo-3-fluoro-pyridin-2-yl)-2,2-difluoro-3-hydroxy-1-methyl-propyl]amide (29.74 g, 61.2 mmol, 83% pure) in methanol (150 ml) was added HCl/dioxane 4N (59.8 ml, 239 mmol). The reaction mixture was stirred for 2.5 hours at rt. The solvent was evaporated and to the residue was added TBME (300 ml) and crushed ice. The organic phase was extracted with water (3×200 ml, pH readjusted to about 2 with each extraction using 2N HCl solution). The aq. phase was washed with TBME and solid potassium carbonate was added. The free base was extracted with TBME and dried over magnesium sulfate, filtered and evaporated. 15.5 g brown oil. LC-MS crude Rt=0.43 min. (85%, ES+m/z 299, 301).

(+)-Campher sulfonic acid salt: (R)-3-Amino-3-(6-bromo-3-fluoro-pyridin-2-yl)-2,2-difluoro-butan-1-ol (13 g crude material, 36.52 mmol) and (+)-CSA monohydrate (9.13 g, 36.52 mmol) in acetone (230 ml) was heated until dissolution. The solution was cooled down to it and kept 10 hrs at −20° C. The solid was filtered and washed with ice cold acetone and dried at 70° C. for 2 hrs in a vacuum oven. 13.66 g white solid. (theoretical yield: 19.38 g; 70%). LC-MS: Rt=0.45 min. (>98% purity, ES+m/z 299, 301 weak signal). Chiral HPLC: Chiracel OD-H, 250×4.6 mm; heptane-ethanol-methanol 95:3:2, 1 ml/min., Rt=14.188 min 90.76%; Rt=16.17 min. 9.2%: e.e. 82%.

Recrystallization:

13.66 g was recrystallised from a mixture of hot acetone (220 ml) and ethanol (50 ml). Clear solution. The flask was kept at −20° C. over the weekend. The solid was filtered, washed with ice cold acetone and dried in a vacuum oven at 70° C. White solid: 9.31 g. LC-MS Rt=0.45 min. (100% pure, ES+m/z 299, 301). Chiral HPLC: Chiracel OD-H, 250×4.6 mm; heptane-ethanol-methanol 95:3:2, 1 ml/min., Rt=14.205 min 98.21%; Rt=16.207 min. 1.7%: e.e. 96.4%. Free base:
$^1$H-NMR (400 MHz, DMSO-d$_6$): δ 7.76-7.70 (m, 2H), 5.29 (br. s, 1H, OH), 3.89-3.70 (dt, 2H, CH2), 1.59 (s, 3H).

Preparation of Substituted Acid Building Block Intermediates

The substituted acid building blocks were either commercially available or can be prepared as described hereafter or in an analogous manner.

Acid-1: 3-Amino-5-(2,2,2-trifluoro-ethoxy)-pyrazine-2-carboxylic acid a) 3-Amino-5-(2,2,2-trifluoro-ethoxy)-pyrazine-2-carboxylic acid methyl ester A mixture of 2,2,2-trifluoro-ethanol (6.9 ml, 96 mmol) and cesium carbonate (1.56 g, 4.8 mmol) was stirred for 20 min, 3-amino-5-chloro-pyrazine-2-carboxylic acid methyl ester [28643-16-5] (600 mg, 3.2 mmol) was added and the mixture was stirred at rt for 42 h. To complete the reaction the mixture was heated to reflux for another 3 h. Saturated aq. $NH_4Cl$ was added and the mixture was extracted with EtOAc, the combined organic layers were washed with saturated aq. sodium chloride, dried with $Na_2SO_4$ and evaporated. The residue was purified by chromatography on silica gel (cyclohexane to cyclohexane/EtOAc 3:7) to provide the title compound as a colorless solid.

HPLC: $Rt_{H1}$=0.83 min; ESIMS $[M+H]^+$=252.2; $^1$H-NMR (400 MHz, DMSO-$d_6$): δ 7.66 (s, 1H), 7.60 (br. s, 2H), 5.03 (q, 2H), 3.81 (s, 3H).

b) 3-Amino-5-(2,2,2-trifluoro-ethoxy)-pyrazine-2-carboxylic acid

To a solution of 3-amino-5-(2,2,2-trifluoro-ethoxy)-pyrazine-2-carboxylic acid methyl ester (400 mg, 1.59 mmol) in THF (20 ml) was added 1N sodium hydroxide (2.5 ml, 2.5 mmol) and the mixture was stirred at room temperature overnight. To the mixture were added 1N HCl (2.39 ml, 2.39 mmol) after stirring for 5 min toluene was added and the solvents were evaporated to provide the title compound together with sodium chloride as an off-white solid. The mixture was used for coupling reactions without further purification.

HPLC: $Rt_{H1}$=0.71 min; ESIMS $[M+H]^+$=238.2; $^1$H-NMR (400 MHz, DMSO-$d_6$): δ 7.46 (s, 1H), 4.97 (q, 2H).

Acid-2: 3-Amino-5-(2,2-difluoro-ethoxy)-pyrazine-2-carboxylic acid

The title compound was prepared by an analogous procedure to Acid-1 using 2,2-difluoro-ethanol instead of 2,2,2-trifluoro-ethanol [Acid-1 step a)].

HPLC: $Rt_{H2}$=0.60 min; ESIMS $[M+H]^+$=220.2; $^1$H-NMR (400 MHz, DMSO-$d_6$): δ 12.51 (br. s, 1H), 7.62 (s, 1H), 6.43 (tt, 1H), 4.59 (td, 2H).

Acid-3: 3-Amino-5-(3-fluoro-propoxy)-pyrazine-2-carboxylic acid

The title compound was prepared by an analogous procedure to Acid-1 using 3-fluoro-propan-1-ol instead of 2,2,2-trifluoro-ethanol [Acid-1 step a)] and lithium hydroxide instead of sodium hydroxide [Acid-1 step b)].

HPLC: $Rt_{H1}$=0.60 min; ESIMS $[M+H]^+$=216.1; $^1$H-NMR (400 MHz, DMSO-$d_6$): δ 8.98 (br. s, 1H), 7.19 (s, 1H), 6.82 (br. s, 1H), 4.65 (t, 1H), 4.53 (t, 1H), 4.32 (t, 2H), 2.20-1.99 (m, 2H).

Acid-4: 3-Amino-5-(3-fluoro-propoxy)-pyrazine-2-carboxylic acid

The title compound was prepared by an analogous procedure to Acid-1 using 2-methoxy-ethanol instead of 2,2,2-trifluoro-ethanol [Acid-1 step a)].

HPLC: $Rt_{H1}$=0.53 min; ESIMS $[M+H]^+$=214.2; $^1$H-NMR (400 MHz, DMSO-$d_6$): δ 12.49 (br. s, 1H), 7.54 (br. s, 2H), 7.51 (s, 1H), 4.49-4.33 (m, 2H), 3.71-3.60 (m, 2H), 3.30 (s, 3H).

Acid-5: 3-Amino-5-(2-fluoro-ethoxy)-pyrazine-2-carboxylic acid a) 3-Amino-4-oxy-pyrazine-2-carboxylic acid methyl ester To a solution of 3-amino-pyrazine-2-carboxylic acid methyl ester [16298-03-6] (15 g, 98 mmol) in $CHCl_3$ (245 ml) was added mCPBA (26.6 g, 108 mmol) and the resulting mixture was heated up to reflux for 40 min. To complete the reaction, more mCPBA (2.5 g) was added and the reaction was heated to reflux for another 40 min. The mixture was diluted in DCM/Chloroform (1/1) and then saturated aq. $NaHCO_3$ was added. The organic layer was separated and the aqueous layer was extracted several times with DCM/Chloroform (1/1). The combined organic layers were dried with $Na_2SO_4$, filtered and evaporated to give a yellow solid. (12.6 g, 68% yield, 90% purity)

HPLC: $Rt_{H1}$=0.33 min; ESIMS $[M+H]^+$=170.1; $^1$H-NMR (400 MHz, DMSO-$d_6$): δ 8.48 (d, 1H), 7.88 (d, 1H), 7.70 (br. s, 2H), 3.89 (s, 3H).

b) 3-Acetylamino-5-oxo-4,5-dihydro-pyrazine-2-carboxylic acid methyl ester

A solution of 3-amino-4-oxy-pyrazine-2-carboxylic acid methyl ester (11.3 g, 66.8 mmol) in $Ac_2O$ (150 ml, 1590 mmol) and AcOH (200 ml) was heated to 120° C. for 2 h, then the reaction was cooled to rt, the solvent was evaporated and co-evaporated with toluene. The resulting crude material was directly used in the next step without further purification.

HPLC: $Rt_{H1}$=0.45 min; ESIMS $[M+H]^+$=212.1; $^1$H-NMR (400 MHz, DMSO-$d_6$): δ 12.55 (br. s, 1H), 11.04-10.75 (m, 1H), 7.76 (br. s, 1H), 3.81 (s, 3H), 2.25 (s, 3H).

c) 3-Acetylamino-5-(2-fluoro-ethoxy)-pyrazine-2-carboxylic acid methyl ester

To a solution of 3-acetylamino-5-oxo-4,5-dihydro-pyrazine-2-carboxylic acid methyl ester (300 mg, 1.136 mmol, 80% purity) in dry THF (8 ml) under argon were added triphenylphosphine (119 mg, 0.455 mmol) and diethyl azodicarboxylate (DEAD, 0.072 ml, 0.455 mmol) at −10° C. The reaction was stirred at −10° C. for 15 min and then 2-fluoro-ethanol (0.033 ml, 0.568 mmol) was added. The reaction was stirred at rt for 15 min. To complete the reaction, more triphenylphosphine (119 mg, 0.455 mmol) and DEAD (0.072 ml, 0.455 mmol) were added at −10° C. and the resulting mixture was stirred at −10° C. for 15 min before the addition of 2-fluoro-ethanol (0.033 ml, 0.568 mmol). The reaction was stirred for 100 min. More triphenylphosphine (119 mg, 0.455 mmol) and DEAD (0.072 ml, 0.455 mmol) were added at −10° C. and the resulting mixture was stirred at −10° C. for 15 min before the addition of 2-fluoroethanol (0.033 ml, 0.568 mmol). The reaction was stirred for another 2 h. Saturated aq. $NaHCO_3$ was added and the mixture was extracted with EtOAc, the combined organic layers were washed with aq. sodium chloride, filtered and dried with $Na_2SO_4$ and evaporated. The residue was purified by chromatography on silica gel (DCM to DCM/EtOAc 9:1) to provide the title compound as yellow oil (300 mg).

HPLC: $Rt_{H2}$=0.63 min; ESIMS $[M+H]^+$=258.4; $^1$H-NMR (400 MHz, DMSO-$d_6$): δ 10.70 (s, 1H), 8.14 (s, 1H), 4.98-4.81 (m, 1H), 4.77-4.72 (m, 1H), 4.68-4.63 (m, 1H), 4.60-4.56 (m, 1H), 3.79 (s, 3H), 2.21 (s, 3H).

d) 3-Amino-5-(2-fluoro-ethoxy)-pyrazine-2-carboxylic acid methyl ester

To a mixture of 3-acetylamino-5-(2-fluoro-ethoxy)-pyrazine-2-carboxylic acid methyl ester (330 mg, 0.962 mmol) in dry MeOH (12 ml) was added sodium methoxide (52.0 mg, 0.962 mmol) at 0° C. The resulting suspension was stirred at it for 1 h. Saturated aq. $NH_4Cl$, was added and then mixture was extracted with EtOAc. The combined organic layers were dried with $Na_2SO_4$, filtered and evaporated. The residue was purified by chromatography on silica gel (DCM to DCM/EtOAc 9:1) to provide the title compound as white solid (176 mg).

HPLC: $Rt_{H2}$=0.62 min; ESIMS $[M+H]^+$=216.1; $^1$H-NMR (400 MHz, DMSO-$d_6$): δ 7.56 (s, 1H), 7.50 (br. s, 2H), 4.87-4.79 (m, 1H), 4.74-4.67 (m, 1H), 4.62-4.55 (m, 1H), 4.53-4.45 (m, 1H), 3.80 (s, 3H).

e) 3-Amino-5-(2-fluoro-ethoxy)-pyrazine-2-carboxylic acid

To a solution of 3-amino-5-(2-fluoro-ethoxy)-pyrazine-2-carboxylic acid methyl ester (176 mg, 0.818 mmol) in THF (6.8 ml) was added a solution of 1M NaOH (900 μl, 0.900 mmol). The reaction was stirred at it for 48 h. A solution of 1M HCl (1096 μL, 1.096 mmol) was added, the mixture was evaporated to dryness and then co-evaporated with toluene to give a light purple solid (212 mg). The crude material was used directly for the coupling reactions.

HPLC: $Rt_{H2}$=0.50 min; ESIMS $[M+H]^+$=202.1; $^1$H-NMR (400 MHz, DMSO-$d_6$): δ 12.52 (br. s, 1H), 7.56 (br. s, 2H), 7.54 (s, 1H), 4.83 (dd, 1H), 4.71 (dd, 1H), 4.60-4.54 (m, 1H), 4.50 (dd, 1H).

Acid-6: 3-Amino-5-(2-chloro-ethoxy)-pyrazine-2-carboxylic acid

The title compound was prepared by an analogous procedure to Acid-5 using 2-chloro-ethanol instead of 2-fluoro-ethanol [Acid-5 step c)], adding more 1M NaOH (200 μl, 0.200 mmol) after 48 h of stirring in step e).

HPLC: $Rt_{H2}$=0.62 min; ESIMS $[M+H]^+$=218.1; $^1$H-NMR (400 MHz, DMSO-$d_6$): δ 12.45 (br. s, 1H), 7.69 (br s, 2H), 7.48 (s, 1H), 4.59-4.46 (m, 2H), 4.01-3.93 (m, 2H).

Acid-7: 3-Amino-5-penta-deutero-ethoxy-pyrazine-2-carboxylic acid

The title compound was prepared by an analogous procedure to Acid-5 using penta-deutero-ethanol instead of 2-fluoro-ethanol [Acid-5 step c)], applying a reaction time of 24 h after the second addition of triphenylphosphine, DEAD and penta-deutero-ethanol instead of 1 h in step c).

HPLC: $Rt_{H2}$=0.58 min; ESIMS $[M+H]^+$=189.1 $^1$H-NMR (400 MHz, DMSO-$d_6$): δ 12.43 (br. s, 1H), 7.52 (br. s, 2H), 7.46 (s, 1H).

Acid-8: 3-Amino-5-[2-(tert-butoxycarbonyl-methyl-amino)-ethoxy]-pyrazine-2-carboxylic acid The title compound was prepared by an analogous procedure to Acid-5 using tert-butyl 2-hydroxyethyl-methyl-carbamate [57561-39-4] instead of 2-fluoro-ethanol [Acid-5 step c)], applying a reaction time of 24 h after the third addition of triphenylphosphine, DEAD and 2-hydroxyethyl-methyl-carbamate instead of 2 h in step c). In step e) a second and a third addition of 1M NaOH (106 μl, 0.106 mmol) after 72 h and after 144 h were done, involving the quenching of 1M HCl (539 μl, 0.539 mmol).

HPLC: $Rt_{H2}$=0.82 min; ESIMS $[M+H]^+$=313.1 $^1$H-NMR (400 MHz, DMSO-$d_6$, main rotamer): δ 7.32 (br. s, 1H), 4.34 (br. s, 2H), 3.55 (br. s, 2H), 2.83 (s, 3H), 1.29 (br. s, 9H).

Acid-9: 3-(di-tert-Butoxycarbonyl-amino)-5-difluoromethyl-pyrazine-2-carboxylic acid a) 3-Amino-5-vinyl-pyrazine-2-carboxylic acid methyl ester

To a mixture of 3-amino-5-chloro-pyrazine-2-carboxylic acid methyl ester (GB 1248146, 161 mg 0.86 mmol), tributyl (vinyl)tin (0.352 ml, 1.204 mmol) and lithium chloride (102 mg, 2.498 mmol) in DMF (4 ml) was added $PdCl_2(PPh_3)_2$ (30.2 mg, 0.043 mmol) and the mixture was heated to 85° C. for 2.5 h. After cooling to room temperature water was added and the mixture was extracted with EtOAc, the combined organic layers were washed with water and half saturated aq. NaCl, dried with $Na_2SO_4$ and evaporated. The residue was purified by chromatography on silica gel (cyclohexane to cyclohexane/EtOAc 1:9) to provide the title compound as yellow solid.

HPLC: $Rt_{H4}$=0.71 min; ESIMS $[M+H]^+$=179.9; $^1$H-NMR (600 MHz, DMSO-$d_6$): δ 8.04 (s, 1H), 7.35 (br. s, 1H), 6.75 (dd, 1H), 6.38 (d, 1H), 5.70 (d, 1H), 3.84 (s, 3H).

b) 3-(di-tert-Butoxycarbonyl-amino)-5-vinyl-pyrazine-2-carboxylic acid methyl ester To an ice cooled solution of 3-amino-5-vinyl-pyrazine-2-carboxylic acid methyl ester (1.28 g, 7.14 mmol) in DCM (45 ml) was added $Boc_2O$ (8.58 g, 39.3 mmol) and the mixture was stirred at room temperature for 30 min, then the mixture was heated to 40° C. for 4 h. After cooling to room temperature water was added and the mixture was extracted with DCM. The combined organic layers were washed with 0.5N HCl and saturated aq. NaCl, dried with $Na_2SO_4$ and evaporated. The residue was purified by chromatography on silica gel (cyclohexane+5% $NEt_3$ to EtOAc+5% $NEt_3$) to provide the title compound as yellow solid.

HPLC: $Rt_{H1}$=1.15 min; ESIMS $[M-Boc]^+$=280.3; $^1$H-NMR (400 MHz, DMSO-$d_6$): δ 8.93 (s, 1H), 7.00 (dd, 1H), 6.51 (dd, 1H), 5.86 (dd, 1H), 3.88 (s, 3H), 1.34 (s, 18H).

c) 3-(di-tert-Butoxycarbonyl-amino)-5-formyl-pyrazine-2-carboxylic acid methyl ester A mixture of 3-(di-tert-butoxycarbonyl-amino)-5-vinyl-pyrazine-2-carboxylic acid methyl ester (1 g, 2.64 mmol) and sodium bicarbonate (0.332 g, 3.95 mmol) in DCM (45 ml) and MeOH (15 ml) was cooled to −78° C. and purged with oxygen for 5 min. The reaction mixture was treated with ozone for 40 min until the mixture turned blue. The reaction mixture was purged with oxygen for 10 min and with nitrogen for 10 min, then dimethyl sulfide (0.487 ml, 6.59 mmol) was added at −78° C. and the mixture was allowed to warm to room temperature. The mixture was diluted with DCM and washed with 10% aq. sodium thiosulfate. The aq. layer was extracted with DCM and the combined organic layers were dried with $Na_2SO_4$ and evaporated to provide the title compound as yellow oil. The compound was used for the next step without further purification.

$^1$H-NMR (400 MHz, DMSO-$d_6$): δ 10.07 (s, 1H), 9.24 (s, 1H), 3.94 (s, 3H), 1.36 (s, 18H).

d) 3-(di-tert-Butoxycarbonyl-amino)-5-difluoromethyl-pyrazine-2-carboxylic acid methyl ester To an ice cooled solution of 3-(di-tert-butoxycarbonyl-amino)-5-formyl-pyrazine-2-carboxylic acid methyl ester (550 mg, 1.44 mmol) in DCM (20 ml) was added dropwise within 1 h Deoxofluor (50% in THF, 0.798 ml, 4.33 mmol). Stirring was continued at 0° C. for 2.5 h then the reaction mixture was allowed to room temperature over night. Saturated aq. sodium bicarbonate was added and the mixture extracted with EtOAc, the combined organic layers were washed with sat. aq. sodium chloride, dried with $Na_2SO_4$ and evaporated. The residue was purified by chromatography on silica gel (cyclohexane+5% $NEt_3$ to cyclohexane+5% $NEt_3$/EtOAc+5% $NEt_3$ 1:1) to provide the title compound as colorless solid.

HPLC: $Rt_{H1}$=1.14 min; ESIMS [2M+Na]$^+$=829.6; $^1$H-NMR (600 MHz, DMSO-$d_6$): δ 9.14 (s, 1H), 7.26 (t, 1H, CHF2), 3.92 (s, 3H), 1.33 (s, 18H).

e) 3-(di-tert-Butoxycarbonyl-amino)-5-difluoromethyl-pyrazine-2-carboxylic acid

To a solution of 3-(di-tert-butoxycarbonyl-amino)-5-difluoromethyl-pyrazine-2-carboxylic acid methyl ester (75 mg, 0.186 mmol) in THF (2 ml) was added dropwise 1N NaOH (0.205 ml, 0.205 mmol) and the reaction mixture was stirred for 1.5 h. To the mixture was added 1N HCl (0.186 ml, 0.186 mmol) after stirring for 5 min toluene was added and the solvents were evaporated to provide the title compound together with sodium chloride as colorless solid. The mixture was used for coupling reactions without further purification.

HPLC: $Rt_{H4}$=0.89 min; ESIMS [M-Boc]$^+$=290.0; $^1$H-NMR (400 MHz, DMSO-$d_6$): δ 14.30 (br. s, 1H), 9.10 (s, 1H), 7.25 (t, 1H, CHF2), 1.33 (s, 18H).

Acid-10: 3-Amino-5-(3-methoxy-prop-1-ynyl)-pyridine-2-carboxylic acid a) 3-Amino-5-(3-methoxy-prop-1-ynyl)-pyridine-2-carboxylic acid methyl ester To a solution of 3-methoxy-propyne (421 mg, 6 mmol), bis(triphenylphosphine)palladium(II) chloride (84 mg, 0.12 mmol), copper(I) iodide (23 mg, 0.12 mmol) and $NEt_3$ (1.17 ml, 8.4 mmol) in THF (10 ml) under Argon was added 3-amino-5-bromo-pyridine-2-carboxylic acid methyl ester (277 mg, 1.2 mmol) and the mixture was heated to 80° C. for 5 h. At 0° C. water (12 ml) was added and the mixture was extracted with EtOAc, the combined organic layers were washed with half-saturated aq. sodium chloride, dried with $Na_2SO_4$ and evaporated. The residue was purified by chromatography on silica gel (cyclohexane to cyclohexane/EtOAc 1:4) to provide the title compound as orange solid.

HPLC: $Rt_{H1}$=0.67 min; ESIMS [M+H]$^+$=221.1; $^1$H-NMR (600 MHz, DMSO-$d_6$): δ 7.85 (d, 1H), 7.33-7.22 (m, 1H), 6.77 (s, 2H), 4.35 (s, 2H), 3.80 (s, 3H), 3.33 (s, 3H).

b) 3-Amino-5-(3-methoxy-prop-1-ynyl)-pyridine-2-carboxylic acid

To a solution of 3-amino-5-(3-methoxy-prop-1-ynyl)-pyridine-2-carboxylic acid methyl ester (263 mg, 1.2 mmol) in THF (6 ml) was added 1N lithium hydroxide (1.32 ml, 1.32 mmol) at 0° C. and the mixture was stirred at room temperature for 2 h. To the mixture was added 1N HCl (1.2 ml, 1.2 mmol) at 0° C., after stirring for 5 min toluene was added and the solvents were evaporated to provide the title compound together with lithium chloride as an off-white solid. The mixture was used for coupling reactions without further purification.

HPLC: $Rt_{H1}$=0.45 min; ESIMS [M+H]$^+$=207.2; $^1$H-NMR (600 MHz, DMSO-$d_6$): δ 7.84 (s, 1H), 7.30 (s, 1H), 6.92 (br. s., 1H), 4.35 (s, 2H), 3.33 (s, 3H).

Acid-11: 3-Chloro-5-[3-(tetrahydro-pyran-2-yloxy)-prop-1-ynyl)-pyridine-2-carboxylic acid The title compound was prepared by an analogous procedure to Acid-xx using 5-bromo-3-chloro-pyridine-2-carboxylic acid methyl ester instead of 3-amino-5-bromo-pyridine-2-carboxylic acid methyl ester and 2-prop-2-ynyloxy-tetrahydro-pyran instead of 3-methoxy-propyne [Acid-xx step a)].

HPLC: $Rt_{H2}$=0.68 min; ESIMS [M+H]$^+$=296.1; $^1$H-NMR (400 MHz, DMSO-$d_6$): δ 14.02 (br. s, 1H), 8.65 (s, 1H), 8.26 (s, 1H), 4.84 (br. s, 1H), 4.66-4.36 (m, 2H), 3.85-3.64 (m, 1H), 3.58-3.41 (m, 1H), 1.80-1.61 (m, 2H), 1.60-1.41 (m, 4H).

Acid-12: 3-Chloro-5-(3-methoxy-prop-1-ynyl)-pyridine-2-carboxylic acid

To a solution of 3-methoxy-propyne (421 mg, 6 mmol), bis(triphenylphosphine)palladium(II) chloride (84 mg, 0.12 mmol), copper(I) iodide (23 mg, 0.12 mmol) and $NEt_3$ (1.17 ml, 8.4 mmol) in THF (10 ml) under Argon was added 3-chloro-5-bromo-pyridine-2-carboxylic acid methyl ester (284 mg, 1.2 mmol) and the mixture was heated to 80° C. for 5 h. At 0° C. water (12 ml) was added and the mixture was extracted with EtOAc. The aq. Phase was acidified to pH 1 by addition of 1N HCl, extracted with DCM. The combined DCM extracts were washed with half-saturated aq. sodium chloride, dried with $Na_2SO_4$ and evaporated to provide the title compound as an off-white solid, which was used for coupling reactions without further purification.

HPLC: $Rt_{H1}$=0.49 min; ESIMS [M+H]$^+$=226.3; $^1$H-NMR (600 MHz, DMSO-$d_6$): δ 14.02 (br. s., 1H), 8.64 (s, 1H), 8.24 (s, 1H), 4.39 (s, 2H), 3.33 (s, 3H).

Acid-13: 3-Amino-5-(3-hydroxy-prop-1-ynyl)-pyridine-2-carboxylic acid a) 3-Amino-5-[3-(tert-butyl-dimethyl-silanyloxy)-prop-1-ynyl)-pyridine-2-carboxylic acid methyl ester The title compound was prepared by an analogous procedure to Acid-10 using tert-butyl-dimethyl-prop-2-ynyloxy-silane instead of 3-methoxy-propyne [Acid-10 step a)].

HPLC: $Rt_{H1}$=1.23 min; ESIMS [M+H]$^+$=321.2; $^1$H-NMR (600 MHz, DMSO-$d_6$): δ 7.81 (s, 1H), 7.26 (d, 1H), 6.78 (br. s, 2H), 4.57 (s, 2H), 3.79 (s, 3H), 0.89 (s, 9H), 0.12 (s, 6H).

b) 3-Amino-5-(3-hydroxy-prop-1-ynyl)-pyridine-2-carboxylic acid methyl ester

To a solution of 3-amino-5-[3-(tert-butyl-dimethyl-silanyloxy)-prop-1-ynyl)-pyridine-2-carboxylic acid methyl ester (711 mg, 2.22 mmol) in DCM (6 ml) was added 10.2 ml TFA (133 mmol) at 0° C. and the mixture was stirred at room temperature for 17 h. To the mixture was added toluene (18 ml) and the solvents were evaporated. The residue was dissolved in EtOAc (66 ml) and washed with aq. 1M $Na_2CO_3$ solution, the aq. Phase was extracted back with EtOAc. The combined organic layers were washed with half-saturated aq. sodium chloride, dried with $Na_2SO_4$ and evaporated. The residue was purified by chromatography on silica gel (DCM to DCM/MeOH 94:6) to provide the title compound as an off-white solid.

HPLC: $Rt_{H1}$=0.50 min; ESIMS [M+H]$^+$=207.1; $^1$H-NMR (600 MHz, DMSO-d$_6$): δ 7.82 (s, 1H), 7.24 (s, 1H), 6.77 (br s, 2H), 5.43 (br. s, 1H), 4.32 (s, 2H).

c) 3-Amino-5-(3-hydroxy-prop-1-ynyl)-pyridine-2-carboxylic acid

To a solution of 3-amino-5-(3-hydroxy-prop-1-ynyl)-pyridine-2-carboxylic acid methyl ester (297 mg, 1.44 mmol) in THF (10 ml) was added 1N lithium hydroxide and the mixture was vigorously stirred at room temperature for 4.5 h. To the mixture was added 4N HCl (0.47 ml, 1.87 mmol), after dilution with toluene the solvent was evaporated, the residue was suspended in toluene and evaporated (twice). The residue was suspended in TBME/hexane, filtered and the solid dried under reduced pressure at 50° C. to provide the title compound together with lithium chloride as a brown solid. The mixture was used for coupling reactions without further purification.

HPLC: $Rt_{H5}$=1.93 min; ESIMS [M+H]$^+$=193.0; $^1$H-NMR (600 MHz, DMSO-d$_6$): δ 7.83 (s, 1H), 7.28 (s, 1H), 6.94 (br. s, 1H), 4.33 (s, 2H).

Acid-14:
3-Amino-5-difluoromethyl-pyridine-2-carboxylic acid a) 5-Difluoromethyl-3-nitro-pyridine-2-carboxylic acid tert-butyl ester The title compound was prepared by an analogous reaction sequence to Acid-9 using 5-bromo-3-nitro-pyridine-2-carboxylic acid instead of 3-amino-5-chloro-pyrazine-2-carboxylic acid methyl ester in step a) and omitting step b).

HPLC: $Rt_{H1}$=1.07 min; ESIMS [M+H]$^+$=275.3; $^1$H-NMR (600 MHz, DMSO-d$_6$): δ 9.18 (s, 1H), 8.82 (s, 1H), 7.31 (t, 1H, CHF2), 1.55 (s, 9H).

b) 5-Difluoromethyl-3-nitro-pyridine-2-carboxylic acid

In a mixture of 5 ml DCM and 2.5 ml TFA was dissolved 345 mg (1.26 mmol) 5-difluoromethyl-3-nitro-pyridine-2-carboxylic acid tert-butyl ester and the reaction mixture was stirred for 4 h. Toluene was added and the solvents were evaporated to provide the title compound as colorless solid.

HPLC: $Rt_{H1}$=0.31 min; ESIMS [2M−H]$^-$=435.3; $^1$H-NMR (600 MHz, DMSO-d$_6$): δ 14.59 (br. s, 1H), 9.16 (s, 1H), 8.80 (s, 1H), 7.31 (t, 1H, CHF2).

c) 3-Amino-5-difluoromethyl-pyridine-2-carboxylic acid

To a solution of 265 mg (1.22 mmol) 5-difluoromethyl-3-nitro-pyridine-2-carboxylic acid in EtOH was added 50 mg Raney-Nickel (Degussa B113W) and the reaction mixture was kept shaking under a hydrogen atmosphere for 16 h. The catalyst was filtered off (Celite) and washed with EtOH and the filtrate was evaporated to provide the title compound as off-white solid.

HPLC: $Rt_{H1}$=0.34 min; ESIMS [M+H]$^+$=189.2; $^1$H-NMR (600 MHz, DMSO-d$_6$): δ 7.98 (s, 1H), 7.39 (s, 1H), 7.09 (t, 1H, CHF2), 7.02 (br. s, 2H).

Acid-15: 3-Chloro-5-(2,2-difluoro-ethoxy)-pyridine-2-carboxylic acid a) 3-Chloro-5-(2,2-difluoro-ethoxy)-pyridine-2-carbonitrile To a solution of 3-chloro-5-hydroxy-pyridine-2-carbonitrile [1262860-70-7] (0.200 g, 1.23 mmol) in THF (15 ml) was added at 0° C. 2,2-difluoro-ethanol (0.123 g, 1.48 mmol) and triphenylphosphine (0.484 g, 1.84 mmol). After stirring for 10 min at 0° C. DIAD (0.373 g, 1.84 mmol) was added and the reaction mixture was stirred for 2 h at 0° C. followed by 16 h at 25° C. The reaction mixture was concentrated and the title compound was obtained after CombiFlash chromatography on silica gel (hexane/EtOAc 20:1 to 1:1) as a colorless oil.

TLC (hexane-EtOAc 1:1): Rf=0.61; UPLC $Rt_{H6}$=0.965 min; ESIMS: 217 [(M−H)$^-$]; $^1$H-NMR (400 MHz, CDCl$_3$): δ 8.31 (d, 1H), 7.32 (d, 1H), 6.12 (tt, 1H), 4.31 (dt, 2H).

b) 3-Chloro-5-(2,2-difluoro-ethoxy)-pyridine-2-carboxylic acid

To a solution of 3-Chloro-5-(2,2-difluoro-ethoxy)-pyridine-2-carbonitrile (0.202 g, 0.878 mmol) in dioxane (4 ml) was added 4N NaOH (2.2 ml, 8.8 mmol) and the resulting reaction mixture was stirred for 28 h at 85° C. The reaction mixture was diluted with water and extracted with EtOAc. The aqueous phase was acidified with 4N HCl and evaporated to dryness. The title compound was extracted with DCM/MeOH (9/1), pushed through a plug of Celite and was obtained after evaporation as a light yellow solid.

UPLC $Rt_{H6}$=0.655 min; ESIMS: 236 [(M−H)$^-$]; $^1$H-NMR (400 MHz, CD$_3$OD): δ 8.31 (d, 1H), 7.68 (d, 1H), 6.23 (tt, 1H), 4.44 (dt, 2H); $^{19}$F-NMR (400 MHz, CD$_3$OD) 128.0 (dt, 2F).

Acid-16:
3-Chloro-5-fluoromethoxy-pyridine-2-carboxylic acid a) 2,3-Dichloro-5-fluoromethoxy-pyridine To a solution of 5,6-dichloro-pyridin-3-ol [11860-92-9] (500 mg, 3.05 mmol) and $K_2CO_3$ (632 mg, 4.57 mmol) in dry ACN (12 ml) was added fluoro-iodomethane (1.156 ml, 9.15 mmol) at 0° C. The light yellow suspension was stirred for 5 min at 0° C. and then heated up to 120° C. for 30 min. Saturated aq. NH$_4$Cl was added, followed by EtOAc. The organic layer was separated and the aqueous layer was extracted twice with EtOAc. The combined organic layers were washed with brine, dried with Na$_2$SO$_4$, filtered and evaporated to give a brown oil. The crude material was directly used in the next step without further purification.

HPLC: $Rt_{H2}$=0.95 min; ESIMS [M+H]$^+$=198.1; $^1$H-NMR (400 MHz, DMSO-d$_6$): δ 8.31 (dd, 1H), 8.07 (d, 1H), 6.05 (s, 1H), 5.91 (s, 1H).

b) 3-Chloro-5-fluoromethoxy-pyridine-2-carbonitrile

To a solution of 2,3-dichloro-5-fluoromethoxy-pyridine (1.18 g, 6.02 mmol) in dry DMF (14.00 ml) were added Zinc cyanide (0.341 g, 2.90 mmol) and Zinc powder (3.94 mg, 0.060 mmol). The suspension was flushed with Argon (3×). Then tetrakis(triphenylphosphine)palladium(0) (0.570 g, 0.494 mmol) was added. The reaction was heated to 145° C. for 2 h. Water was added and the aqueous layer was extracted twice with Et$_2$O. The combined organic layers were washed with brine, dried with Na$_2$SO$_4$, filtered and evaporated. The residue was purified by chromatography on silica gel (cyclohexane to cyclohexane/EtOAc 7:3) to provide the title compound as yellow oil (515 mg).

HPLC: Rt$_{H2}$=0.81 min; ESIMS [M+H]$^+$=187.0; $^1$H-NMR (400 MHz, DMSO-d$_6$): δ 8.61 (s, 1H), 8.16 (s, 1H), 6.15 (s, 1H), 6.02 (s, 1H).

c) 3-Chloro-5-fluoromethoxy-pyridine-2-carboxylic acid

To a solution of 3-chloro-5-fluoromethoxy-pyridine-2-carbonitrile (80 mg, 0.429 mmol) in EtOH (2.4 ml) was added 1M NaOH (1.21 ml, 1.201 mmol) and the resulting solution was stirred at 70° C. over night. To complete the reaction, more 1M NaOH (1.2 ml, 1.201 mmol) was added and the reaction was stirred at 70° C. for 8 h. More 1M NaOH (1.2 ml, 1.201 mmol) was added and the reaction was stirred over night. Then 1M HCl (3.45 ml, 3.45 mmol) was added. The aqueous layer was extracted twice with EtOAc. The combined organic layers were dried with Na$_2$SO$_4$, filtered and evaporated to give a light pink solid. Mixture of 80 mg, 35% of 3-chloro-5-fluoromethoxy-pyridine-2-carboxylic acid, 38% of 3-chloro-5-ethoxy-pyridine-2-carboxylic acid.

3-Chloro-5-fluoromethoxy-pyridine-2-carboxylic acid

HPLC: Rt$_{H2}$=0.42 min; ESIMS [M+H]$^+$=206.1; $^1$H-NMR (400 MHz, DMSO-d$_6$): δ 13.36 (br. s, 1H), 8.29 (d, 1H), 7.66 (d, 1H), 6.09 (s, 1H), 5.96 (s, 1H).

3-Chloro-5-ethoxy-pyridine-2-carboxylic acid

HPLC: Rt$_{H2}$=0.59 min; ESIMS [M+H]$^+$=202.1; $^1$H-NMR (400 MHz, DMSO-d$_6$): δ 13.66 (br. s, 1H), 8.45 (d, 1H), 8.29 (d, 1H), 4.21 (q, 2H), 1.36 (t, 3H).

The crude mixture of acids was used for the coupling reaction without further purification.

Acid-17: 3-Amino-5-(2-methoxy-ethyl)-pyrazine-2-carboxylic acid a) 3-Amino-5-((Z)-2-ethoxy-vinyl)-pyrazine-2-carboxylic acid methyl ester A mixture of 3-amino-5-chloro-pyrazine-2-carboxylic acid methyl ester [28643-16-5] (2 g, 10.66 mmol), lithium chloride (1.582 g, 37.3 mmol), Pd(PPh$_3$)$_2$Cl$_2$ (0.748 g, 1.066 mmol) and tributyl-((Z)-2-ethoxy-vinyl)-stannane (6.42 ml, 19.19 mmol) in DMF (104 ml) under argon was heated at 80° C. bath temperature for 1.5 h. A saturated. aq. NH$_4$Cl was added and the mixture was extracted with MTBE, then once with EtOAc/THF 3/1. The combined organic layer was washed with brine, dried with Na$_2$SO$_4$, filtered and concentrated under reduced pressure. The residue was purified by chromatography on silica gel (cyclohexane to cyclohexane/EtOAc 1:9) to provide the title compound as yellow oil (1.96 g).

HPLC: Rt$_{H2}$=0.69 min; ESIMS [M+H]$^+$=225.1; $^1$H-NMR (400 MHz, DMSO-d$_6$): δ 8.42 (s, 1H), 7.18 (br. s, 2H), 6.88 (d, 1H), 5.23 (d, 1H), 4.15 (q, 2H), 3.82 (s, 3H), 1.32 (t, 3H).

b) 3-Amino-5-(2,2-dimethoxy-ethyl)-pyrazine-2-carboxylic acid methyl ester

A solution of 3-amino-5-((Z)-2-ethoxy-vinyl)-pyrazine-2-carboxylic acid methyl ester (220 mg, 0.986 mmol) in 3M HCl in MeOH (210 μl, 6.90 mmol) was heated at 55° C. over night. A solution of 10% of NaHCO$_3$ was added the mixture was extracted with EtOAc. The combined organic layer was dried with Na$_2$SO$_4$, filtered and concentrated under reduced pressure to obtain a brown solid (141 mg). The crude material was directly used in the next step without further purification.

HPLC: Rt$_{H1}$=0.59 min; ESIMS [M+H]$^+$=242.2.

c) 3-Amino-5-(2-methoxy-vinyl)-pyrazine-2-carboxylic acid methyl ester

To a solution of 3-amino-5-(2,2-dimethoxy-ethyl)-pyrazine-2-carboxylic acid methyl ester (300 mg, 1.244 mmol) and Et$_3$N (1.213 ml, 8.70 mmol) in DCM (10 ml) at −10° C. was added dropwise trimethylsilyl trifluoromethanesulfonate (0.809 ml, 4.48 mmol). The reaction mixture was stirred at room temperature for 100 min. A saturated solution of NaHCO$_3$ was added and the mixture was extracted twice with DCM. The combined organic layers were washed with NH$_4$Cl solution and brine, dried with Na$_2$SO$_4$, filtered and concentrated under reduced pressure to obtain a brown oil (560 mg). The resulting crude material (mixture of E and Z) was directly used in the next step without further purification.

HPLC: Rt$_{H1}$=0.63 min; ESIMS [M+H]$^+$=210.1.

d) 3-Amino-5-(2-methoxy-ethyl)-pyrazine-2-carboxylic acid methyl ester

A solution of 3-amino-5-(2-methoxy-vinyl)-pyrazine-2-carboxylic acid methyl ester (260 mg, 1.24 mmol) and Pd/C 10% (50 mg) in EtOH (10 ml) was stirred at rt and under an atmosphere of hydrogen for 17 h. To complete the reaction, more Pd/C 10% (84 mg) was added and the reaction was stirred under an atmosphere of hydrogen for 37 h. The suspension was filtered off and washed with EtOH and then residual solution was evaporated. The residue was purified by chromatography on silica gel (DCM to DCM/MeOH 9:1) to provide the title compound as yellow solid (147 mg).

HPLC: Rt$_{H2}$=0.54 min; ESIMS [M+H]$^+$=212.2; $^1$H-NMR (400 MHz, DMSO-d$_6$): δ 7.84 (s, 1H), 7.31 (br. s, 2H), 3.83 (s, 3H), 3.68 (t, 2H), 3.23 (s, 3H), 2.87 (t, 3H).

e) 3-Amino-5-(2-methoxy-ethyl)-pyrazine-2-carboxylic acid

To a solution of 3-amino-5-(2-methoxy-ethyl)-pyrazine-2-carboxylic acid methyl ester (147 mg, 0.696 mmol) in THF (14 ml) was added 1M NaOH (1.74 ml, 1.74 mmol) and the reaction mixture was stirred at room temperature for 2 h. 1M HCl (1.601 ml, 1.601 mmol) was added to the reaction mixture. The resulting mixture was evaporated and co-evaporated with toluene. The resulting crude material was directly used in the coupling step without further purification.

HPLC: Rt$_{H2}$=0.41 min; ESIMS [M+H]$^+$=198.1; $^1$H-NMR (400 MHz, DMSO-d$_6$): δ 7.68 (s, 1H), 7.62 (br. s, 2H), 3.65 (t, 2H), 3.23 (s, 3H), 2.81 (t, 3H).

Acid-18: 3-Amino-6-chloro-5-(1,1-difluoro-ethyl)-pyrazine-2-carboxylic acid a) 3-Amino-6-chloro-5-(1-ethoxy-vinyl)-pyrazine-2-carboxylic acid methyl ester A mixture of 3-amino-5,6-dichloro-pyrazine-2-carboxylic acid methyl ester [1458-18-0] (600 mg, 2.62 mmol), lithium chloride (389 mg, 9.17 mmol), Pd(PPh$_3$)$_2$Cl$_2$ (184 mg, 0.262 mmol) and tributyl-(1-ethoxy-vinyl)-stannane [97674-02-7] (1.6 ml, 4.50 mmol) in DMF (27 ml) under argon was heated at 80° C. bath temperature for 3 h and 50 min. Saturated aq. NH$_4$Cl was added and the mixture was extracted with MTBE (3×). The combined organic layers were washed with brine, dried with Na$_2$SO$_4$, filtered and concentrated under reduced pressure. The residue was purified by chromatography on silica gel (cyclohexane to cyclohexane/EtOAc 7:3) to provide the title compound as yellow solid (433 mg).

HPLC: Rt$_{H2}$=0.94 min; ESIMS [M+H]$^+$=258.1; $^1$H-NMR (400 MHz, DMSO-d$_6$): δ 7.59 (br. s, 2H), 4.64 (d, 1H), 4.58 (d, 1H), 3.91 (q, 3H), 3.86 (s, 3H), 1.31 (t, 2H).

b) 5-Acetyl-3-amino-6-chloro-pyrazine-2-carboxylic acid methyl ester

A solution of 3-amino-6-chloro-5-(1-ethoxy-vinyl)-pyrazine-2-carboxylic acid methyl ester (46 mg, 0.190 mmol) and para-toluenesulfonic acid monohydrate (73.8 mg, 0.388 mmol) in THF (2.85 ml) was stirred at rt for 1 h. Saturated aq. NaHCO$_3$ was added and the mixture was extracted twice with DCM. The combined organic layers were washed with brine, dried with Na$_2$SO$_4$, filtered and concentrated under reduced pressure to obtain a yellow solid (46 mg). This material was used for the next step without further purification.

HPLC: Rt$_{H2}$=0.73 min; ESIMS [M+H]$^+$=230.1; $^1$H-NMR (400 MHz, DMSO-d$_6$): δ 7.70 (br. s, 2H), 3.83 (s, 3H), 2.58 (s, 3H).

c) 3-Amino-6-chloro-5-(1,1-difluoro-ethyl)-pyrazine-2-carboxylic acid methyl ester To a cloudy yellow solution of 5-acetyl-3-amino-6-chloro-pyrazine-2-carboxylic acid methyl ester (178 mg, 0.775 mmol) in dry DCM (7.75 ml) was added Deoxofluor 50% in toluene (858 µl, 2.326 mmol). The reaction was stirred at it over the weekend. More Deoxofluor 50% in toluene was added (six times 858 µL, 2.326 mmol) within 3 days to complete the reaction. Saturated aq. NaHCO$_3$ was added and the mixture was extracted twice with EtOAc. The combined organic layers were washed with aq. citric acid, dried with Na$_2$SO$_4$, filtered and concentrated under reduced pressure. The residue was purified by chromatography on silica gel (cyclohexane to cyclohexane/EtOAc 7:3) to provide the title compound as yellow solid (136 mg).

HPLC: Rt$_{H2}$=0.91 min; ESIMS [M+H]$^+$=252.1; $^1$H-NMR (400 MHz, DMSO-d$_6$): δ 7.75 (br. s, 2H), 3.88 (s, 3H), 2.02 (t, 3H).

d) 3-Amino-6-chloro-5-(1,1-difluoro-ethyl)-pyrazine-2-carboxylic acid

To a solution of 3-amino-6-chloro-5-(1,1-difluoro-ethyl)-pyrazine-2-carboxylic acid methyl ester (136 mg, 0.541 mmol) in THF (5.40 ml) was added 1M LiOH (595 µl, 0.595 mmol) at 0° C. The resulting brown solution was warmed up to it for 5 h. More 1M LiOH (95 µl, 0.095 mmol) was added at 0° C. and the reaction was stirred at it for 1 h. Then 1M HCl (632 µl, 0.632 mmol) was added and then the resulting mixture was evaporated to dryness. The resulting crude material was directly used in the coupling step without further purification.

HPLC: Rt$_{H2}$=0.63 min; ESIMS [M+H]$^+$=238.1; $^1$H-NMR (400 MHz, DMSO-d$_6$): δ 13.69 (br. s, 1H), 7.75 (br. s 2H), 2.02 (t, 3H).

Acid-19: 3-Chloro-5-(1,1-difluoro-ethyl)-pyridine-2-carboxylic acid a) 3-Chloro-5-(1-ethoxy-vinyl)-pyridine-2-carboxylic acid methyl ester

To a solution of 5-bromo-3-chloro-pyridine-2-carboxylic acid methyl ester [1458-18-0] (376 mg, 1.5 mmol) in dioxane (3.7 ml) was added tributyl-(1-ethoxy-vinyl)-stannane [97674-02-7] (596 mg, 1.65 mmol), the solution was degassed and flushed with nitrogen (3×), Pd(PPh$_3$)$_4$ (87 mg, 0.075 mmol) was added, after degassing and flushing with nitrogen the mixture was heated to reflux for 4 h. The reaction mixture was diluted with EtOAc and treated with 10% aq. KF, the precipitate was filtered off and the layers were separated. The aq. Phase was extracted with EtOAc, the combined organic layers were washed with sat. aq. NaCl, dried with MgSO$_4$, filtered and concentrated under reduced pressure. The residue was purified by chromatography on silica gel (cyclohexane/EtOAc 12:1 to 6/1) to provide the title compound as yellow solid.

HPLC: Rt$_{H7}$=2.822 min; ESIMS [M+H]$^+$=242.0/244.0; $^1$H-NMR (600 MHz, DMSO-d$_6$): δ 8.91-8.78 (m, 1H), 8.29-8.18 (m, 1H), 5.19 (d, 1H), 4.60 (d, 1H), 3.93 (q, 2H), 3.92 (s, 3H), 1.37 (t, 3H).

b) 5-Acetyl-3-chloro-pyridine-2-carboxylic acid methyl ester

To a solution of 3-chloro-5-(1-ethoxy-vinyl)-pyridine-2-carboxylic acid methyl ester (359 mg, 1.485 mmol) in THF (3.6 ml) was added para-toluenesulfonic acid monohydrate (565 mg, 2.97 mmol) and the mixture was stirred for 1 h. The reaction mixture was diluted with TBME and sat. aq. NaHCO$_3$, the layers were separated and the aq. Phase was extracted with TBME. The combined organic layers were washed with sat. aq. NaHCO$_3$ and sat. aq. NaCl, dried with MgSO$_4$, filtered and concentrated under reduced pressure. The residue was purified by chromatography on silica gel (cyclohexane/EtOAc 9:1 to 6/1) to provide the title compound as yellow solid.

HPLC: Rt$_{H8}$=2.604 min; ESIMS [M+H]$^+$=214.0/216.0; $^1$H-NMR (600 MHz, DMSO-d$_6$): δ 9.17-8.99 (m, 1H), 8.63-8.46 (m, 1H), 3.96 (s, 3H), 2.69 (s, 3H).

c) 3-Chloro-5-(1,1-difluoro-ethyl)-pyridine-2-carboxylic acid methyl ester

To a solution of 5-acetyl-3-chloro-pyridine-2-carboxylic acid methyl ester (278 mg, 1.30 mmol) in DCM (2.8 ml) was added Deoxofluor® (50 w-% in toluene, 1.44 ml, 3.9 mmol) and the reaction mixture was stirred protected from sunlight at it for 6 h, more Deoxofluor® (50 w-% in toluene, 1.44 ml, 3.9 mmol) was added and the mixture was stirred over night. The reaction mixture was poured on cold sat. aq. NaHCO$_3$ (strong gas evolution), TBME was added and the layers were separated. The aq. phase was extracted with TBME, the combined TBME layers were washed with sat. aq. NaHCO$_3$, sat. aq. NaCl, dried with MgSO$_4$, filtered and evaporated. The residue was purified by chromatography on silica gel (cyclohexane/EtOAc 95:5 to 93/7) to provide the title compound as colorless oil.

HPLC: $Rt_{H8}$=3.140 min; ESIMS [M+H]$^+$=236.0/238.0; $^1$H-NMR (600 MHz, DMSO-d$_6$): δ 8.84 (s, 1H), 8.40 (s, 1H), 3.95 (s, 3H), 2.07 (t, 3H).

d) 3-Chloro-5-(1,1-difluoro-ethyl)-pyridine-2-carboxylic acid

To a solution of 3-chloro-5-(1,1-difluoro-ethyl)-pyridine-2-carboxylic acid methyl ester (272 mg, 1.154 mmol) in THF (6 ml) was added LiOH (30.4 mg, 1.27 mmol) in water (0.5 ml) and the mixture was stirred for 3.5 h. To the mixture was added 6N HCl (0.212 ml, 1.27 mmol) and the solvent was evaporated. The residue was taken up in toluene and evaporated (2×) to provide the title compound as colorless solid together with LiCl. This material was directly used in the coupling step without further purification.

HPLC: $Rt_{H5}$=2.743 min; ESIMS [M+H]$^+$=222.0/224.0; $^1$H-NMR (600 MHz, DMSO-d$_6$): δ 8.76 (s, 1H), 8.29 (s, 1H), 3.37 (br. s, 1H), 2.06 (t, 3H).

The invention claimed is:

1. A compound of formula (I), or a pharmaceutically acceptable salt thereof,

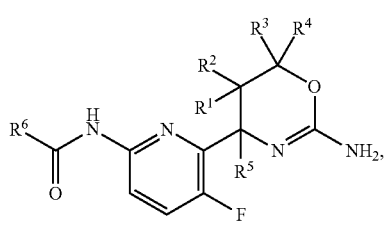

wherein
R$^1$ and R$^2$ are independently hydrogen or halogen;
R$^3$ and R$^4$ are independently hydrogen or C$_{1-3}$alkyl; or R$^3$ and R$^4$ taken together are cyclopropyl;
or R$^1$ and R$^4$ are hydrogen and R$^2$ and R$^3$ taken together are —CH$_2$—O—CH$_2$—;
R$^5$ is C$_{1-3}$alkyl, halogen-C$_{1-3}$alkyl or C$_{1-3}$alkoxy-C$_{1-3}$alkyl; and
R$^6$ is phenyl or a 5- or 6-membered monocyclic heteroaryl comprising 1, 2, 3 or 4 heteroatoms independently selected from N, O and S, and wherein said phenyl or heteroaryl is optionally substituted by 1, 2, 3 or 4 substituents independently selected from halogen, cyano, amino, hydroxy, C$_{1-4}$alkyl, halogen-C$_{1-4}$alkyl, halogen-C$_{1-4}$alkylthio, halogen-C$_{1-4}$alkoxy, C$_{1-4}$alkoxy, C$_{1-4}$alkoxy-C$_{1-4}$alkyl, C$_{1-4}$alkoxy-C$_{1-4}$alkoxy, C$_{1-4}$alkoxy-C$_{1-4}$alkylthio, C$_{1-4}$alkoxy-C$_{2-4}$alkenyl, C$_{1-4}$alkoxy-C$_{2-4}$alkynyl, hydroxy-C$_{1-4}$alkyl, hydroxy-C$_{2-4}$alkenyl and hydroxy-C$_{2-4}$alkynyl.

2. A compound according to claim 1, or a pharmaceutically acceptable salt thereof, wherein R$^1$ and R$^2$ are both fluoro.

3. A compound according to claim 1, or a pharmaceutically acceptable salt thereof, wherein R$^3$ and R$^4$ are both hydrogen.

4. A compound according to claim 1, or a pharmaceutically acceptable salt thereof, wherein R$^5$ is methyl.

5. A compound according to claim 1, or a pharmaceutically acceptable salt thereof, wherein R$^6$ is a 6-membered monocyclic heteroaryl comprising 1, 2, 3 or 4 heteroatoms independently selected from N, O and S, and wherein said heteroaryl is optionally substituted by 1, 2, 3 or 4 substituents independently selected from halogen, cyano, amino, hydroxy, C$_{1-4}$alkyl, halogen-C$_{1-4}$alkyl, halogen-C$_{1-4}$alkylthio, halogen-C$_{1-4}$alkoxy, C$_{1-4}$alkoxy, C$_{1-4}$alkoxy-C$_{1-4}$alkyl, C$_{1-4}$alkoxy-C$_{1-4}$alkoxy and C$_{1-4}$alkoxy-C$_{1-4}$alkylthio.

6. A compound according to claim 1, or a pharmaceutically acceptable salt thereof, wherein R$^6$ is a pyridin-2-yl group which is substituted by 2 substituents and wherein one of the substituents is located at the para position and one of the substituents is located at the ortho position of the pyridin-2-yl group relative to the amide linker and wherein the substituents are independently selected from halogen, cyano, amino, hydroxy, methyl, trifluoromethyl, methoxy and trifluoromethoxy.

7. A compound according to claim 1 which is selected from:
5-Cyano-3-methyl-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide;
3-Chloro-5-cyano-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide;
3-Chloro-5-cyano-pyridine-2-carboxylic acid [6-((R)-2-amino-5,5-difluoro-4,6,6-trimethyl-5,6-dihydro-4H-[1,3]oxazin-4-yl)-5-fluoro-pyridin-2-yl]-amide;
5-Cyano-3-methyl-pyridine-2-carboxylic acid {6-[(R)-2-amino-5,5-difluoro-4-(2-methoxy-ethyl)-5,6-dihydro-4H-[1,3]oxazin-4-yl]-5-fluoro-pyridin-2-yl}-amide;
3-Chloro-5-trifluoromethyl-pyridine-2-carboxylic acid {6-[(R)-2-amino-5,5-difluoro-4-(2-methoxy-ethyl)-5,6-dihydro-4H[1,3]oxazin-4-yl]-5-fluoro-pyridin-2-yl}-amide;
3-Chloro-5-trifluoromethyl-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide;
3-Amino-5-trifluoromethyl-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide;
3,5-Dichloro-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide;
3-Amino-5-(2,2,2-trifluoro-ethoxy)pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide;
3-Amino-5-(2,2-difluoro-ethoxy)-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide;
3-Amino-5-(3-fluoro-propoxy)-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide;
5-Methoxy-3-methyl-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide;
3-Amino-5-(3-methoxy-prop-1-ynyl)-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide;
3-Amino-5-fluoromethoxy-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide;
3-Amino-5-(2-methoxy-ethoxy)-pyrazine-2-carboxylic acid [6-((R)-2-amino-5,5-difluoro-4-methyl-5,6-dihydro-4H-[1,3]oxazin-4-yl)-5-fluoro-pyridin-2-yl]amide;

3-Amino-5-(3-hydroxy-prop-1-ynyl)-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide;

3-Amino-5-fluoro-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide;

3-Amino-5-chloro-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide;

3-Chloro-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide;

3-Chloro-5-(3-methoxy-prop-1-ynyl)pyridine-2-carboxylic acid [6-((R)-2-amino-5,5-difluoro-4-methyl-5,6-dihydro-4H-[1,3]oxazin-4-yl)-5-fluoro-pyridin-2-yl]-amide;

3-Amino-5-difluoromethyl-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide;

3-Amino-5-(2-chloro-ethoxy)-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide;

3-Chloro-5-(2,2-difluoro-ethoxy)-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide;

3-Amino-5-(2-fluoro-ethoxy)-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide;

3-Chloro-5-fluoromethoxy-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide;

3-Chloro-5-ethoxy-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide;

3-Amino-5-(penta-deutero-ethoxy)-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide;

3-Amino-5-(2-methoxy-ethyl)-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide;

4-Chloro-1-difluoromethyl-1H-pyrazole-3-carboxylic acid [6-((R)-2-amino-5,5-difluoro-4-methyl-5,6-dihydro-4H-[1,3]oxazin-4-yl)-5-fluoro-pyridin-2-yl]-amide;

3-Amino-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide;

3-Chloro-5-(3-hydroxy-prop-1-ynyl)-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide;

3-Amino-5-difluoromethyl-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide;

3-Amino-6-chloro-5-(1,1-difluoro-ethyl)-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide;

5-Cyano-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide;

3-Chloro-5-(1,1-difluoro-ethyl)-pyridine-2-carboxylic acid [6-((R)-2-amino-5,5-difluoro-4-methyl-5,6-dihydro-4H-[1,3]oxazin-4-yl)-5-fluoro-pyridin-2-yl]-amide; and 3-Amino-5-(1,1-difluoro-ethyl)-pyrazine-2-carboxylic acid [6-((R)-2-amino-5,5-difluoro-4-methyl-5,6-dihydro-4H-[1,3]oxazin-4-yl)-5-fluoro-pyridin-2-yl]-amide;

and pharmaceutically acceptable salts thereof.

8. A compound, or a pharmaceutically acceptable salt thereof, according to claim 1 which is

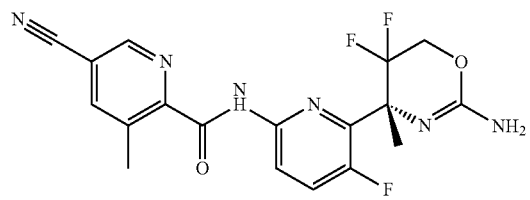 [SMILES: Cc1cc(C#N)cnc1C(=O)Nc1ccc(F)c([C@@]2(C)N=C(N)OCC2(F)F)n1]

9. A compound, or a pharmaceutically acceptable salt thereof, according to claim 1 which is

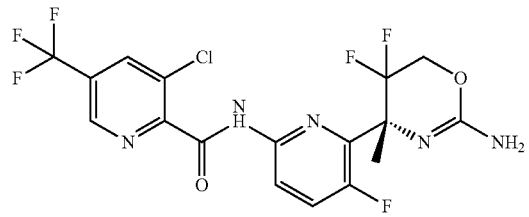 [SMILES: C[C@]1(c2nc(NC(=O)c3ncc(C(F)(F)F)cc3Cl)ccc2F)N=C(N)OCC1(F)F]

10. A pharmaceutical composition comprising a compound according to claim 1, or a pharmaceutically acceptable salt thereof, as active pharmaceutical ingredient in association with at least one pharmaceutically acceptable carrier or diluent.

* * * * *